(12) United States Patent
Crawford et al.

(10) Patent No.: US 9,796,999 B2
(45) Date of Patent: Oct. 24, 2017

(54) DETECTION OF OLIGOSACCHARIDES

(71) Applicant: BIOMARIN PHARMACEUTICAL INC., Novato, CA (US)

(72) Inventors: Brett E. Crawford, Poway, CA (US); Jillian R. Brown, Poway, CA (US); Charles A. Glass, San Diego, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 143 days.

(21) Appl. No.: 14/706,794

(22) Filed: May 7, 2015

(65) Prior Publication Data

US 2015/0307915 A1   Oct. 29, 2015

Related U.S. Application Data

(63) Continuation of application No. 12/649,094, filed on Dec. 29, 2009, now Pat. No. 9,029,530.

(60) Provisional application No. 61/142,291, filed on Jan. 2, 2009, provisional application No. 61/164,365, filed on Mar. 27, 2009.

(51) Int. Cl.
| | |
|---|---|
| *C12Q 1/527* | (2006.01) |
| *C07H 3/06* | (2006.01) |
| *C07H 3/04* | (2006.01) |
| *C07H 13/04* | (2006.01) |
| *C07H 5/06* | (2006.01) |
| *A61K 31/702* | (2006.01) |
| *G01N 33/66* | (2006.01) |
| *C07H 7/033* | (2006.01) |
| *C07H 11/00* | (2006.01) |

(52) U.S. Cl.
CPC ............ *C12Q 1/527* (2013.01); *A61K 31/702* (2013.01); *C07H 3/04* (2013.01); *C07H 3/06* (2013.01); *C07H 5/06* (2013.01); *C07H 7/033* (2013.01); *C07H 11/00* (2013.01); *C07H 13/04* (2013.01); *G01N 33/66* (2013.01); *G01N 2333/988* (2013.01); *G01N 2400/40* (2013.01); *G01N 2800/042* (2013.01); *G01N 2800/52* (2013.01); *G01N 2800/7071* (2013.01)

(58) Field of Classification Search
None
See application file for complete search history.

(56) References Cited

U.S. PATENT DOCUMENTS

| | | | |
|---|---|---|---|
| 5,185,245 A | 2/1993 | Heimer | |
| 6,117,647 A | 9/2000 | Romisch et al. | |
| 6,143,730 A | 11/2000 | Parish et al. | |
| 6,653,285 B1 | 11/2003 | Takashima et al. | |
| 6,852,696 B2 | 2/2005 | Takashima et al. | |
| 6,923,965 B2 | 8/2005 | Takashima et al. | |
| 6,936,424 B1 | 8/2005 | Watkins et al. | |
| 7,651,847 B2 | 1/2010 | Lebrilla et al. | |
| 8,183,003 B2 | 5/2012 | Crawford et al. | |
| 8,232,073 B2 | 7/2012 | Crawford et al. | |
| 8,592,140 B2 | 11/2013 | Crawford et al. | |
| 2002/0102737 A1 | 8/2002 | Millington et al. | |
| 2003/0024012 A1 | 1/2003 | Abdennebi-Najar et al. | |
| 2003/0054991 A1 | 3/2003 | Takashima et al. | |
| 2003/0228259 A1 | 12/2003 | Hellerstein | |
| 2004/0138105 A1 | 7/2004 | Takashima et al. | |
| 2005/0159343 A1 | 7/2005 | Takashima et al. | |
| 2005/0238536 A1 | 10/2005 | Striepeke et al. | |
| 2006/0079483 A1 | 4/2006 | Hung et al. | |
| 2006/0269974 A1 | 11/2006 | Dwek et al. | |
| 2006/0286034 A1 | 12/2006 | Meikle et al. | |
| 2007/0161074 A1 | 7/2007 | Tomatsu et al. | |
| 2008/0071148 A1 | 3/2008 | Bosques et al. | |
| 2008/0153752 A1 | 6/2008 | Takashima et al. | |
| 2010/0048638 A1 | 2/2010 | Crawford et al. | |
| 2010/0173337 A1 | 7/2010 | Crawford et al. | |
| 2010/0184013 A1 | 7/2010 | Crawford et al. | |
| 2010/0248365 A1 | 9/2010 | Crawford et al. | |
| 2011/0311988 A1 | 12/2011 | Crawford et al. | |
| 2012/0009616 A1 | 1/2012 | Crawford et al. | |
| 2012/0100609 A1 | 4/2012 | Crawford et al. | |
| 2012/0289415 A1 | 11/2012 | Bosques et al. | |
| 2012/0295890 A1 | 11/2012 | Crawford et al. | |
| 2013/0149729 A1 | 6/2013 | Crawford et al. | |
| 2013/0217056 A1 | 8/2013 | Crawford et al. | |

FOREIGN PATENT DOCUMENTS

| | | |
|---|---|---|
| GB | 2468386 A | 9/2010 |
| WO | 01/31045 A1 | 5/2001 |
| WO | 01/36977 A2 | 5/2001 |
| WO | 01/94941 A2 | 12/2001 |
| WO | 01/94941 A3 | 8/2003 |

(Continued)

OTHER PUBLICATIONS

Toma et al., "Differences in the Nonreducing Ends of Heparan Sulfates Excreted by Patients with Mucopolysaccharidoses Revealed by Bacterial Heparitinases: A New Tool for Structural Studies and Differential Diagnoses of Sanfilippo's and Hunter's Syndromes" Laboratory Investigation (1996) vol. 75 No. 6 pp. 771-781.*

Van Boeckel et al., "Conformational analysis of synthetic heparin-like oligosaccharides containing alpha-L-idopyranosyluronic acid" Recl Tray Chim Phays-Bas (1987) vol. 106 pp. 19-29.*

An et al., "Glucose tetrasaccharide as a biomarker for monitoring the therapeutic response to enzyme replacement therapy for Pompe disease," Mol. Genet. Metab. 85:247-254 (2005).

An et al., "Profiling of glycans in serum for the discovery of potential biomarkers for ovaraian cancer," J. Proteome Res. 5(7):1626-1635 (2006).

Byers et al., "Glycosaminoglycan accumulation and excretion in the mucopolysaccharidoses: Characterization and basis of a diagnostic test for MPS," Mol. Genet. Metab. 65(4):282-290 (1998).

Calabro et al., "Microanalysis of enzyme digests of hyaluronan and chondroitin/dermatan sulfate by fluorophore-assisted carbohydrate electrophoresis (FACE)," Glycobiology 10(3):273-281 (2000).

(Continued)

Primary Examiner — Eric Olson
(74) Attorney, Agent, or Firm — Jones Day

(57) ABSTRACT

Provided herein are processes for detecting oligosaccharides in a biological sample. In specific instances, the biological sample is provided from an individual suffering from a disorder associated with abnormal glycosaminoglycan accumulation.

28 Claims, 45 Drawing Sheets

(56) References Cited

FOREIGN PATENT DOCUMENTS

| | | |
|---|---|---|
| WO | 03/092601 A2 | 11/2003 |
| WO | 03/106997 A1 | 12/2003 |
| WO | 2004/019040 A1 | 3/2004 |
| WO | 03/092601 A3 | 9/2004 |
| WO | 2007/010089 A2 | 1/2007 |
| WO | 2007/010089 A3 | 5/2007 |
| WO | 2007/138263 A1 | 12/2007 |
| WO | 2010/078511 A2 | 7/2010 |
| WO | 2010/078514 A2 | 7/2010 |
| WO | 2010/078511 A3 | 10/2010 |

OTHER PUBLICATIONS

Calabro et al., "Adaptation of FACE methodology for microanalysis of total hyaluronan and chondroitin sulfate composition from cartilage," Glycobiology 10(3):283-293 (2000).
Daud et al., "Synthetic heparin pentasaccharide depolymerization by heparinase 1: Molecular and biological implications," Clin. Appl. Thromb. Hemost. 7(1):58-64 (2001).
Deakin et al., "A simplified and sensitive fluorescent method for disaccharide analysis of both heparin sulfate and chondroitin-dermatan sulfates from biological samples," Glycobiology 18:483-491 (2008).
Deegan et al., "Clinical evaluation of chemokine and enzymatic biomarkers of Gaucher disease," Blood Cells Mol. Dis. 35(2):259-267 (2005).
Delaney et al., "A high-performance liquid chromatography approach for isolation and sequencing of chondroitin sulfate oligosaccharides," Anal. Biochem. 108(1):25-34 (1980).
Ferro et al., "Evidence of conformational equilibrium of the sulfated L-iduronate residue in heparin and in synthetic heparin mono- and oligosaccharides: NMR and force-field studies," J. Am. Chem. Soc. 108:6778-6784 (1986).
Freeman and Hopwood, "Human alpha-L-iduronidase. Catalytic properties and an integrated role in the lysosomal degradation of heparan sulphate," Biochem. J. 282(Pt 3):899-908 (1992).
Fuller et al., "Glycosaminoglycan degradation fragments in mucopolysaccharidosis I," Glycobiology 14(5):443-450 (2004).
Hansen et al., "HPLC glycosaminoglycan analysis in patients with Graves' disease," Clin. Sci. (Lond) 92(5):511-517 (1997).
Hitchcock et al., "Comparative glycomics of connective tissue glycosaminoglycans," Proteomics 8(7):1384-1397 (2008).
Honda et al., "High-performance capillary electrophoresis of unsaturated oligosaccharides derived from glycosaminoglycans by digestion with chondroitinase ABC as 1-phenyl-3 methyl-5-pyrazolone derivatives," J. Chromatogr. 608(1-2):289-295 (1992).
Hopwood and Elliott "Urinary excretion of sulphated N-acetylhexosamines in patients with various mucopolysaccharidoses," Biochem. J. 229(3):579-586 (1985).
Imanari et al., "High performance liquid chromatographic analysis of glycosaminoglycan-derived oligosaccharides," J. Chromatogr. A 720(1-2):275-293 (1996).
Jacquinet et al., "Synthesis of heparin fragments. A chemical synthesis of the trisaccharide O-(2-deoxy-2-sulfamido-3,6-di-O-sulfo-alpha-D-glucopyranosyl)-(1-4)-2-deoxy-2-sulfamido-6-O-sulfo-D-glucopyranose heptasodium salt," Carbohydr. Res. 130:221-241 (1984).
Kimura et al., "Chemical structure of urinary dermatan sulfate excreted by a patient with the Hunter syndrome," Tohoku J. Exp. Med. 131(3):241-247 (1980).
Kimura et al., "Fractionation and characterization of urinary heparan sulfate excreted by patients with Sanfilippo syndrome," Tohoku J. Exp. Med. 144(3):227-236 (1984).
Kirmiz et al., "A serum glycomics approach to breast cancer biomarkers," Mol. Cell. Proteomics 6(1):43-55 (2007).
Kodama et al., "High-performance liquid chromatography of pyridylamino derivatives of unsaturated disaccharides produced from chondroitin sulfate isomers by chondroitinases," J. Biochem. 96(4):1283-1287 (1984).
Kodama et al., "Liquid-chromatographic determination of urinary glycosaminoglycans for differential diagnosis of genetic mucopolysaccharidoses," Clin. Chem. 31(1 Pt 1):30-34 (1986).
Lawrence et al., "Evolutionary differences in glycosaminoglycan fine structure detected by quantitative glycan reductive isotope labeling," J. Biol. Chem. 283(48):33674-33684 (2008).
Maccari et al., "Anomolous structure of urinary glycosaminoglycans in patients with pseudoxanthoma elasticum," Clin. Chem. 49(3):380-388 (2003).
Mao et al., "Capillary electrophoresis for the analysis of glycosaminoglycans and glycosaminoglycan-derived oligosaccharides," Biomed. Chromatogr. 16(2):77-94 (2002).
Mason et al., "Characterization of sulfated oligosaccharides in mucopolysaccharidosis type IIIA by electrospray ionization mass spectrometry," Anal. Chem. 78(13):4534-4542 (2006).
Minamisawa et al., "Microscale preparation of even- and odd-numbered N-acetylheparosan oligosaccharides," Carbohydr. Res. 341(2):230-237 (2006).
Minamisawa et al., "Systematic identification of N-acetylheparosan oligosaccharides by tandem mass spectrometric fragmentation," Rapid Commun. Mass Spectrom. 20(2):267-274 (2006).
Nader et al., "Chemistry of heparitin sulfate and heparin from normal tissues and from patients with Hunter syndrome," Biochim. Biophys. Acta 582(1):33-43 (1979).
Nomenclature Committee Consortium for Functional Glycomics "Symbol and Text Nomenclature for Representation of Glycan Structure" (May 2012) accessed on Internet on Sep. 12, 2012 at http://www.functionalglycomics.org/static/consortium/Nomenclature.shtml.
PLAAS et al., "Glycosaminoglycan sulfation in human osteoarthritis: Disease-related alterations at the non-reducing termini of chondroitin and dermatan sulfate," J. Biol. Chem. 273(20):12642-12649 (1998).
Pol-Fachin and Verli, "Depiction of the forces participating in the 2-O-sulfo•-L-iduronicacid conformational preference in heparin sequences in aqueous solutions," Carbohydr. Res. 343(9):1435-1445 (2008).
Rhomberg et al., "Mass spectrometric evidence for the enzymatic mechanism of the depolymerization of heparin-like glycosaminoglycans by heparinase II," Proc. Natl. Acad. U.S.A. 95(21):12232-12237 (1998).
Rong et al., "Substrate specificity of the heparin sulfate hexuronic acid 2-O-sulfotransferase," Biochemistry 40 (18):5548-5555 (2001).
Smeds et al. "Target selection of heparan sulfate hexuronic acid 2-O-sulfotransferase," Glycobiology 20 (10):1274-1282 (2010).
Thanawiroon et al., "Liquid chromatography/mass spectrometry sequencing approach for highly sulfated heparin-derived oligosaccharides," J. Biol. Chem. 279(4):2608-2615 (2004).
Thompson et al., "Oligosaccharide substrates for heparin sulfamidase," Anal. Chem. 152(2):412-422 (1986).
Toma et al., "Differences in the non-reducing ends of heparan sulfates excreted by patients with mucopolysaccharidoses revealed by bacterial heparitinases: A new tool for structural studies and differential diagnosis of Sanfilippo's and Hunter's syndromes," Lab. Invest. 75(6): 771-781 (1996).
Volpi et al., "Glycosaminoglycan composition of the large freshwater mollusk bivalve Anodonta anodonta," Biomacromolecules 6(6):3174-3180 (2005).
Volpi et al., "Mass spectrometry for the characterization of unsulfated chondroitin oligosaccharides from 2-mers to 16-mers. Comparison with hyaluronic acid oligomers," Rapid Commun. Mass Spectrom. 22(22):3526-3530 (2008).
Yamada et al., "Structural studies on the tri- and tetrasaccharides isolated from porcine intestinal heparin and characterization of heparinase/heparitinases using them as substrates," Glycobiology 4(1):69-78 (1994).
Yan et al., "Prediction and simulation on interaction between HIV-1 envelope protein gp120 and heparin," Chem. J. Chinese U. 25(3):522-525 (2004) (in Chinese with English abstract).
Yosizawa et al., "A simple method for the quantitation of glycuronic acid-containing glycosaminoglycans with mucopolysaccharidases," Anal. Biochem. 128(1):250-256 (1983).

(56) References Cited

OTHER PUBLICATIONS

EP 09837207.1 Supplementary Search Report dated Aug. 2, 2012.
GB 0922711.7 Examination Report dated Dec. 2, 2010.
International Search Report for PCT/US2009/069941 dated Aug. 27, 2010.
International Search Report for PCT/US2009/069944 dated Aug. 31, 2010.
International Search Report and Written Opinion for PCT/US2009/069946 dated Sep. 9, 2012.
Murata et al., "High-performance liquid chromatographic identification of eight constitutional disaccharides from leparan sulfate isomers digested with heparitinases", J Chromatogr B Biomed Appl., 670(1):3-10 (1995).

* cited by examiner

FIGURE 3B

| MPS Class | NRE (Non-Reducing End) | | Internal |
|---|---|---|---|
| Unaffected | Heterogeneous (very low levels) | | Normal composition 32 theoretical structures, 6 common Lyase generated double bond (-18 daltons) |
| MPS I Iduronidase | 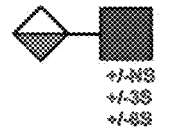 | Mass tagged Ido-Y 0-3 sulfates 8 theoretical structures | Normal composition 32 theoretical structures, 6 common Lyase generated double bond (-18 daltons) |
| MPS II 2-Sulfatase | 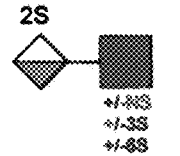 | Mass tagged Ido2S-Y e.g., 1-4 sulfates 16 theoretical structures | Normal composition 32 theoretical structures, 6 common Lyase generated double bond (-18 daltons) |
| MPS IIIA N-Sulfatase | 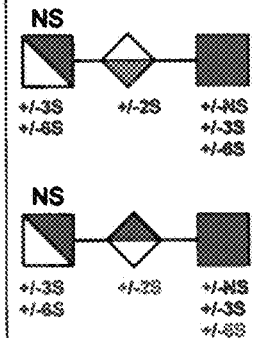 | Mass tagged GlcNS-X-Y e.g., 1-6 sulfates 64 theoretical structures | Normal composition 32 theoretical structures, 6 common Lyase generated double bond (-18 daltons) |
| MPS IIIB N-acety-glucosaminidase | 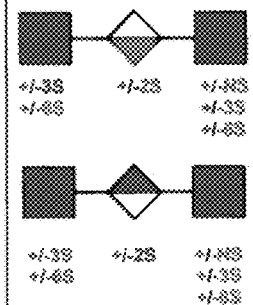 | Mass tagged GlcNAc-X-Y e.g., 0-4 sulfates 32 theoretical structures | Normal composition 32 theoretical structures, 6 common Lyase generated double bond (-18 daltons) |

Figure 4
 Formula I-A
 Formula I-B
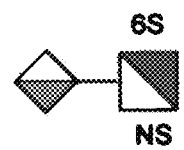 Formula I-C
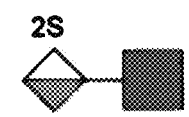 Formula I-D
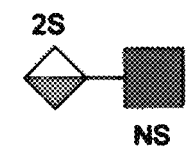 Formula I-E
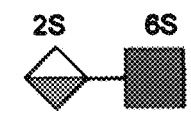 Formula I-F
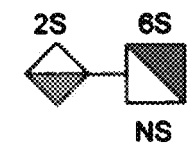 Formula I-G Figure 13
  Formula XI-A
  Formula XI-B
  Formula XI-C
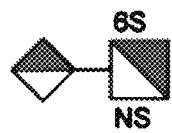  Formula XI-D Figure 14
 Formula XII-A
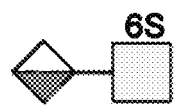 Formula XII-B
 Formula XII-C
 Formula XII-D Figure 15
Formula XIII-A
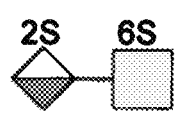
Formula XIII-B
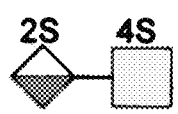
Formula XIII-C
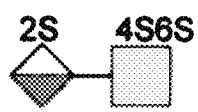
Formula XIII-D

Figure 19
  Formula XIX-A
  Formula XIX-B
  Formula XIX-C
  Formula XIX-D
  Formula XIX-E
  Formula XIX-F
Figure 20
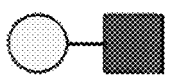  Formula XX-A
  Formula XX-B

Figure 21
 Formula XXX-A
 Formula XXX-B
 Formula XXX-C
 Formula XXX-D
 Formula XXX-E
 Formula XXX-F
 Formula XXX-G
 Formula XXX-H
 Formula XXX-I
 Formula XXX-J

Figure 23
 Formula XXXII-A
 Formula XXXII-B
 Formula XXXII-C

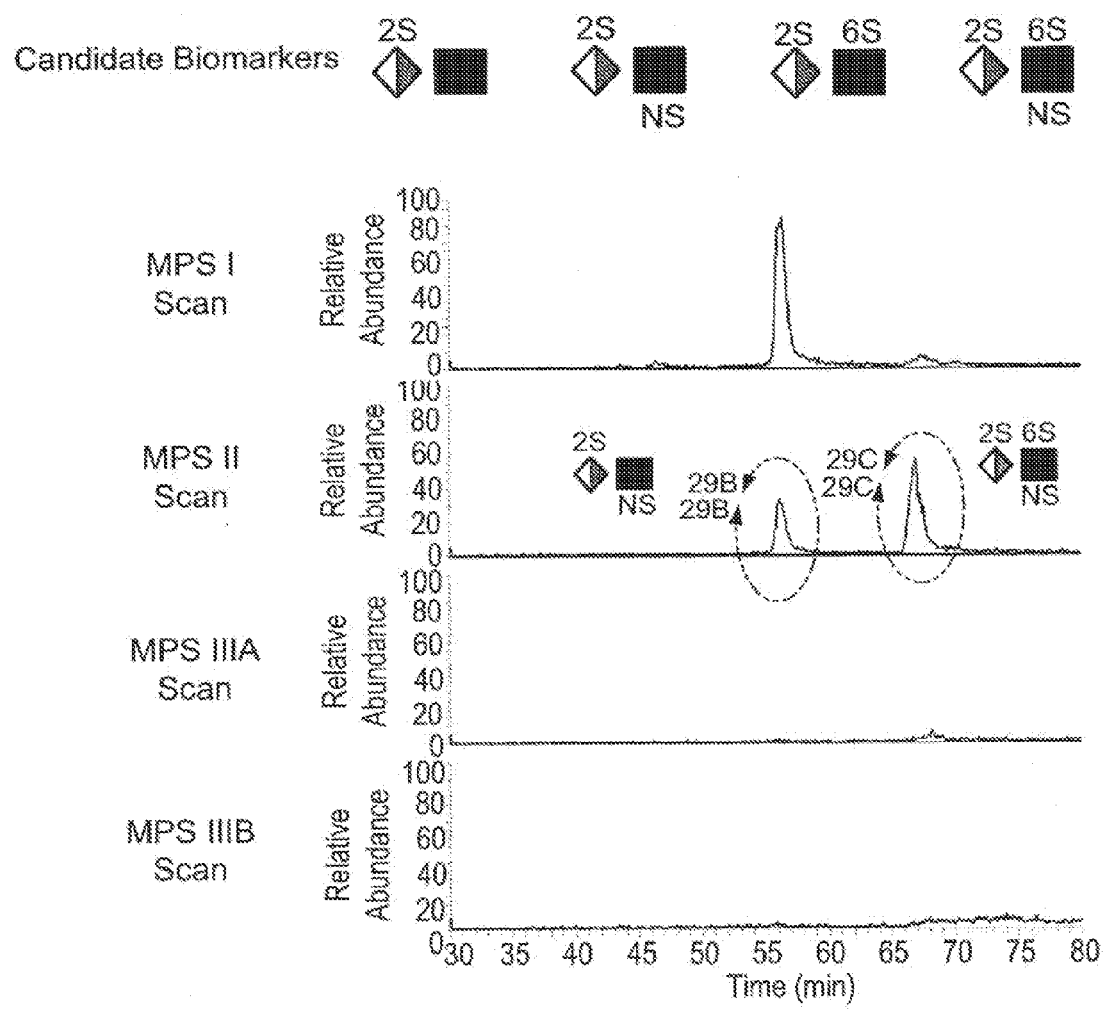

MPS IIIB MOUSE - LIVER

MPS IIIB MOUSE – BRAIN

MPS IIIB MOUSE – KIDNEY

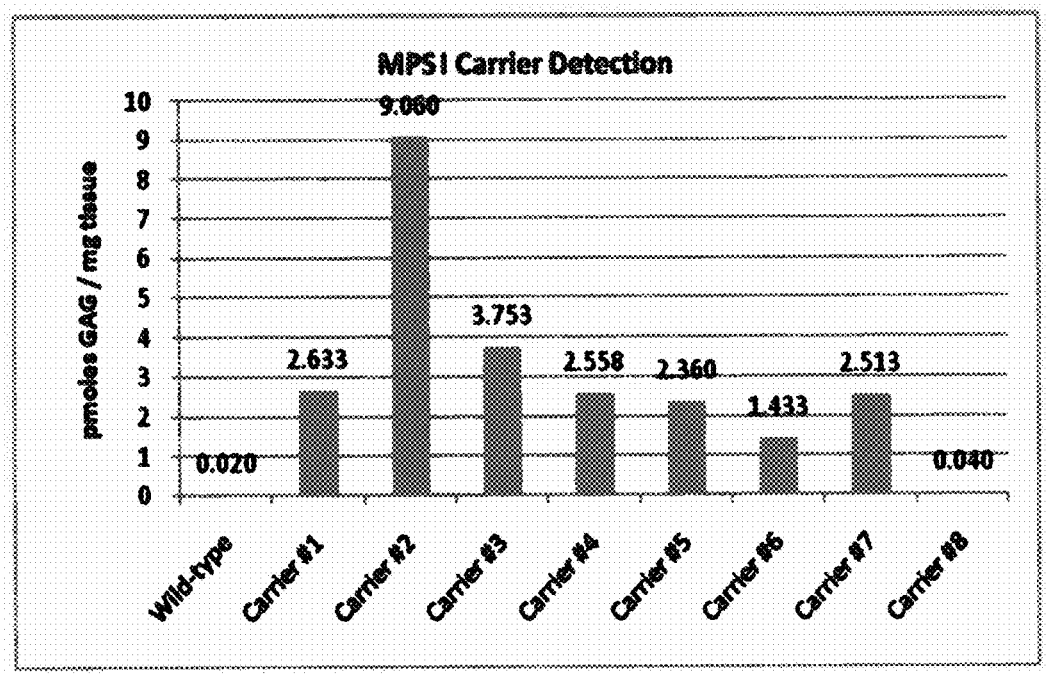

DETECTION OF OLIGOSACCHARIDES

CROSS-REFERENCE TO RELATED APPLICATIONS

This application is a continuation application of U.S. application Ser. No. 12/649,094 (now U.S. Pat. No. 9,029,530), which claims the benefit of U.S. Provisional Application No. 61/142,291, filed 2 Jan. 2009, and U.S. Provisional Application No. 61/164,365, filed 27 Mar. 2009, each of which applications is incorporated herein by reference.

BACKGROUND OF THE INVENTION

Glycosaminoglycans comprise a reducing end and a non-reducing end. Normal biological processes degrade glycosaminoglycans (such as heparan sulfate which has a normal component of about 50-80 kDa) into monosaccharides. Disorders associated with abnormal glycosaminoglycan degradation, biosynthesis, and/or accumulation can result in an accumulation of glycosaminoglycans and fragments thereof.

SUMMARY OF THE INVENTION

Described herein are populations of glycosaminoglycans that are transformed into populations of oligosaccharides using glycosaminoglycan lyases. Further described herein are the use of analytical instruments to characterize the population of oligosaccharides in order to provide relevant information about the population of oligosaccharides, the population of glycosaminoglycans and the biological sample that provided the population of glycosaminoglycans.

Provided in certain embodiments herein is a process for diagnosing the identity and/or severity of abnormal glycosaminoglycan accumulation in an individual, or a disorder thereof, the process comprising the steps of:
 a. using an analytical instrument to detect the presence of and/or measure the amount of a population of one or more oligosaccharides present in a transformed biological sample that has been prepared by:
    treating a population of glycosaminoglycans, in or isolated from a biological sample from the individual to transform the glycosaminoglycans into the population of the one or more oligosaccharide;
 b. displaying or recording the presence of or a measure of a population of one or more oligosaccharide.

In certain embodiments, provided is a process for diagnosing the presence, identity, and/or severity of abnormal glycosaminoglycan accumulation in an individual, or a disorder thereof, the process comprising the steps of:
 a. generating a biomarker comprising of one or more non-reducing end oligosaccharides, wherein the biomarker is a saturated oligosaccharide and is generated by treating a population of glycosaminoglycans, in or isolated from a biological sample from the individual, with at least one digesting glycosaminoglycan lyases, wherein prior to lyase treatment, such oligosaccharide biomarker is not present in abundance in samples from individuals with abnormal glycosaminoglycan accumulation relative to individuals with normal glycosaminoglycan;
 b. using an analytical instrument to detect the presence of and/or measure the amount of the biomarker produced and displaying or recording the presence of or a measure of a population of the biomarker.

In specific embodiments, the presence of and/or measure the amount of the biomarker is utilized to diagnose of the presence, identity, and/or severity of abnormal glycosaminoglycan accumulation.

In certain embodiments, the oligosaccharide(s) detected or measured is one or more C4-C5 non-reducing end saturated oligosaccharide(s).

In some embodiments, treating a population of glycosaminoglycans to transform the glycosaminoglycans into the population of the one or more oligosaccharide comprises contacting the glycosaminoglycans with at least one digesting glycosaminoglycan lyase. In some embodiments, the at least one digesting glycosaminoglycan lyase is one or more heparin lyase, one or more chondroitinase, one or more keratanase, one or more hyaluronidase, or a combination thereof. In specific embodiments, the at least one digesting glycosaminoglycan lyase is one or more heparin lyase.

In certain embodiments, the one or more oligosaccharides detected and/or measured are free of carbon-carbon unsaturation. In various embodiments, the abnormal glycosaminoglycan accumulation comprises abnormal heparan sulfate accumulation, abnormal chondroitin sulfate accumulation, abnormal keratan sulfate accumulation, abnormal hyaluronan accumulation, or a combination thereof. In specific embodiments, the abnormal glycosaminoglycan accumulation is abnormal heparan sulfate accumulation.

In various embodiments, any process descried herein of preparing a transformed biological sample comprises purifying a population of oligosaccharides in the biological sample that has been treated with the at least one heparin lyase, the transformed biological sample comprising the isolated population of oligosaccharides. In some embodiments, any process described herein of preparing a transformed biological sample comprises purifying a population of glycosaminoglycans in the biological sample prior to treatment with the at least one heparin lyase.

In certain embodiments, any process described herein of detecting the presence of or measuring the amount of a population of one or more oligosaccharide present in a transformed biological sample comprises:
 a. isolating a subpopulation of one or more oligosaccharides in the transformed biological sample; and
 b. detecting the presence of and/or measuring the amount of one or more oligosaccharides present in the subpopulation.

In specific embodiments, a subpopulation of one or more oligosaccharides is isolated using, by way of non-limiting example, chromatography or electrophoresis. In specific embodiments, the chromatography is high performance liquid chromatography (HPLC), gas chromatography (GC), column chromatography, affinity chromatography, or thin layer chromatography (TLC). In some embodiments, any process of detecting oligosaccharides described herein comprises detecting oligosaccharides using mass spectrometry.

In some embodiments, any process described herein of preparing a transformed biological sample comprises tagging the reducing end of a representative portion of the one or more oligosaccharides in the transformed biological sample with a detectable label. In specific embodiments, the detectable label is a mass label, a radio label, a fluorescent label, a chromophore label, or affinity label. In some embodiments, the tagged portion of the one or more oligosaccharides is detected or measured using UV-Vis spectroscopy, IR spectroscopy, mass spectrometry, or a combination thereof.

In certain embodiments, a digesting glycosaminoglycan lyase utilized in any process described herein comprises heparan sulfate, chondroitin sulfate, keratan sulfate, hyaluronan, or a combination thereof. In specific embodiments, a digesting glycosaminoglycan lyase utilized in any process described herein comprises heparan sulfate.

In some embodiments, a process described herein comprises detecting or measuring a disaccharide having the formula: [IdoA-GlcN(Ac)$_m$](SO$_3$R)$_n$, wherein m is 0-1, n is 0-3, and R is H or a negative charge. In some embodiments, the term R used in any formula described herein is H or a negative charge.

In specific embodiments, any process described herein comprises detecting or measuring a disaccharide with the formula:

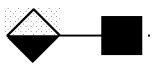

In some embodiments, the disaccharide above is detected and/or measured in a process of diagnosing a disorder associated with abnormal glycosaminoglycan degradation that is MPS I.

In some embodiments, any process described herein comprises detecting or measuring a disaccharide with the formula:

In some embodiments, the disaccharide above is detected and/or measured in a process of diagnosing a disorder associated with abnormal glycosaminoglycan degradation that is MPS II.

In some embodiments, any process described herein comprises detecting or measuring a trisaccharide with the formula [GlcN(Ac)$_m$-(IdoA/GlcA)-GlcN(Ac)$_n$](SO$_3$R)$_p$, wherein IdoA/GlcA is either IdoA or GlcA, m is 0-1, n is 0-1, p is 0-5, and R is H or a negative charge.

In certain embodiments, any process described herein comprises detecting or measuring a trisaccharide with the formula:

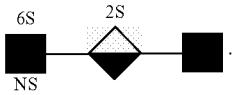

In some embodiments, the trisaccharide above is detected and/or measured in a process of diagnosing a disorder associated with abnormal glycosaminoglycan degradation that is MPS IIIA.

In certain embodiments, any process described herein comprises detecting or measuring a trisaccharide with the formula:

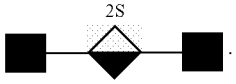

In some embodiments, the trisaccharide above is detected and/or measured in a process of diagnosing a disorder associated with abnormal glycosaminoglycan degradation that is MPS IIIB.

In certain embodiments, any process described herein comprises detecting or measuring a trisaccharide with the formula:

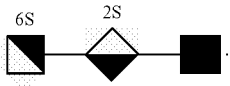

In some embodiments, the trisaccharide above is detected and/or measured in a process of diagnosing a disorder associated with abnormal glycosaminoglycan degradation that is MPS IIIC.

In certain embodiments, any process described herein comprises detecting or measuring a trisaccharide with the formula:

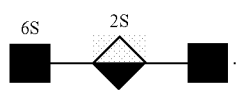

In some embodiments, the trisaccharide above is detected and/or measured in a process of diagnosing a disorder associated with abnormal glycosaminoglycan degradation that is MPS IIID In certain embodiments, any process described herein comprises detecting or measuring a disaccharide with the formula [GlcA-GlcN(Ac)$_n$](SO$_3$R)$_m$, wherein n is 0-1, m is 0-2, and R is H or a negative charge.

In certain embodiments, any process described herein comprises detecting or measuring a disaccharide with the formula:

In some embodiments, the disaccharide above is detected and/or measured in a process of diagnosing a disorder associated with abnormal glycosaminoglycan degradation that is MPS VII.

In various embodiments of the processes described herein, a population of glycosaminoglycans treated with at least one digesting glycosaminoglycan lyase comprises dermatan sulfate, chondroitin sulfate, or a combination thereof. In certain embodiments, any process described herein comprises detecting or measuring a disaccharide with the formula: [Ido-GalNAc](SO$_3$R)$_n$, wherein n=0-2, and each R is independently H or a negative charge. In some embodiments, any process described herein comprises detecting or measuring a trisaccharide with the formula: [GalNAc4S-Ido-GlcNAc](SO$_3$R)$_n$, wherein n=0-3; and/or one or more trisaccharide with the formula: [GalNAc4S-GlcA-GlcNAc](SO$_3$R)$_m$, wherein m=0-1, and wherein each R is independently H or a negative charge.

In certain embodiments, any process described herein comprises detecting or measuring a disaccharide with the formula: [Gal6S-GalNAc](SO$_3$R)$_n$, wherein n=0-1, and wherein each R is independently H or a negative charge. In specific embodiments, detection and/or measurement of [Gal6S-GalNAc]$(SO_3R)_n$ is used in a method of diagnosing MPS IVA or the severity thereof. In some embodiments, any process described herein comprises detecting or measuring a disaccharide with the formula: [Gal-GalNAc]$(SO_3R)_n$, wherein n=0-1, and wherein each R is independently H or a negative charge. In specific embodiments, detection and/or measurement of [Gal-GalNAc]$(SO_3R)_n$ is used in a method of diagnosing MPS IVB or the severity thereof.

In some embodiments, any process described herein comprises:
  a. comparing an amount of a population of one or more oligosaccharide present in a transformed biological sample to an amount of a population of one or more oligosaccharide present in a control biological sample that has been treated in a manner substantially similar to the transformed biological sample.

In certain embodiments, a control biological sample utilized in any process described herein was provided from an individual that does not have mucopolysaccharidosis (e.g., a non-MPS cell line). In some embodiments, any control biological sample utilized in a process described herein was provided from an individual that has mucopolysaccharidosis. In specific embodiments, a control biological sample was provided from an individual that has MPS I, MPS II, MPS IIIA, MPS IIIB, MPS IIIC, MPS IIID, MPS IVA, MPS IVB, MPS VII, MPS IX, or a combination thereof. In specific embodiments, a control biological sample was provided from an individual that has MPS I, MPS II, MPS IIIA, MPS IIIB, MPS IIIC, MPS IIID, MPS VII, or a combination thereof.

Provided in certain embodiments herein is an analytical sample comprising any oligosaccharide described herein, including an oligosaccharide described herein and further attached to a detectable label (e.g., at the reducing end of the oligosaccharide). In specific embodiments, provided herein is an analytical sample comprising one or more of any of FIGS. 4-23.

In specific embodiments, an analytical sample provided for herein is for use in high performance liquid chromatography. In some embodiments, an analytical sample provided for herein is for use in mass spectrometry. In certain embodiments, an analytical sample provided for herein is for use in gas chromatography. In some embodiments, any analytical sample provided herein comprises at least one disaccharide or trisaccharide from a transformed biological sample from an individual with a disorder associated with abnormal glycosaminoglycan accumulation.

Provided in some embodiments herein is an analytical method comprising treating a biological sample that comprises glycosaminoglycans with at least one digesting glycosaminoglycan lyase to transform a representative portion of the glycosaminoglycans into one or more oligosaccharides. In certain embodiments an analytical method provided for herein comprises purifying one or more oligosaccharides from other components of the biological sample. In some embodiments, the purifying step includes use of chromatography. In various embodiments, an analytical method provided for herein comprises detecting and/or measuring the presence of at least one of the oligosaccharides (e.g., after purification). In certain embodiments, oligosaccharides are detected and/or measured according to any process or method (used interchangeably herein) described herein using UV-Vis spectroscopy, IR spectroscopy, mass spectrometry, or a combination thereof. In some embodiments, any process described herein comprises tagging at least one of the oligosaccharides with a detectable label. In certain embodiments, the at least one digesting glycosaminoglycan lyase utilized in any process or method described herein comprises one or more heparin lyase, one or more chondroitinase, one or more keratanase, one or more hyaluronidase, or a combination thereof.

In specific embodiments, an analytical method described herein is used in a method of detecting and/or measuring one or more oligosaccharides that are free of carbon-carbon unsaturation.

In certain embodiments, any process described herein comprises detecting or measuring a disaccharide with the formula: [IdoA-GlcN(Ac)$_m$]$(SO_3R)_n$, wherein m is 0-1, n is 0-3, and R is H or a negative charge. In some embodiments, any process described herein comprises detecting or measuring a trisaccharide with the formula: [GlcN(Ac)$_m$-(IdoA/GlcA)-GlcN(Ac)$_n$]$(SO_3R)_p$, wherein IdoA/GlcA is either IdoA or GlcA, m is 0-1, n is 0-1, and p is 0-5. In certain embodiments, any process described herein comprises detecting or measuring a disaccharide with the formula: [GlcA-GlcN(Ac)$_n$]$(SO_3R)_m$, wherein n is 0-1, and m is 0-2. In some embodiments, any process described herein comprises detecting or measuring a disaccharide with the formula: [Ido-GalNAc]$(SO_3R)_n$, wherein n=0-2, and each R is independently H or a negative charge. In certain embodiments, any process described herein comprises detecting or measuring a trisaccharide with the formula: [GalNAc4S-Ido-GalNAc]$(SO_3R)_n$, wherein n=0-3; and/or one or more trisaccharide with the formula: [GalNAc4S-GlcA-GalNAc]$(SO_3R)_m$, wherein m=0-2, and wherein each R is independently H or a negative charge. In certain embodiments, any process described herein comprises detecting or measuring a disaccharide with the formula: GlcA-GlcNAc. In certain embodiments, any process described herein comprises detecting or measuring a disaccharide with the formula: [GlcA-GalNAc]$(SO_3R)_m$, wherein m is 0-2 (e.g., for diagnosing CS accumulation in MPS VII, or the severity thereof). In some embodiments, any process described herein comprises detecting or measuring a trisaccharide with the formula: [GlcNAc6S-Gal-GlcNAc]$(SO_3R)_n$, wherein n=0-2, and wherein each R is independently H or a negative charge. In certain embodiments, any process described herein comprises detecting or measuring a disaccharide with the formula: [Gal6S-GlcNAc]$(SO_3R)_n$, wherein n=0-1, and wherein each R is independently H or a negative charge. In certain embodiments, any process described herein comprises detecting or measuring a disaccharide with the formula: [Gal-GlcNAc]$(SO_3R)_n$, wherein n=0-1, and wherein each R is independently H or a negative charge.

In certain embodiments, a process described herein includes a method of monitoring the treatment of disorders associated with the abnormal degradation, biosynthesis and/or accumulation of glycosaminoglycans (GAGs), the methods comprising:
  a. following administration of an agent for treating MPS to an individual in need thereof, generating a biomarker comprising of one or more non-reducing end oligosaccharides, wherein the biomarker is a saturated oligosaccharide and is generated by treating a population of glycosaminoglycans, in or isolated from a biological sample from the individual, with at least one digesting glycosaminoglycan lyases, wherein prior to lyase treatment, such oligosaccharide biomarker is not present in abundance in samples from individuals with abnormal glycosaminoglycan accumulation relative to individuals with normal glycosaminoglycan;
  b. using an analytical instrument to detect the presence of and/or measure the amount of the biomarker produced and displaying or recording the presence of or a measure of a population of the biomarker.

In specific embodiments, increases or decreases in the amount of the biomarker measured (e.g., as compared to a biological sample previously analyzed in a similar or identical manner) is utilized to monitor the treatment of disorders associated with the abnormal degradation, biosynthesis and/or accumulation of glycosaminoglycans.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 3A-3C illustrate various oligosaccharide residues of GAGs. FIG. 3A illustrates the heparan sulfate fragments that accumulate in MPS II patients considering only the 3 most common modifications (N-, 2-O, and 6-O sulfation). Even for a relatively small nonasaccharides (n=4), there are well over 1,000 potential structures. FIGS. 3B and 3C illustrate predicted non-reducing end heparan sulfate biomarkers for 7 MPS classes.

FIG. 4 illustrates oligosaccharides of Formula I.
FIG. 13 illustrates oligosaccharides of Formula XI.
FIG. 14 illustrates oligosaccharides of Formula XII.
FIG. 15 illustrates oligosaccharides of Formula XIII.
FIG. 19 illustrates oligosaccharides of Formula XVIX.
FIG. 20 illustrates oligosaccharides of Formula XX.
FIG. 21 illustrates oligosaccharides of Formula XXX.
FIG. 23 illustrates oligosaccharides of Formula XXXII.

FIG. 29A illustrates mass spectrometry results for non-reducing end oligosaccharides in a MPS II sample.

FIGS. 43A, 43B, and 43C illustrate the treatment of different patients.

FIG. 44 illustrates detecting carriers of the genetic cause of MPS.

DETAILED DESCRIPTION OF THE INVENTION

Figure 1:
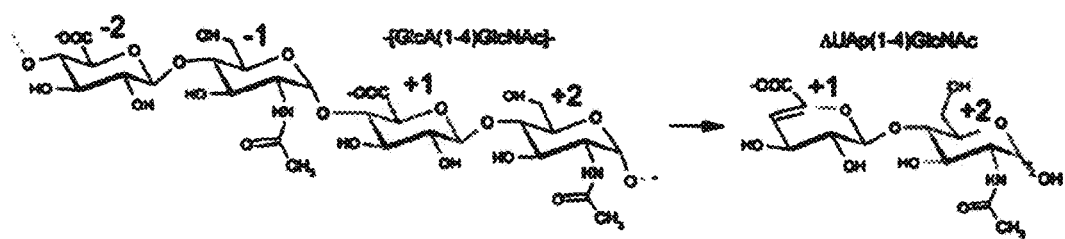
FIG. 1 illustrates the cleavage of the glycosaminoglycan (GAG) heparan sulfate with a glycosaminoglycan lyase (heparinase II).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Provided in certain embodiments herein are analytical methods for detecting and/or identifying glycosaminoglycans (GAGs) or other glycans (e.g., glycolipids) in biological sample. In certain embodiments, the glycans, e.g., glycosaminoglycans (GAGs), are present in cells within a biological sample (e.g., within a lysosome thereof), and/or are present in a biological sample free of cells. In certain embodiments, provided herein is a method of diagnosing any disorder characterized by the accumulation of glycosaminoglycans, such as a lysosomal storage disease (LSD). In some embodiments, the glycosaminoglycan accumulation is a primary accumulative effect. In certain instances, primary accumulative effects include accumulation that is a direct result of an abnormal biosynthetic process, such as abnormal production enzymes involved in the glycan biosynthetic pathway (e.g., under-production or production of poorly functioning enzymes), including glycan bio-synthesis or depolymerization. In other embodiments, the glycosaminoglycan accumulation is a secondary accumulative effect. In certain embodiments, a secondary accumulative effect results from a cascading effect, e.g., accumulation of other components, such as GAGs or other glycans, such as glycolipids, causes the GAG biosynthetic pathway to be hindered or interrupted.

In certain embodiments, glycosaminoglycans include, by way of non-limiting example, heparan sulfate, heparin, chondroitin sulfate, dermatan sulfate, hyaluronan, keratan sulfate, or the like, or a combination thereof. In certain embodiments, an analytical method provided herein comprising treating a biological sample that comprises glycosaminoglycans with at least one agent suitable for cleaving bonds between saccharide residues of glycosaminoglycans. In specific embodiments, treating a biological sample that comprises glycosaminoglycans with at least one agent suitable for cleaving bonds between saccharide residues of glycosaminoglycans comprises treating the biological sample with one or more digesting glycosaminoglycan (GAG) lyase. In some embodiments, any glycosaminoglycan (GAG) lyase suitable for cleaving the bonds (e.g., the bonds linking saccharide residues of the GAG to one another) of a glycosaminoglycan (GAG) analyze is utilized. In some embodiments, the lyase is utilized to transform a representative portion of the glycosaminoglycans into one or more oligosaccharides. In certain embodiments, such glycosaminoglycan (GAG) lyases are suitable for preparing di- and/or tri-saccharides from the glycosaminoglycan present. Glycosaminoglycan (GAG) lyases suitable for use in various embodiments provided herein include, by way of non-limiting example, one or more heparin lyase (heparinase), one or more chondroitinase, one or more keratanase, one or more hyaluronidase, or a combination thereof. Other glycans that are optionally detected by a method described herein include, e.g., glycolipids.

In some embodiments, lyases utilized herein include, by way of non-limiting example, Hyaluronate lyase, Pectate lyase, Poly(beta-D-mannuronate) lyase, Chondroitin ABC lyase, Chondroitin AC lyase, Oligogalacturonide lyase, Heparin lyase, Heparin-sulfate lyase, Pectate disaccharide-lyase, Pectin lyase, Poly(alpha-L-guluronate) lyase, Xanthan lyase, Exo-(1->4)-alpha-D-glucan lyase, Glucuronan lyase, Anhydrosialidase, Levan fructotransferase, Inulin fructotransferase, Inulin fructotransferase, Chondroitin B lyase. In certain instances, Hyaluronate lyase (EC 4.2.2.1) is an enzyme that catalyzes the cleavage or hyaluronate chains at a beta-D-GalNAc-(1->4)-beta-D-GlcA bond, ultimately breaking the polysaccharide down to 3-(4-deoxy-beta-D-gluc-4-enuronosyl)-N-acetyl-D-glucosamine. In some instances, Pectate lyase (EC 4.2.2.2) is an enzyme that catalyzes the eliminative cleavage of (1->4)-alpha-D-galacturonan to give oligosaccharides with 4-deoxy-alpha-D-galact-4-enuronosyl groups at their non-reducing ends. In certain instances, Poly(beta-D-mannuronate) lyase (EC 4.2.2.3) is an enzyme that catalyzes the eliminative cleavage of polysaccharides containing beta-D-mannuronate residues to give oligosaccharides with 4-deoxy-alpha-L-erythro-hex-4-enopyranuronosyl groups at their ends. In some instances, Chondroitin ABC lyase (EC 4.2.2.4) is an enzyme that catalyzes the eliminative degradation of polysaccharides containing 1,4-beta-D-hexosaminyl and 1,3-beta-D-glucuronosyl linkages to disaccharides containing 4-deoxy-beta-D-gluc-4-enuronosyl groups. In some instances, Chondroitin ABC lyase (EC 4.2.2.4) also catalyzes the eliminative cleavage of dermatan sulfate containing 1,4-beta-D-hexosaminyl and 1,3-beta-D-glucurosonyl or 1,3-alpha-L-iduronosyl linkages to disaccharides containing 4-deoxy-beta-D-gluc-4-enuronosyl groups to yield a 4,5-unsaturated dermatan-sulfate disaccharide (deltaUA-GalNAc-4S). In certain instances, Chondroitin AC lyase (EC 4.2.2.5) is an enzyme that catalyzes the eliminative degradation of polysaccharides containing 1,4-beta-D-hexosaminyl and 1,3-beta-D-glucuronosyl linkages to disaccharides containing 4-deoxy-beta-D-gluc-4-enuronosyl groups. In some instances, Oligogalacturonide lyase (EC 4.2.2.6) is an enzyme that catalyzes the cleavage of 4-(4-deoxy-beta-D-gluc-4-enuronosyl)-D-galacturonate into 2 5-dehydro-4-deoxy-D-glucuronate. In certain instances, Heparin lyase (EC 4.2.2.7) is an enzyme that catalyzes the eliminative cleavage of polysaccharides containing 1,4-linked D-glucuronate or L-iduronate residues and 1,4-alpha-linked 2-sulfoamino-2-deoxy-6-sulfo-D-glucose residues to give oligosaccharides with terminal 4-deoxy-alpha-D-gluc-4-enuronosyl groups at their non-reducing ends. In some instances, Heparin lyase (EC 4.2.2.7) tolerates alternative sulfation of the substrate. In some instances, Heparin-sulfate lyase (EC 4.2.2.8) is an enzyme that catalyzes the eliminative cleavage of polysaccharides containing 1,4-linked D-glucuronate or L-iduronate residues and 1,4-alpha-linked 2-sulfoamino-2-deoxy-6-sulfo-D-glucose residues to give oligosaccharides with terminal 4-deoxy-alpha-D-gluc-4-enuronosyl groups at their non-reducing ends. In some instances, Heparin-sulfate lyase (EC 4.2.2.8) tolerates alternative sulfation of the substrate. In certain instances, Pectate disaccharide-lyase (EC 4.2.2.9) is an enzyme that catalyzes the eliminative cleavage of 4-(4-deoxy-alpha-D-galact-4-enuronosyl)-D-galacturonate from the reducing end of pectate, i.e. de-esterified pectin. In some instances, Pectin lyase (EC 4.2.2.10) is an enzyme that catalyzes the eliminative cleavage of (1->4)-alpha-D-galacturonan methyl ester to give oligosaccharides with 4-deoxy-6-O-methyl-alpha-D-galact-4-enuronosyl groups at their non-reducing ends. In certain instances, Poly(alpha-L-guluronate) lyase (EC 4.2.2.11) is an enzyme that catalyzes the eliminative cleavage of polysaccharides containing a terminal alpha-L-guluronate group, to give oligosaccharides with 4-deoxy-alpha-L-erythro-hex-4-enuronosyl groups at their non-reducing ends. In some instances, Xanthan lyase (EC 4.2.2.12) is an enzyme that catalyzes the cleavage of the beta-D-mannosyl-beta-D-1,4-glucuronosyl bond on the polysaccharide xanthan. In certain instances, Exo-(1->4)-alpha-D-glucan lyase (E.C. 4.2.2.13) is an enzyme that catalyzes the sequential degradation of (1->4)-alpha-D-glucans from the non-reducing end with the release of 1,5-anhydro-D-fructose. In some instances, Glucuronan lyase (EC 4.2.2.14) is an enzyme that catalyzes the eliminative cleavage of (1->4)-beta-D-glucuronans. This produces either oligosaccharides with 4-deoxy-beta-D-gluc-4-enuronosyl groups at their non-reducing ends, or, if the substrate is completely degraded, glucuronans produce tetrasaccharides. In certain instances, Anhydrosialidase (EC 4.2.2.15) is an enzyme that catalyzes the elimination of alpha-sialyl groups in N-acetylneuraminic acid glycosides, releasing 2,7-anhydro-alpha-N-acetylneuraminate. In some instances, Levan fructotransferase (DFA-IV-forming) (EC 4.2.2.16) is an enzyme that produces di-beta-D-fructofuranose 2,6':2',6-dianhydride (DFA IV) by successively eliminating the diminishing (2->6)-beta-D-fructan (levan) chain from the terminal D-fructosyl-D-fructosyl disaccharide. In certain instances, Inulin fructotransferase (DFA-I-forming) (EC 4.2.2.17) is an enzyme that produces alpha-D-fructofuranose beta-D-fructofuranose 1,2':2,1'-dianhydride (DFA I) by successively eliminating the diminishing (2->1)-beta-D-fructan (inulin) chain from the terminal D-fructosyl-D-fructosyl disaccharide. In some instances, Inulin fructotransferase (DFA-III-forming) (EC 4.2.2.18) is an enzyme that produces alpha-D-fructofuranose beta-D-fructofuranose 1,2':2,3'-dianhydride (DFA III) by successively eliminating the diminishing (2->1)-beta-D-fructan (inulin) chain from the terminal D-fructosyl-D-fructosyl disaccharide. In certain instances, Chondroitin B lyase (EC 4.2.2.19) is an enzyme that catalyzes the eliminative cleavage of dermatan sulfate containing 1,4-beta-D-hexosaminyl and 1,3-beta-D-glucurosonyl or 1,3-alpha-L-iduronosyl linkages to disaccharides containing 4-deoxy-beta-D-gluc-4-enuronosyl groups to yield a 4,5-unsaturated dermatan-sulfate disaccharide (deltaUA-GalNAc-4S). Any other suitable enzyme is also optionally utilized. For example, any keratanase may be used, e.g., as isolated from bacteria or evolved/designed from a related lyase.

In some embodiments, the analytical process comprises detecting and/or measuring the one or more oligosaccharide present in the biological sample after it has been treated with one or more glycosaminoglycan lyase. In some embodiments, the one or more oligosaccharide detected and/or measured is one or more disaccharide and/or one or more trisaccharide. In certain embodiments, the one or more oligosaccharides detected and/or measured (e.g., one or more disaccharide and/or one or more trisaccharide) are saturated at 4 and 5 carbons of the non-reducing end saccharide residue. In some embodiments, the non-reducing end residue of the one or more oligosaccharides detected and/or measured (e.g., one or more disaccharide and/or one or more trisaccharide) are free of carbon-carbon unsaturation. In certain embodiments, the one or more oligosaccharides detected and/or measured (e.g., one or more disaccharide and/or one or more trisaccharide) are free of carbon-carbon unsaturation. Biological samples suitable for analysis according to the methods and processes described herein include, by way of non-limiting example, blood, serum, urine, hair, saliva, skin, tissue, plasma, cerebrospinal fluid (CSF), amniotic fluid, nipple aspirate, sputum, feces, synovial fluid, nails, or the like. In specific embodiments, the biological samples suitable for analysis according to the methods and processes described herein include, by way of non-limiting example, urine, serum, plasma, or CSF. In certain embodiments, processes for detecting glycosoaminoglycans in a sample comprise providing, from the individual, a test biological sample that comprises glycosaminoglycans. In some embodiments, providing a test biological sample from an individual includes obtaining the sample from the individual or obtaining the sample from another source (e.g., from a technician or institution that obtained the sample from the individual). In some embodiments, the biological sample is obtained from any suitable source, e.g., any tissue or cell (e.g., urine, serum, plasma, or CSF) of an individual. In certain embodiments, the tissue and/or cell from which the GAGs are recovered is obtained from liver tissue or cells, brain tissue or cells, kidney tissue or cells, or the like.

FIG. 1 illustrates the cleavage of the glycosaminoglycan (GAG) heparan sulfate with a glycosaminoglycan lyase (heparinase II). As illustrated, in certain instances, internal cleavage of glycosaminoglycans with glycosaminoglycan lyases provides oligosaccharides with carbon-carbon unsaturation between the C4 and C5 carbons of the non-reducing end of the oligosaccharide produce (i.e., the newly created oligosaccharide). In some embodiments, the one or more oligosaccharide detected and/or measured according to a method described herein is one or more disaccharide and/or one or more trisaccharide, each oligosaccharide being is comprised of two or three saccharide residues that formed the original two or three saccharide residues of a glycosaminoglycan (GAG) prior to treatment with the one or more glycosaminoglycan (GAG) lyase.

In certain embodiments, analytical methods provided herein further comprise methods of purification. In certain embodiments, purification methods are performed prior to treating a biological sample with a lyase, as described herein. In some embodiments, purification methods are performed after treating a biological sample with a lyase, as described herein. In certain embodiments, purification methods are utilized before and after treating a biological sample with a lyase, as described herein. In some embodiments, purification methods include purifying one or more glycosaminoglycan and/or one or more oligosaccharide from other components (e.g., cells, cell parts, other polysaccharides, or the like) of the biological sample. In certain embodiments, purification methods include purifying one or more glycosaminoglycan from other polysaccharides (e.g., other glycans, other glycosaminoglycans, other sugars, or the like).

In certain instances the GAGs provided in a biological sample are present in lysosomes of cells. In some embodiments, any process described herein includes lysing a biological sample to free the GAGs from the cells therein.

Diagnostics

Provided in some embodiments herein is a process for diagnosing the identity and/or severity of abnormal glycosaminoglycan (or other glycan, e.g., glycolipid) accumulation in an individual, or a disorder thereof, the process comprising the step of: detecting the presence of and/or measuring the amount of a population of one or more oligosaccharides present in a transformed biological sample (e.g., urine, serum, plasma, or CSF). In certain embodiments, the process for diagnosing the identity and/or severity of abnormal glycosaminoglycan accumulation in an individual is a process of diagnosing the individual as an individual suffering from, homozygous for, or symptomatic for such a disorder. In other embodiments, the process for diagnosing the identity and/or severity of abnormal glycosaminoglycan accumulation in an individual is a process of diagnosing the individual as an individual suffering from such a disorder as a carrier for, or heterozygous for, such a disorder. In some embodiments, individuals that are carriers for, or heterozygous for, such a disorder has an elevated level of glycosaminoglycan accumulation (e.g., when compared to a normal individual), but the elevated level is less than an individual diagnosed with having the disorder. In certain embodiments, individuals that are carriers for, or heterozygous for, such a disorder has an elevated level of glycosaminoglycan accumulation (e.g., when compared to a normal individual), but are asymptomatic (including substantially asymptomatic) for a GAG accumulation disorder. Carriers and individuals having a GAG accumulation disease are identified utilizing any appropriate procedure. For example, in certain embodiments, carriers or carrier specimens may be identified as accumulating, e.g., 2-100 times more GAG than a non-carrier or wild type specimen. Similarly, in some exemplary embodiments, individuals that are symptomatic or have a GAG accumulation disease state accumulate more than 2 times more (e.g., 2-100×) GAG than a carrier. In some embodiments, diagnosis of one or more carrier parent is optionally utilized to make a progeny risk assessment (e.g., likelihood of a child being a carrier for or having a disease state).

In some embodiments, provided herein is a process for diagnosing abnormal glycosaminoglycan accumulation in an individual, or a disorder thereof, the process comprising the step of: using an analytical instrument to detect the presence of and/or measure the amount of a population of one or more oligosaccharides present in a transformed biological sample that has been prepared by treating a population of glycosaminoglycans, in or isolated from a biological sample from the individual, with at least one digesting glycosaminoglycan lyase to transform the glycosaminoglycans into the population of the one or more oligosaccharide. In specific embodiments, the oligosaccharide(s) detected or measured is one or more C4-C5 non-reducing end saturated oligosaccharide(s).

In some embodiments, provided herein is a process for diagnosing the identity (or type, e.g., heparan sulfate, chondroitin sulfate, or any other glycosaminoglycan) of abnormal glycosaminoglycan accumulation in an individual, or a disorder thereof, the process comprising the step of: using an analytical instrument to detect the presence of and/or measure the amount of a population of one or more oligosaccharides present in a transformed biological sample that has been prepared by treating a population of glycosaminoglycans, in or isolated from a biological sample from the individual, with at least one digesting glycosaminoglycan lyase to transform the glycosaminoglycans into the population of the one or more oligosaccharide. In specific embodiments, the oligosaccharide(s) detected or measured is one or more C4-C5 non-reducing end saturated oligosaccharide(s).

In some embodiments, provided herein is a process for diagnosing the severity of abnormal glycosaminoglycan accumulation in an individual, or a disorder thereof, the process comprising the step of: using an analytical instrument to detect the presence of and/or measure the amount of a population of one or more oligosaccharides present in a transformed biological sample that has been prepared by treating a population of glycosaminoglycans, in or isolated from a biological sample from the individual, with at least one digesting glycosaminoglycan lyase to transform the glycosaminoglycans into the population of the one or more oligosaccharide. In specific embodiments, the oligosaccharide(s) detected or measured is one or more C4-C5 non-reducing end saturated oligosaccharide(s).

In some embodiments, provided herein is a process for diagnosing an individual as being a carrier of a gene that causes abnormal glycosaminoglycan accumulation in an individual, or a disorder thereof, the process comprising the step of: using an analytical instrument to detect the presence of and/or measure the amount of a population of one or more oligosaccharides present in a transformed biological sample that has been prepared by treating a population of glycosaminoglycans, in or isolated from a biological sample from the individual, with at least one digesting glycosaminoglycan lyase to transform the glycosaminoglycans into the population of the one or more oligosaccharide. In certain instances, such a process involves determining the severity of abnormal glycosaminoglycan accumulation, wherein such accumulation is below a certain threshold (e.g., a predetermined level, a level whereby the individual becomes symptomatic, or the like). In specific embodiments, the oligosaccharide(s) detected or measured is one or more C4-C5 non-reducing end saturated oligosaccharide(s).

In some embodiments, provided herein is a process for diagnosing abnormal glycosaminoglycan accumulation in a human infant (e.g., a newborn) or fetus, or a disorder thereof, the process comprising the step of: using an analytical instrument to detect the presence of and/or measure the amount of a population of one or more oligosaccharides present in a transformed biological sample that has been prepared by treating a population of glycosaminoglycans, in or isolated from a biological sample from the individual, with at least one digesting glycosaminoglycan lyase to transform the glycosaminoglycans into the population of the one or more oligosaccharide. In specific embodiments, the oligosaccharide(s) detected or measured is one or more C4-C5 non-reducing end saturated oligosaccharide(s).

In further embodiments, any of the processes described herein further comprise the step of displaying or recording the presence of or a measure of a population of one or more oligosaccharide. The display may be on a computer screen or a paper print out. The recording may be on any computer readable disk (e.g., a hard drive, CD, DVD, portable memory device, such as a CF device or SD device, or the like), a sheet of paper, or the like.

In some embodiments, the transformed biological sample is prepared by treating a population of glycosaminoglycans or other glycan (e.g., glycolipid), the glycosaminoglycans or other glycan (e.g., glycolipid) being present in or isolated from a biological sample (e.g., urine, serum, plasma, or CSF) from an individual. Diagnostics, methods and compositions of matter described herein when referring to a GAG in general or a specific GAG, e.g., heparan sulfate, is understood to contain disclosure for any suitable glycan (e.g., a glycolipid). In certain embodiments, the glycosaminoglycans are treated with at least one agent suitable for cleaving bonds between saccharide residues of glycosaminoglycans. In some embodiments, a process described herein comprises transforming a biological sample by treating a population of glycosaminoglycans, the glycosaminoglycans being present in or isolated from a biological sample from an individual. In certain embodiments, the glycosaminoglycans are treated with at least one agent suitable for cleaving bonds between saccharide residues of glycosaminoglycans. In specific embodiments, treating a biological sample that comprises glycosaminoglycans with at least one agent suitable for cleaving bonds between saccharide residues of glycosaminoglycans comprises treating the biological sample with one or more digesting glycosaminoglycan (GAG) lyase. In some embodiments, the one or more digesting glycosaminoglycan lyase is one or more heparin lyase, one or more chondroitinase, one or more keratanase, one or more hyaluronidase, or a combination thereof. In certain embodiments, treatment of the glycosaminoglycan with the lyase provides to transform the glycosaminoglycans into the population of the one or more oligosaccharide. In specific embodiments, the at least one digesting glycosaminoglycan lyase is one or more heparin lyase.

In certain embodiments, the abnormal glycosaminoglycan accumulation comprises abnormal heparan sulfate accumulation, abnormal chondroitin sulfate accumulation, abnormal keratan sulfate accumulation, abnormal hyaluronan accumulation, abnormal dermatan sulfate accumulation, or a combination thereof. In some embodiments, disorders associated with abnormal glycosaminoglycan accumulation include lysosomal storage diseases, such as, by way of non-limiting example, mucopolysaccharidosis (MPS) (e.g., MPS I, MPS II, MPS IIIA, MPS IIIB, MPS IIIC, MPS IIID, MPS IVA, MPS IVB, MPS VI, MPS VII, MPS IX, or the like). In some embodiments, the process of diagnosing the identity of or the severity of a disorder associated with the accumulation of glycosaminoglycans is a disorder associated with abnormal heparan sulfate accumulation. In specific embodiments, disorders associated with abnormal heparan sulfate accumulation include, by way of non-limiting example, MPS I, MPS II, MPS IIIA, MPS IIIB, MPS IIIC, MPS IIID, MPS VII, or the like. In some embodiments, the process of diagnosing the identity of or the severity of a disorder associated with the accumulation of glycosaminoglycans is a disorder associated with abnormal dermatan sulfate accumulation (e.g., in some instances, MPS I, MPS II, MPS VI, or the like). In certain embodiments, the process of diagnosing the identity of or the severity of a disorder associated with the accumulation of glycosaminoglycans is a disorder associated with abnormal chondroitin sulfate accumulation (e.g., in some instances, MPS VI, MPS VII, or the like). In some embodiments, the process of diagnosing the identity of or the severity of a disorder associated with the accumulation of glycosaminoglycans is a disorder associated with abnormal keratan sulfate accumulation (e.g., in some instances, MPS IVA, MPS IVB, or the like). In certain embodiments, the process of diagnosing the identity of or the severity of a disorder associated with the accumulation of glycosaminoglycans is a disorder associated with abnormal hyaluronan accumulation (e.g., in some instances, MPS VII, MPS IX, or the like). In some embodiments, oligosaccharides provided by treating the glycosaminoglycan with a suitable glycosaminoglycan lyase are utilized in processes described herein to diagnose the identity of and/or measure the severity of a disorder associated with the abnormal accumulation of the particular glycosaminoglycan. Specific oligosaccharides provided by treating various glycosaminoglycans with glycosaminoglycan lyases are provided herein in the oligosaccharide section.

Moreover, in certain embodiments, the diagnostic methods described herein (or other method described herein) are suitable for diagnosing (or measuring the efficacy of a treatment of) a disorder in an individual involved with glycan (e.g., GAG) accumulation or any disorder involved with altered GAG synthesis and degradation (e.g., any disorder that provides a unique GAG or population of GAGs that can be detected by a process described herein). In some embodiments, such a disease includes Alzheimer's Disease, wherein GAGs are present in plaques, and a biological sample is taken from the plaque and analyzed according to a process described herein. In other embodiments, such a disease includes cancer.

In some embodiments, specific oligosaccharides are detected and/or measured according to methods and/or processes described herein to diagnose the identity and/or severity of a specific disorder associated with glycosaminoglycan accumulation. In some embodiments, such oligosaccharides are described herein. In specific embodiments, a process for diagnosing the identity or severity of a disorder associated with the accumulation of glycosaminoglycans provided herein comprises detecting and/or measuring one or more oligosaccharide set forth in Formulas I-XX or any other oligosaccharide described in the figures. In certain embodiments, the one or more oligosaccharides detected and/or measured are free of carbon-carbon unsaturation. In some embodiments, the one or more oligosaccharides detected and/or measured are free of C4 and C5 carbon unsaturation on the saccharide residue at the non-reducing end of the oligosaccharide. In some embodiments, the oligosaccharide of any of Formulas I-XX is a disaccharide or trisaccharide comprised of two or three saccharide residues that formed the original two or three saccharide residues of a glycosaminoglycan (GAG) prior to treatment with the one or more glycosaminoglycan (GAG) lyase. In certain instances, the amount of disaccharide or trisaccharide of any of Formulas I-XX free of non-reducing end carbon-carbon (e.g., C4/C5) is representative of the amount of accumulated glycosaminoglycans comprising the same disaccharide or trisaccharide as residue thereof, at its non-reducing end.

Figure 2:
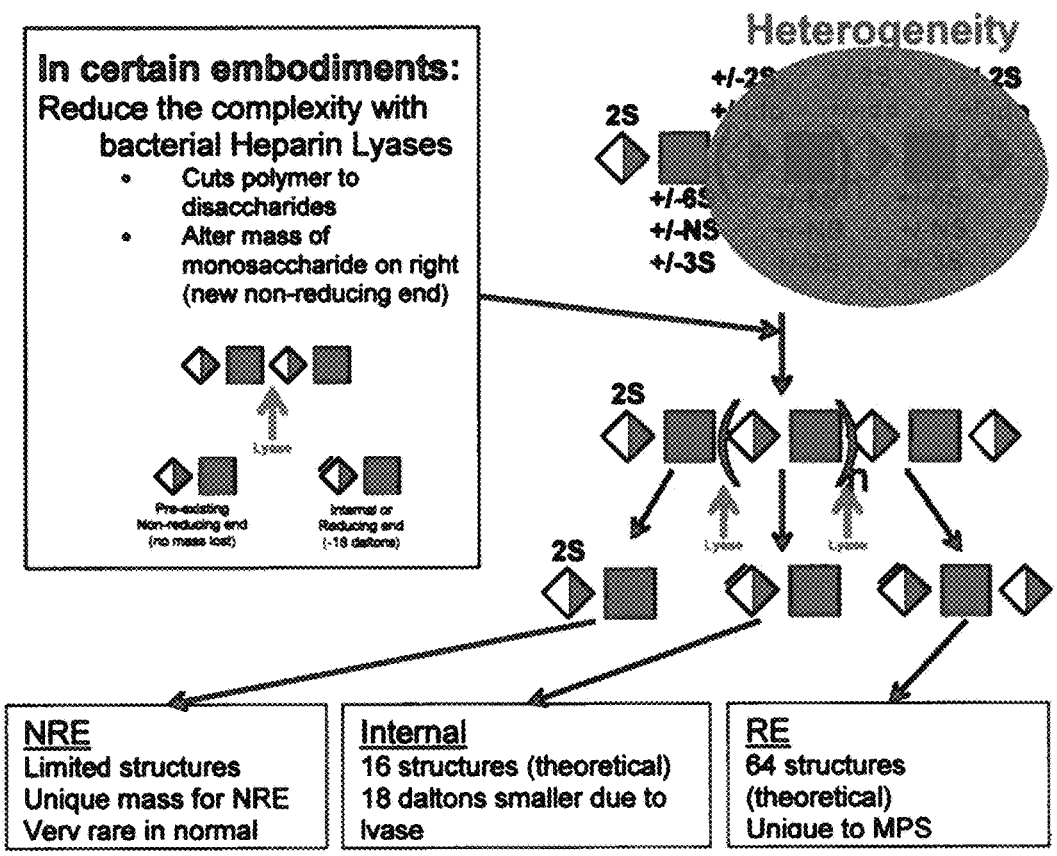
FIG. 2 illustrates lyase liberation of three classes of di- and trisaccharides from normal and MPS GAGs. The non-reducing end (NRE) fragments are used as biomarkers in certain embodiments herein.
Figure 3A:
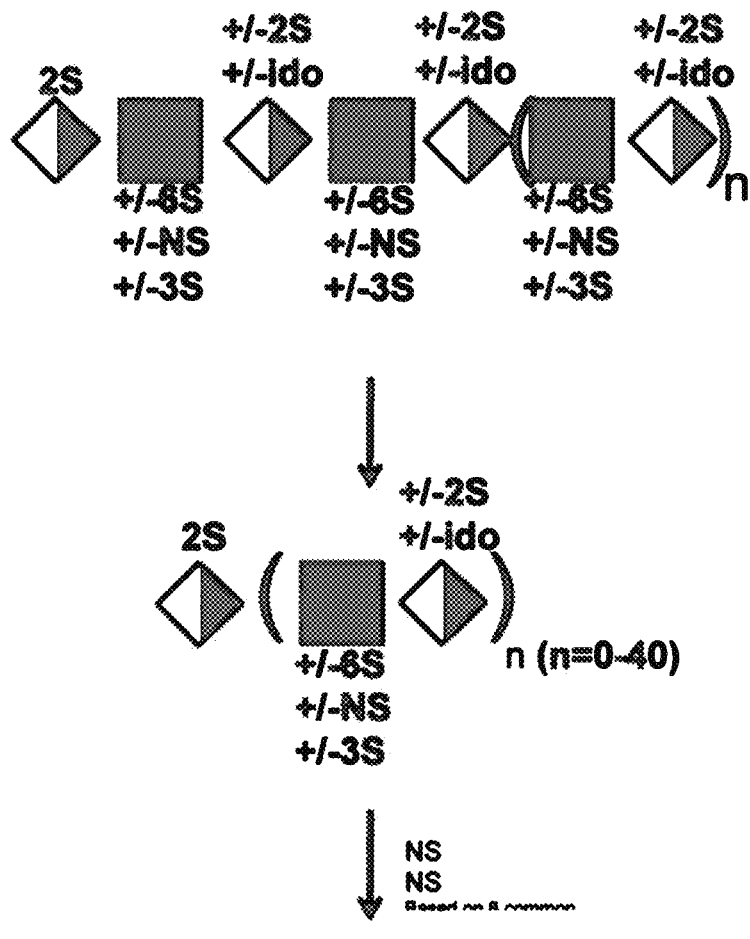
Figure 3C:
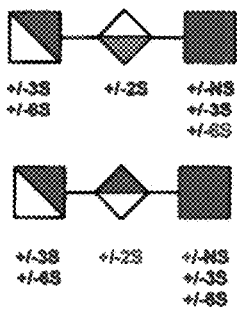

In certain instances, a diagnostic method described herein is useful for analyzing the various different classes of MPS. In some instances, the GAG accumulation provides a unique population of GAGs depending on the specific MPS class. In specific instance, the unique population of GAGs can be identified as being correlated with a specific MPS class by detecting and/or measuring oligosaccharides in a sample taken from an individual diagnosed with or suspected of having an MPS disorder, the oligosaccharides being free of C4 and C5 carbon unsaturation on the saccharide residue at the non-reducing end of the oligosaccharide. In certain instances, the oligosaccharides are digested with a suitable enzyme, such as a lyase (e.g., a bacterial lyase or heparin lyase) prior to detection/measurement and the resulting oligosaccharide (shorter in certain instances than the sample oligosaccharide, such as di- or tri-saccharides) are detected/measured. In certain instances, the degradation enzymes (e.g., heparin lyase) work by an eliminase mechanism which introduces an unsaturated bond on the newly generated non-reducing end; whereas preexisting non-reducing ends retain their full mass (e.g., these non-reducing ends are free of C4 and C5 carbon unsaturation). Thus in certain embodiments, the digested oligosaccharides comprising non-reducing ends that are free of C4 and C5 carbon unsaturation are representative of the total number of oligosaccharides present in the original sample composition. In certain instances, the mechanism of digesting (e.g., with a heparin lyase) effectively tags the preexisting ends to allow for their identification by their unique mass (e.g., being 18 Daltons larger than the other oligosaccharides provided by internal oligosaccharide residues). In some instances, identification of these preexisting non-reducing ends are excellent biomarkers because, e.g., in certain instances (1) they are homogenous within an MPS class (e.g., in certain instances for MPS II, they all end in 2-0 sulfated uronic acid); (2) there are many more non-reducing ends in GAGs from individuals suffering from MPS than in non-MPS individuals); and/or (3) in non-MPS individuals the non-reducing end saccharide residues are heterogeneous (see, e.g., FIG. 2). FIG. 3A illustrates the large number of oligosaccharide residues found within GAGs and FIGS. 3B and 3C summarize the predicted non-reducing end heparan sulfate oligosaccharide residues (e.g., the biomarkers) for 7 MPS classes. In some embodiments, any one or more of these oligosaccharides are detected and/or measured in a method of diagnosing an individual suffering from the specific MPS class described. In some embodiments, additional biomarkers for these MPS classes that originate from chondroitin and dermatan can also be analyzed using the same method. The same approach (using chondroitinase, keratanase, and hyaluronidases) is provided for in certain embodiments for other MPS classes that accumulate CS, DS, KS, and/or HA.

In certain embodiments, a process for diagnosing the identity or severity of a disorder associated with the accumulation of glycosaminoglycans provided herein comprises detecting and/or measuring one or more oligosaccharide set forth in Formulas XXI-XXIX or in any of the figures described herein. In certain embodiments, the one or more oligosaccharides detected and/or measured comprise at least one point of carbon-carbon unsaturation. In some embodiments, the one or more oligosaccharides detected and/or measured comprise C4 and C5 carbon unsaturation on the saccharide residue at the non-reducing end of the oligosaccharide.

In certain embodiments, processes described herein, including diagnostic processes, include preparing a transformed biological sample by purifying a population of oligosaccharides in a biological sample that has been treated with the at least one glycosaminoglycan lyase (e.g., one or more heparin lyase), the transformed biological sample comprising the isolated population of oligosaccharides. In some embodiments, glycosaminoglycans of the biological sample from an individual are purified prior to treatment with the one or more glycosaminoglycan lyase.

In some embodiments, a diagnositic (including identity or severity diagnostic) process provided herein comprises comparing a detection or measurement according to the process to a control reading. In some embodiments, the comparison to a control comprises comparing the amount of the population of one or more oligosaccharide present in the transformed biological sample to an amount of a population of the one or more oligosaccharide present in a control biological sample that has been treated in a manner substantially similar to the transformed biological sample. In specific embodiments, the control biological sample was provided from an individual that does not have a disorder associated with abnormal glycosaminoglycan accumulation (e.g., mucopolysaccharidosis (MPS)). In specific embodiments, the control biological sample was provided from an individual that has a disorder associated with abnormal glycosaminoglycan accumulation (e.g., mucopolysaccharidosis (MPS)). In more specific embodiments, the control is from an individual with an abnormal glycosaminoglycan accumulation selected from, by way of non-limiting example, MPS I, MPS II, MPS IIIA, MPS IIIB, MPS IIIC, MPS IIID, MPS IVA, MPS IVB, MPS VI, MPS VII, MPS IX, and a combination thereof (e.g., MPS I, MPS II, MPS IIIA, MPS IIIB, MPS IIIC, MPS IIID, MPS VII, and a combination thereof).

In some embodiments, detecting the presence of or measuring the amount of a population of one or more oligosaccharide present in a transformed biological sample according to a process described herein comprises:
  a. isolating a subpopulation of one or more oligosaccharides in the transformed biological sample (e.g., a transformed urine, serum, plasma, or CSF sample); and
  b. detecting the presence of and/or measuring the amount of one or more oligosaccharides present in the subpopulation.

Isolation of the subpopulation of one or more oligosaccharides in the transformed biological sample is achieved in any suitable manner, e.g., using a purification process described herein (e.g., chromatography, electrophoresis, filtration, centrifugation, etc.). Similarly, according to any process described herein, the detection of and/or measuring the presence of one or more oligosaccharide is achieved utilizing any suitable process, including those detection processes set forth herein (e.g., spectrometry, UV-Visible spectrometry, IR spectrometry, NMR spectrometry, mass spectrometry, or the like). In specific instances, prior to detecting and/or measuring the oligosaccharide present, any process described herein further comprises tagging the reducing end of a representative portion of the one or more oligosaccharides in the transformed biological sample with any suitable detectable label (e.g., a mass label, a radio label, a fluorescent label, a chromophore label, affinity label, etc.).

In certain embodiments, the detection of the presence and/or measure of the amount of oligosaccharide is performed utilizing an analytical instrument. In specific embodiments, the analytical device comprises a spectrometer that detects and/or measures the amount of a detectable label. In certain embodiments, the detection and/or measurement of amounts of a detectable label serves as a proxy to the presence or amounts of GAGs present. In more specific embodiments, the spectrometer includes, by way of non-limiting example, one or more of a mass spectrometer, a nuclear magnetic resonance spectrometer, a UV-Vis spectrometer, an IR spectrometer, a fluorimeter, a phosphorimeter, a radiation spectrometer, or the like. In certain embodiments, the analytical device comprises a purification device coupled to a detector or a measuring device (e.g., a HPLC system coupled to a UV-Vis spectrometer). In certain embodiments, an analytical device is a liquid chromatography mass spectrometer (LC-MS) that detects and/or measures the mass of an oligosaccharide.

In some embodiments, the presence detected and/or the measure of the population of the oligosaccharide is displayed or recorded. In some embodiments, the process comprises displaying or recording the results of the characterization. In certain embodiments, the results are displayed on a display monitor (e.g., a computer monitor, television, PDA, or the like), or print out. In some embodiments, the results are recorded on an electronic medium (e.g., a hard disk drive, magnetic storage drive, optical storage drive or the like; a disk such as a floppy disk, CD, DVD, BLU-ray or the like; a flash memory drive; removable drive or the like).

In certain embodiments, the individual is a mammal, e.g., a human. In some embodiments, the human is a newborn. In certain embodiments, the human is an embryo in utero. In some embodiments, the human has been diagnosed with a lysosomal storage disease. In some embodiments, the human is suspected of suffering from a lysosomal storage disease.

Analytical Samples

Provided in certain embodiments herein are compositions comprising any one or more oligosaccharides provided herein. In some embodiments, the composition provided herein is an analytical sample, suitable analysis in any analytical device, e.g., one provided herein (such as, by way of non-limiting example, high performance liquid chromatography, mass spectrometry, gas chromatography, or the like).

In certain embodiments, a composition provided herein comprises at least one disaccharide or trisaccharide from a transformed biological sample from an individual with a disorder associated with abnormal glycosaminoglycan accumulation. In specific embodiments, the transformed biological sample was prepared by treating a biological sample comprising glycosaminoglycans with one or more digesting glycosaminoglycan lyase.

In some embodiments, an analytical sample provided herein comprises one or more oligosaccharide of any of Formulas I to XX, any one of Formulas XXI to XXIX, or any of Formulas I to XXIX. In certain embodiments, an analytical sample provided herein comprises one or more oligosaccharide of any of Formulas I to XX, any one of Formulas XXI to XXIX, or any of Formulas I to XXIX, wherein the one or more oligosaccharides further comprise a detectable label attached (e.g., covalently and/or non-covalently) to the reducing end of the one or more oligosaccharide.

In some embodiments, provided herein is a composition comprising isolated glycans, wherein the glycans were isolated from a biological sample, and one or more glycan degradation enzyme. In certain embodiments, the composition further comprises one or more biomarker generated according to any method described herein (e.g., wherein the biomarker is a non-reducing saturated oligosaccharide). In certain embodiments, provided herein is an oligosaccharide described herein (e.g., a labeled or non-labeled non-reducing saturated oligosaccharide) and an analytical instrument or chromatographic resin.

Oligosaccharides

In certain embodiments, methods and processes described herein are utilized to detect and/or measure one or more biomarker. In specific embodiments, such biomarkers comprise one or more oligosaccharides (e.g., disaccharide(s) and/or trisaccharide(s)). In certain embodiments, the one or more oligosaccharides comprise any one or more of the oligosaccharides described herein.

As used herein, IdoA and  are iduronic acid (e.g., α-L-iduronic acid) saccharide residues. As used herein, GlcA and ♦ are glucuronic acid (e.g., β-L-glucuronic acid) saccharide residues. As used herein, ♦ is either an iduronic acid (e.g., α-L-iduronic acid) saccharide residue or a glucuronic acid (e.g., β-L-glucuronic acid) saccharide residue. As used herein, GlcN and ■ are glucosamine (e.g., 2-deoxy-2-amino-β-D-glucopyranosyl) saccharide residues. As used herein, GlcN(Ac)$_1$ and ■ are a glucosamine (e.g., 2-deoxy-2-amino-β-D-glucopyranosyl) saccharide residue wherein the 2-amino group is acetylated. As used herein, Gal and ○ is a galactose saccharide residue. As used herein GalNAc and ▨ represents an N-acetylgalactosamine residue. As used herein ■ and ■ both represent N-sulfated (i.e., N-substituted with SO$_3$R as described herein) glucosamine (e.g., 2-deoxy-2-amino-β-D-glucopyranosyl) saccharide residue. In various specific instances, iduronic acid, glucuronic acid, glucosamine, and/or galactose saccharide residues are saturated at 4 and 5 carbons of the non-reducing end saccharide residue, or are free of carbon-carbon unsaturation. In other instances, any one or more of the saccharide residues is unsaturated, e.g., at the 4 and 5 carbon positions of the saccharide residue at the non-reducing end of an oligosaccharide provided herein. The symbolic nomenclature used herein follows the "Symbol and Text Nomenclature for Representation of Glycan Structure" as promulgated by the Nomenclature Committee for the Consortium for Functional Glycomics, as amended on October 2007. Recitation of an NS (e.g., above of below any of the aforementioned structures) indicates that the amino group thereof is substituted with (SO$_3$R). If the NS is associated with GlcN (Ac)$_m$ or above or below ■, the residue is GlcN(SO$_3$R), wherein the amino group bears the (SO$_3$R). Recitation of a 2S (e.g., above or below any of the aforementioned structures) indicates that the hydroxyl group at the two carbon position of the indicated saccharide residue is substituted with (SO$_3$R). Recitation of a 3S (e.g., above of below any of the aforementioned structures) indicates that the hydroxyl group at the three carbon position of the indicated saccharide residue is substituted with (SO$_3$R). Recitation of a 4S (e.g., above of below any of the aforementioned structures) indicates that the hydroxyl group at the four carbon position of the indicated saccharide residue is substituted with (SO$_3$R). Recitation of a 6S (e.g., above of below any of the aforementioned structures) indicates that the hydroxyl group at the six carbon position of the indicated saccharide residue is substituted with (SO$_3$R).

In specific embodiments, methods and processes described herein are utilized to detect and/or measure an oligosaccharide (disaccharide) having the formula:

[IdoA-GlcN(Ac)$_m$](SO$_3$R)$_n$   Formula I

In certain embodiments, oligosaccharides described herein, e.g., those detected and/or measured according to the methods and/or processes described herein, are disaccharides of Formula I, wherein m is 0-1, and n is 0-3. As used herein, each R is independently H or a negative charge. The disaccharide is optionally sulfated with n SO$_3$R groups in any suitable location. In more specific embodiments, a disaccharide of Formula I has a structure of IdoA-GlcNAc, IdoA-GlcNS, IdoA-GlcNS6S, IdoA2S-GlcNAc, IdoA2S-GlcNS, IdoA2S-GlcNAc6S, IdoA2S-GlcNS6S or as set forth in any of Formulas I-A to I-G, as set forth in FIG. 4. In certain instances, compounds of Formulas I-A to I-G are provided by treating the glycosaminoglycan heparan sulfate with a suitable glycosaminoglycan lyase.

In some embodiments, the detection and/or measurement of any one or more disaccharide of Formulas I-A to I-C is utilized in a process for diagnosing MPS I. In certain embodiments, the detection and/or measurement of any one or more disaccharide of Formulas I-D to I-G is utilized in a process for diagnosing MPS II.

In certain embodiments, methods and processes described herein are utilized to detect and/or measure an oligosaccharide (trisaccharide) having the formula:

[GlcN(Ac)$_m$-(IdoA/GlcA)-GlcN(Ac)$_n$](SO$_3$R)$_p$   Formula II

In certain embodiments, oligosaccharides described herein, e.g., those detected and/or measured according to the methods and/or processes described herein, are trisaccharides of Formula II, wherein IdoA/GlcA is either IdoA or GlcA, m is 0-1, n is 0-1, and p is 0-5. The trisaccharide is optionally sulfated with p SO$_3$R groups in any suitable location.

In some specific embodiments, a compound of Formula II has a structure as set forth in Formula III:

[GlcNS-IdoA-GlcN(Ac)$_n$](SO$_3$R)$_p$   Formula III

Figure 5:
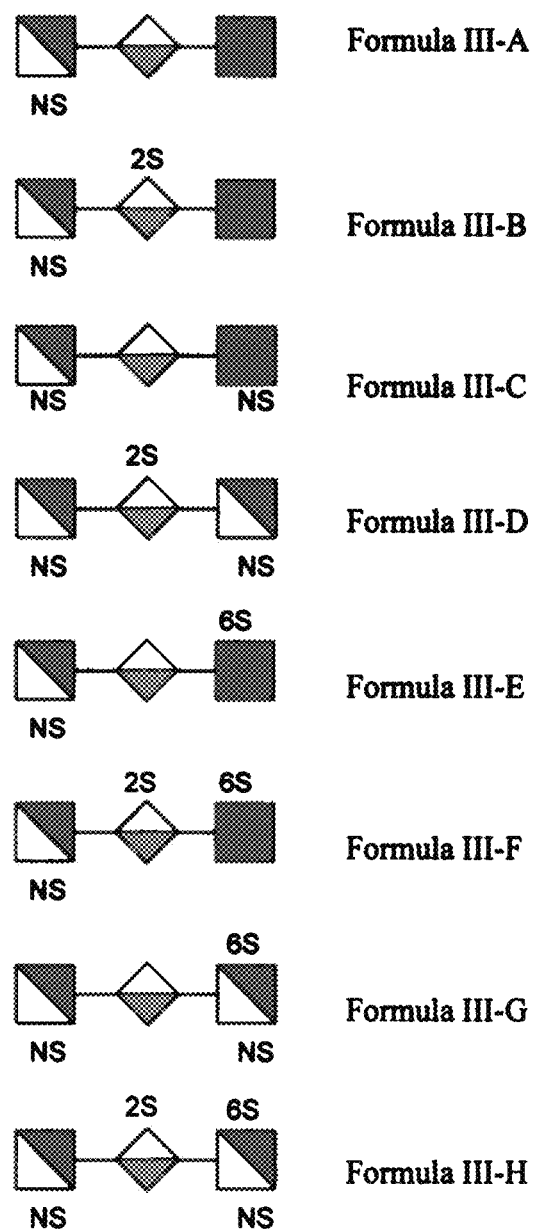
FIG. 5 illustrates oligosaccharides of Formula III.

In certain embodiments, oligosaccharides described herein, e.g., those detected and/or measured according to the methods and/or processes described herein, are trisaccharides of Formula III, wherein n is 0-1, and p is 0-3. The trisaccharide is optionally sulfated with p SO$_3$R groups in any suitable location. In more specific embodiments, a trisaccharide of Formula III has a structure of GlcNS-IdoA-GlcNAc, GlcNS-IdoA2S-GlcNAc, GlcNS-IdoA-GlcNS, GlcNS-IdoA2S-GlcNS, GlcNS-IdoA-GlcNAc6S, GlcNS-IdoA2S-GlcNAc6S, GlcNS-IdoA-GlcNS6S, GlcNS-IdoA2S-GlcNS6S, or as set forth in any of the trisaccharides of FIG. 5. In certain instances, compounds of Formulas III-A to III-H are provided by treating the glycosaminoglycan heparan sulfate with a suitable glycosaminoglycan lyase.

In certain specific embodiments, a compound of Formula II has a structure as set forth in Formula IV:

[GlcNS-GlcA-GlcN(Ac)$_n$](SO$_3$R)$_p$   Formula IV

Figure 6:
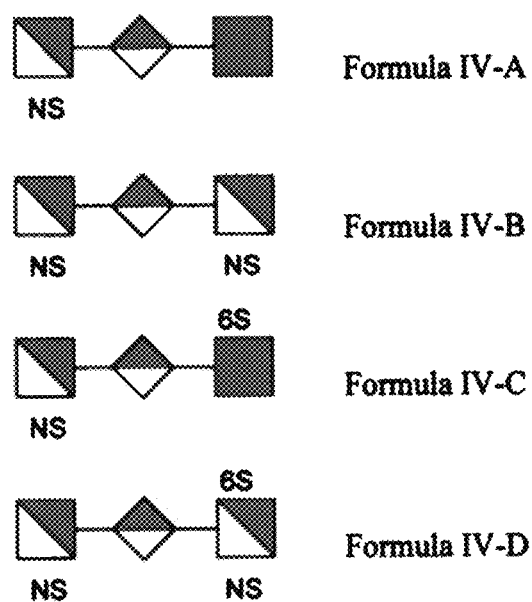
FIG. 6 illustrates oligosaccharides of Formula IV.

In certain embodiments, oligosaccharides described herein, e.g., those detected and/or measured according to the methods and/or processes described herein, are trisaccharides of Formula IV, wherein n is 0-1, and p is 0-2. The trisaccharide is optionally sulfated with p $SO_3R$ groups in any suitable location. In more specific embodiments, a trisaccharide of Formula IV has a structure of GlcNS-GlcA-GlcNAc, GlcNS-GlcA-GlcNS, GlcNS-GlcA-GlcNAc6S, GlcNS-GlcA-GlcNS6S or as set forth in any of the trisaccharides of FIG. 6. In certain instances, compounds of Formulas IV-A to IV-D are provided by treating the glycosaminoglycan heparan sulfate with a suitable glycosaminoglycan lyase.

In some embodiments, the detection and/or measurement of any one or more trisaccharide of Formulas III and/or IV is utilized in a process for diagnosing MPS IIIA.

In some specific embodiments, a compound of Formula II has a structure as set forth in Formula V:

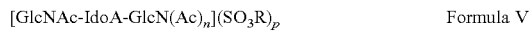

[GlcNAc-IdoA-GlcN(Ac)$_n$](SO$_3$R)$_p$        Formula V

Figure 7:
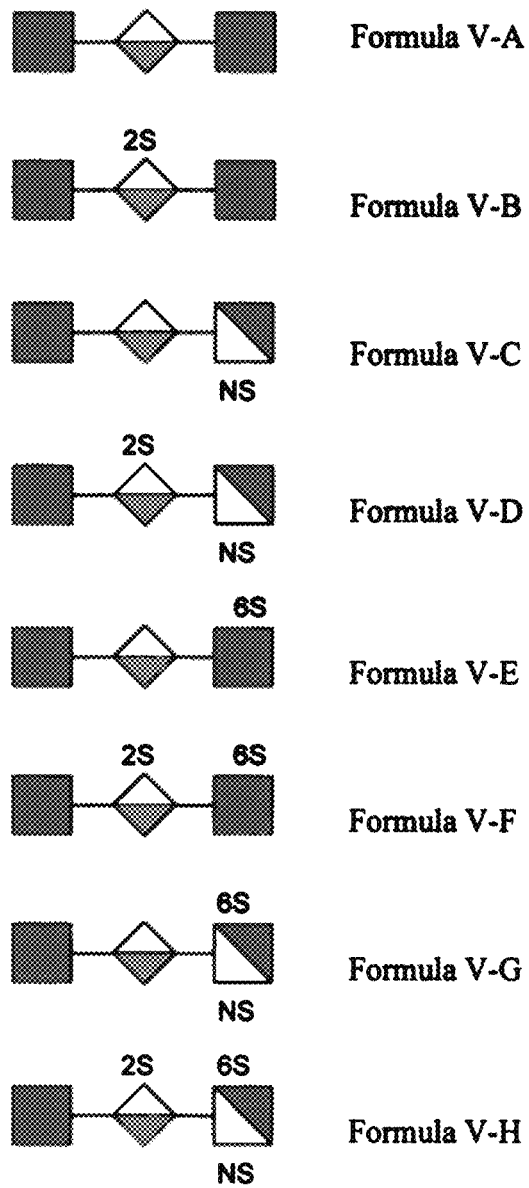
FIG. 7 illustrates oligosaccharides of Formula V.

In certain embodiments, oligosaccharides described herein, e.g., those detected and/or measured according to the methods and/or processes described herein, are trisaccharides of Formula V, wherein n is 0-1, and p is 0-3. The trisaccharide is optionally sulfated with p $SO_3R$ groups in any suitable location. In more specific embodiments, a trisaccharide of Formula V has a structure of GlcNAc-IdoA-GlcNAc, GlcNAc-IdoA2S-GlcNAc, GlcNAc-IdoA-GlcNS, GlcNAc-IdoA2S-GlcNS, GlcNAc-IdoA-GlcNAc6S, GlcNAc-IdoA2S-GlcNAc6S, GlcNAc-IdoA-GlcNS6S, GlcNAc-IdoA2S-GlcNS6, or as set forth in any of the trisaccharides of FIG. 7. In certain instances, compounds of Formulas V-A to V-H are provided by treating the glycosaminoglycan heparan sulfate with a suitable glycosaminoglycan lyase.

In certain specific embodiments, a compound of Formula II has a structure as set forth in Formula VI:

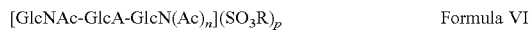

[GlcNAc-GlcA-GlcN(Ac)$_n$](SO$_3$R)$_p$        Formula VI

Figure 8:
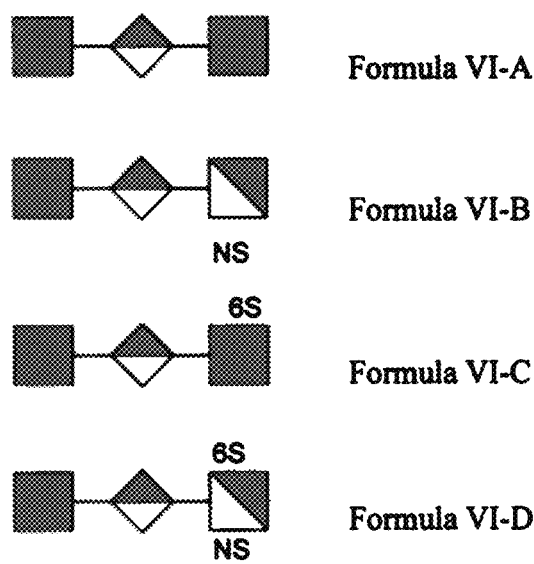
FIG. 8 illustrates oligosaccharides of Formula VI.

In certain embodiments, oligosaccharides described herein, e.g., those detected and/or measured according to the methods and/or processes described herein, are trisaccharides of Formula VI, wherein n is 0-1, and p is 0-2. The trisaccharide is optionally sulfated with p $SO_3R$ groups in any suitable location. In more specific embodiments, a trisaccharide of Formula VI has a structure of GlcNAc-GlcA-GlcNAc, GlcNAc-GlcA-GlcNS, GlcNAc-GlcA-GlcNAc6S, GlcNAc-GlcA-GlcNS6S or as set forth in any of the trisaccharides of FIG. 8. In certain instances, compounds of Formulas VI-A to VI-D are provided by treating the glycosaminoglycan heparan sulfate with a suitable glycosaminoglycan lyase.

In some embodiments, the detection and/or measurement of any one or more trisaccharide of Formulas V and/or VI is utilized in a process for diagnosing MPS IIIB.

In some specific embodiments, a compound of Formula II has a structure as set forth in Formula VII:

[GlcN-Ido-GlcN(Ac)$_n$](SO$_3$R)$_p$        Formula VII

Figure 9:
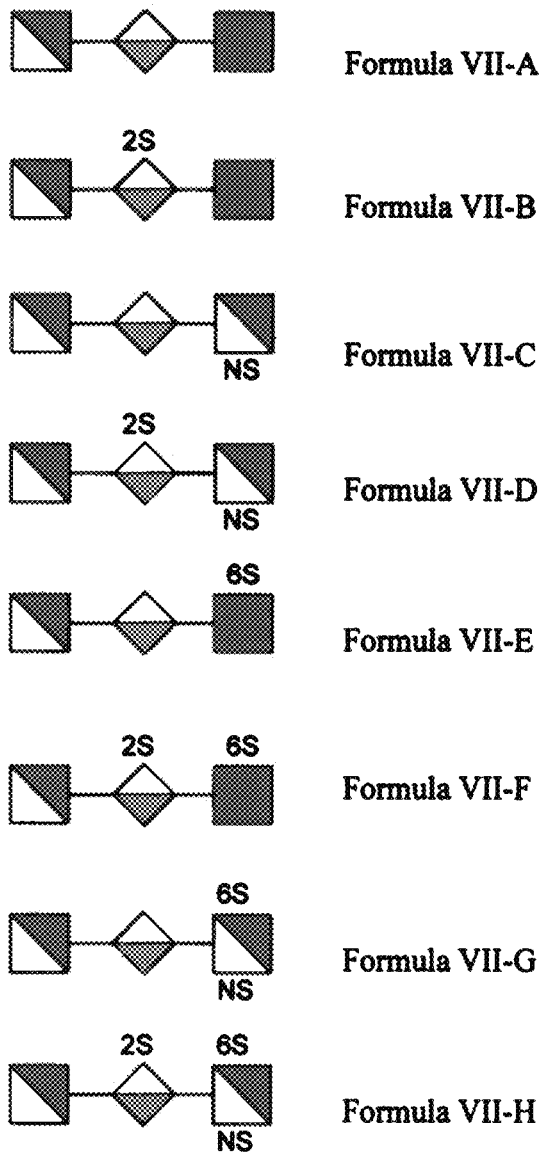
FIG. 9 illustrates oligosaccharides of Formula VII.

In certain embodiments, oligosaccharides described herein, e.g., those detected and/or measured according to the methods and/or processes described herein, are trisaccharides of Formula VII, wherein n is 0-1, and p is 0-4. The trisaccharide is optionally sulfated with p $SO_3R$ groups in any suitable location. In more specific embodiments, a trisaccharide of Formula VII has a structure of GlcN-IdoA-GlcNAc, GlcN-IdoA2S-GlcNAc, GlcN-IdoA-GlcNS, GlcN-IdoA2S-GlcNS, GlcN-IdoA-GlcNAc6S, GlcN-IdoA2S-GlcNAc6S, GlcN-IdoA-GlcNS6S, GlcN-IdoA2S-GlcNS6S, or as set forth in any of the trisaccharides of FIG. 9. In certain instances, compounds of Formulas VII-A to VII-H are provided by treating the glycosaminoglycan heparan sulfate with a suitable glycosaminoglycan lyase.

In certain specific embodiments, a compound of Formula II has a structure as set forth in Formula VIII:

[GlcN-GlcA-GlcN(Ac)$_n$](SO$_3$R)$_p$        Formula VIII

Figure 10:
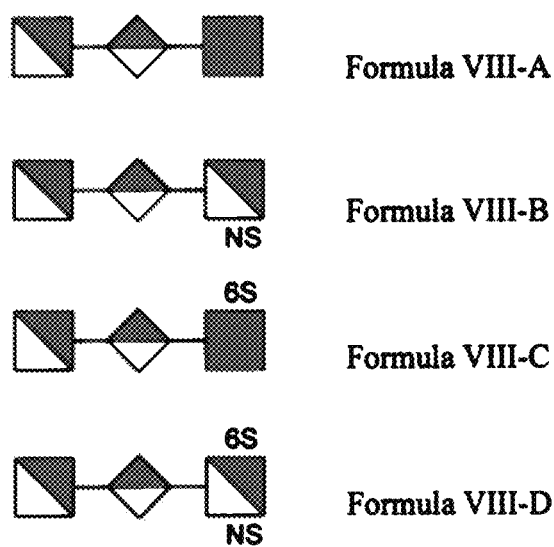
FIG. 10 illustrates oligosaccharides of Formula VIII.

In certain embodiments, oligosaccharides described herein, e.g., those detected and/or measured according to the methods and/or processes described herein, are trisaccharides of Formula VIII, wherein n is 0-1, and p is 0-4. The trisaccharide is optionally sulfated with p $SO_3R$ groups in any suitable location. In more specific embodiments, a trisaccharide of Formula VIII has a structure of GlcN-GlcA-GlcNAc, GlcN-GlcA-GlcNS, GlcN-GlcA-GlcNAc6S, GlcN-GlcA-GlcNS6S, or as set forth in any of the trisaccharides of FIG. 10. In certain instances, compounds of Formulas VIII-A to VIII-D are provided by treating the glycosaminoglycan heparan sulfate with a suitable glycosaminoglycan lyase.

In some embodiments, the detection and/or measurement of any one or more trisaccharide of Formulas VII and/or VIII is utilized in a process for diagnosing MPS IIIC.

In some specific embodiments, a compound of Formula II has a structure as set forth in Formula IX:

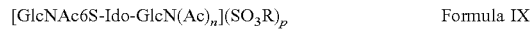

[GlcNAc6S-Ido-GlcN(Ac)$_n$](SO$_3$R)$_p$        Formula IX

Figure 11:
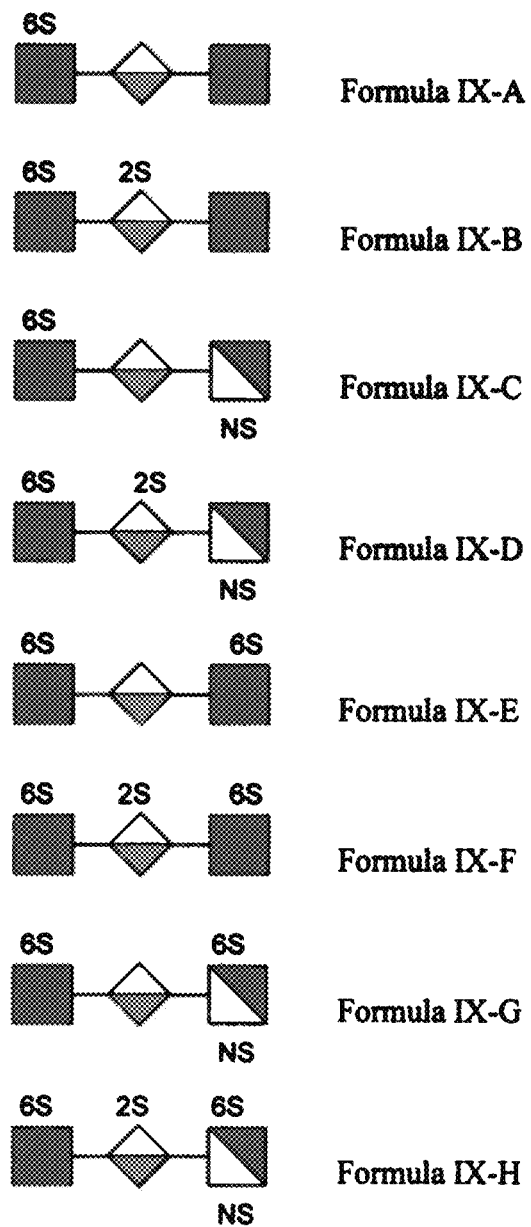
FIG. 11 illustrates oligosaccharides of Formula IX.

In certain embodiments, oligosaccharides described herein, e.g., those detected and/or measured according to the methods and/or processes described herein, are trisaccharides of Formula IX, wherein n is 0-1, and p is 0-3. The trisaccharide is optionally sulfated with p $SO_3R$ groups in any suitable location. In more specific embodiments, a trisaccharide of Formula VII has a structure of GlcNAc6S-IdoA-GlcNAc, GlcNAc6S-IdoA2S-GlcNAc, GlcNAc6S-IdoA-GlcNS, GlcNAc6S-IdoA2S-GlcNS, GlcNAc6S-IdoA-GlcNAc6S, GlcNAc6S-IdoA2S-GlcNAc6S, GlcNAc6S-IdoA-GlcNS6S, GlcNAc6S-IdoA2S-GlcNS6S, or as set forth in any of the trisaccharides of FIG. 11. In certain instances, compounds of Formulas IX-A to IX-H are provided by treating the glycosaminoglycan heparan sulfate with a suitable glycosaminoglycan lyase.

In certain specific embodiments, a compound of Formula II has a structure as set forth in Formula X:

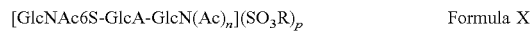

[GlcNAc6S-GlcA-GlcN(Ac)$_n$](SO$_3$R)$_p$        Formula X

Figure 12:
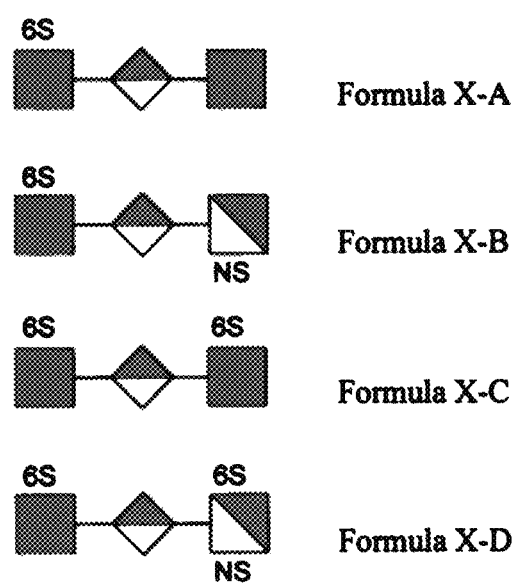
FIG. 12 illustrates oligosaccharides of Formula X.

In certain embodiments, oligosaccharides described herein, e.g., those detected and/or measured according to the methods and/or processes described herein, are trisaccharides of Formula X, wherein n is 0-1, and p is 0-2. The trisaccharide is optionally sulfated with p $SO_3R$ groups in any suitable location. In more specific embodiments, a trisaccharide of Formula X has a structure of GlcNAc6S-GlcA-GlcNAc, GlcNAc6S-GlcA-GlcNS, GlcNAc6S-GlcA-GlcNAc6S, GlcNAc6S-GlcA-GlcNS6S, or as set forth in any of the trisaccharides of FIG. 12. In certain instances, compounds of Formulas X-A to X-D are provided by treating the glycosaminoglycan heparan sulfate with a suitable glycosaminoglycan lyase.

In some embodiments, the detection and/or measurement of any one or more trisaccharide of Formulas IX and/or X is utilized in a process for diagnosing MPS IIID.

In certain embodiments, methods and processes described herein are utilized to detect and/or measure an oligosaccharide (disaccharide) having the formula:

[GlcA-GlcN(Ac)$_m$](SO$_3$R)$_n$        Formula XI

In certain embodiments, oligosaccharides described herein, e.g., those detected and/or measured according to the methods and/or processes described herein, are disaccharides of Formula XI, wherein m is 0-1, and n is 0-2. The disaccharide is optionally sulfated with n SO₃R groups in any suitable location. In more specific embodiments, a disaccharide of Formula XI has a structure of GlcA-GlcNAc, GlcA-GlcNAc 6S, GlcA-GlcNS, GlcA-GlcNS6S, or as set forth in any of the disaccharides of FIG. 13. In certain instances, compounds of Formulas XI-A to XI-D are provided by treating the glycosaminoglycan heparan sulfate with a suitable glycosaminoglycan lyase.

In some embodiments, the detection and/or measurement of any one or more disaccharide of Formula XI is utilized in a process for diagnosing MPS VII.

In certain embodiments, methods and processes described herein are utilized to detect and/or measure an oligosaccharide (disaccharide) having the formula:

[IdoA-GalNAc](SO₃R)$_n$                Formula XII

In certain embodiments, oligosaccharides described herein, e.g., those detected and/or measured according to the methods and/or processes described herein, are disaccharides of Formula XII, wherein n is 0-2. The disaccharide is optionally sulfated with n SO₃R groups in any suitable location. In more specific embodiments, a disaccharide of Formula XII has a structure of IdoA-GalNAc, IdoA-GalNAc6S, IdoA-GalNAc4S, IdoA-GalNAc4S6S, or as set forth in any of the disaccharides of FIG. 14. In certain instances, compounds of Formulas XII-A to XII-D are provided by treating the glycosaminoglycan dermatan sulfate with a suitable glycosaminoglycan lyase.

In some embodiments, the detection and/or measurement of any one or more disaccharide of Formula XII is utilized in a process for diagnosing MPS I. In certain embodiments, the detection and/or measurement of any one or more disaccharide of Formula XII and one or more disaccharide of Formulas I-A to I-C is utilized in a process for diagnosing MPS I.

In certain embodiments, methods and processes described herein are utilized to detect and/or measure an oligosaccharide (disaccharide) having the formula:

[IdoA2S-GalNAc](SO₃R)$_n$                Formula XIII

In certain embodiments, oligosaccharides described herein, e.g., those detected and/or measured according to the methods and/or processes described herein, are disaccharides of Formula XIII, wherein n is 0-2. The disaccharide is optionally sulfated with n SO₃R groups in any suitable location. In more specific embodiments, a disaccharide of Formula XIII has a structure of IdoA2S-GalNAc, IdoA2S-GalNAc6S, IdoA2S-GalNAc4S, IdoA2S-GalNAc4S6S, or as set forth in any of the disaccharides of FIG. 15. In certain instances, compounds of Formulas XIII-A to XIII-D are provided by treating the glycosaminoglycan dermatan sulfate with a suitable glycosaminoglycan lyase.

In some embodiments, the detection and/or measurement of any one or more disaccharide of Formula XIII is utilized in a process for diagnosing MPS II. In certain embodiments, the detection and/or measurement of any one or more disaccharide of Formula XIII and one or more disaccharide of Formulas I-D to I-G is utilized in a process for diagnosing MPS II.

In certain embodiments, methods and processes described herein are utilized to detect and/or measure an oligosaccharide (trisaccharide) having the formula:

[GalNAc4S-IdoA-GalNAc](SO₃R)$_n$                Formula XIV

Figure 16:
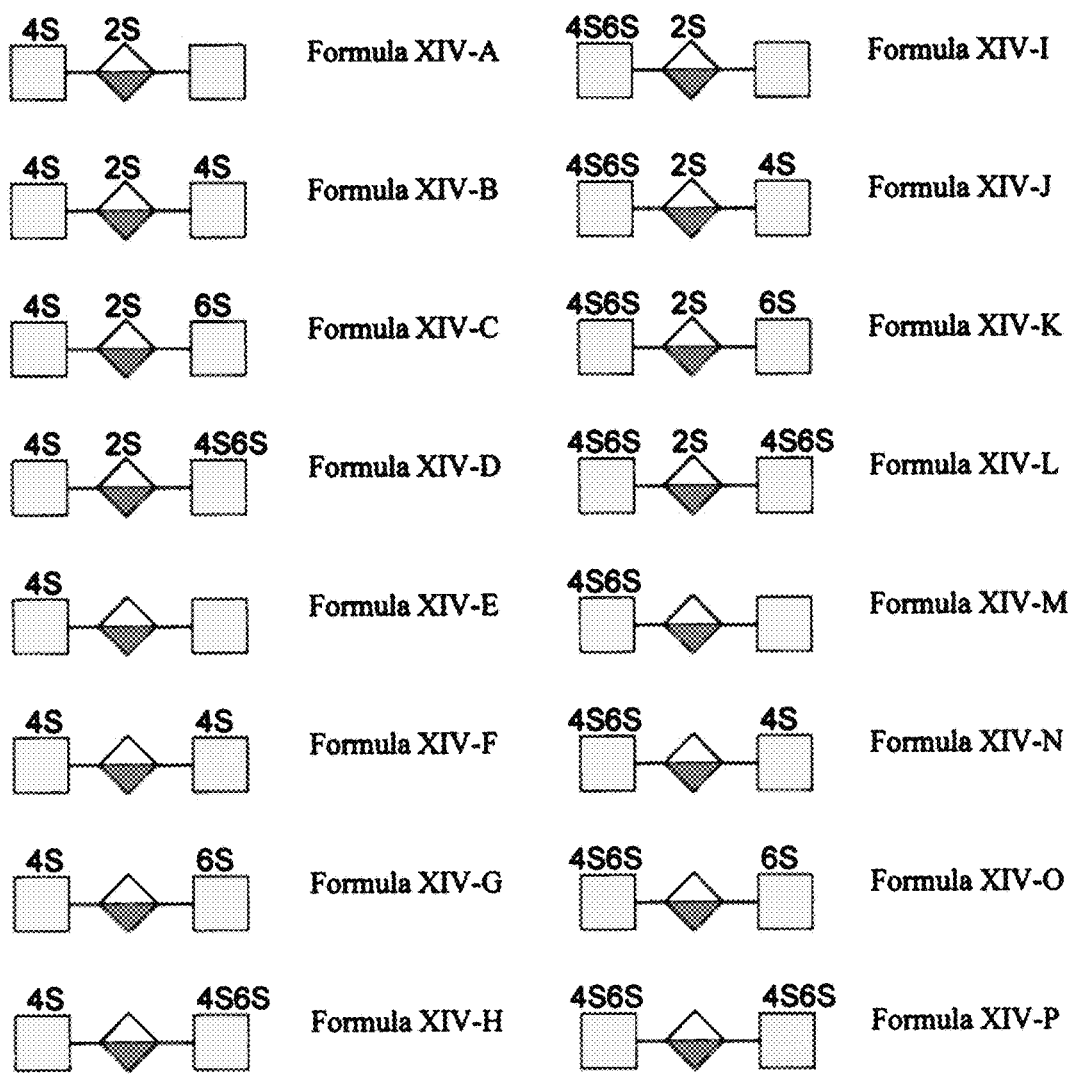
FIG. 16 illustrates oligosaccharides of Formula XIV.

In certain embodiments, oligosaccharides described herein, e.g., those detected and/or measured according to the methods and/or processes described herein, are trisaccharides of Formula XIV, wherein n is 0-4. The trisaccharide is optionally sulfated with n SO₃R groups in any suitable location. In more specific embodiments, a disaccharide of Formula XIV has a structure of GalNAc4S(±6S)-IdoA(±2S)-GalNAc(±4S)(±6S), or as set forth in any of the disaccharides of FIG. 16, wherein ± indicates that the indicated sulfation is independently present or absent. In certain instances, compounds of Formulas XIV-A to XIV-P are provided by treating the glycosaminoglycan dermatan sulfate with a suitable glycosaminoglycan lyase.

In some embodiments, the detection and/or measurement of any one or more trisaccharide of Formula XIV is utilized in a process for diagnosing MPS VI.

In certain embodiments, methods and processes described herein are utilized to detect and/or measure an oligosaccharide (trisaccharide) having the formula:

[GalNAc4S-GlcA-GalNAc](SO₃R)$_n$                Formula XV

Figure 17:
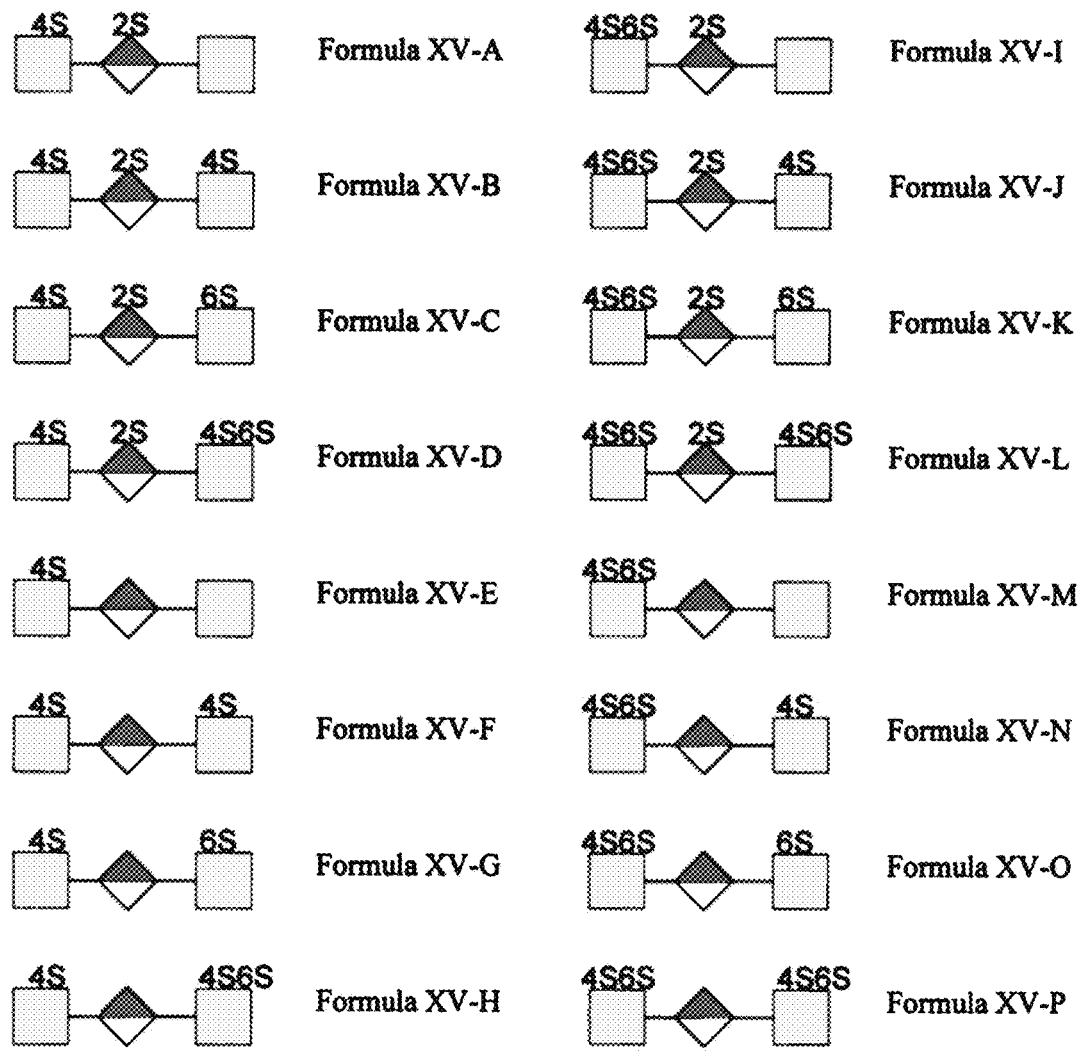
FIG. 17 illustrates oligosaccharides of Formula XV.

In certain embodiments, oligosaccharides described herein, e.g., those detected and/or measured according to the methods and/or processes described herein, are trisaccharides of Formula XV, wherein n is 0-3. The trisaccharide is optionally sulfated with n SO₃R groups in any suitable location. In more specific embodiments, a disaccharide of Formula XV has a structure of GalNAc4S(±6S)-GlcA(±2S)-GlcNAc(±4S)(±6S), or as set forth in any of the trisaccharides of FIG. 17, wherein ± indicates that the indicated sulfation is independently present or absent. In certain instances, compounds of Formulas XV-A to XV-P are provided by treating the glycosaminoglycan chondroitin sulfate with a suitable glycosaminoglycan lyase.

In some embodiments, the detection and/or measurement of any one or more trisaccharide of Formula XV is utilized in a process for diagnosing MPS VI. In certain embodiments, the detection and/or measurement of any one or more trisaccharide of Formula XIV and one or more trisaccharide of Formula XV is utilized in a process for diagnosing MPS VI.

In certain embodiments, methods and processes described herein are utilized to detect and/or measure an oligosaccharide (trisaccharide) having the formula:

GlcA-GlcNAc-GlcA                Formula XVI

In certain embodiments, oligosaccharides described herein, e.g., those detected and/or measured according to the methods and/or processes described herein, are trisaccharides of Formula XVI. In certain instances, compounds of Formulas XVI are provided by treating the glycosaminoglycan hyaluronan with a suitable glycosaminoglycan lyase. In some embodiments, the detection and/or measurement of any one or more trisaccharide of Formula XVI is utilized in a process for diagnosing MPS IIIB. In certain embodiments, the detection and/or measurement of any one or more trisaccharide of Formula XVI and one or more trisaccharide of either of Formulas V and/or VI is utilized in a process for diagnosing MPS IIIB.

In certain embodiments, methods and processes described herein are utilized to detect and/or measure an oligosaccharide (disaccharide) having the formula:

GlcA-GlcNAc                Formula XVII

In certain embodiments, oligosaccharides described herein, e.g., those detected and/or measured according to the methods and/or processes described herein, are disaccharides of Formula XVII. In certain instances, compounds of Formulas XVII are provided by treating the glycosaminoglycan hyaluronan with a suitable glycosaminoglycan lyase. In some embodiments, the detection and/or measurement of any one or more disaccharide of Formula XVII is utilized in a process for diagnosing MPS VII or MPS IX. In certain embodiments, the detection and/or measurement of a disaccharide of Formula XVII and one or more disaccharide of Formula XI is utilized in a process for diagnosing MPS VII. In some embodiments, the detection and/or measurement of a disaccharide of Formula XVII and the absence of one or more disaccharide of Formula XI is utilized in a process for diagnosing MPS IX.

In certain embodiments, methods and processes described herein are utilized to detect and/or measure an oligosaccharide (trisaccharide) having the formula:

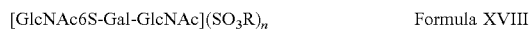

[GlcNAc6S-Gal-GlcNAc](SO$_3$R)$_n$     Formula XVIII

Figure 18:
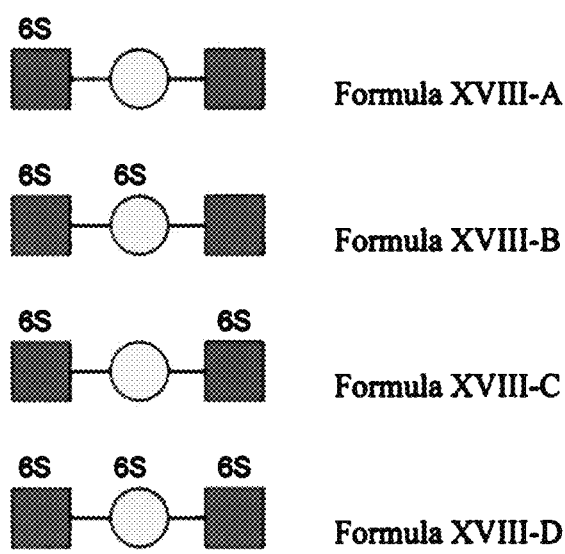
FIG. 18 illustrates oligosaccharides of Formula XVIII.

In certain embodiments, oligosaccharides described herein, e.g., those detected and/or measured according to the methods and/or processes described herein, are trisaccharides of Formula XVIII, and wherein n is 0-2. The trisaccharide is optionally sulfated with n SO$_3$R groups in any suitable location. In more specific embodiments, a disaccharide of Formula XVIII has a structure of GlcNAc6S-Gal-GlcNAc, GlcNAc6S-Gal6S-GlcNAc, GlcNAc6S-Gal-GlcNAc6S, GlcNAc6S-Gal6S-GlcNAc6S, or as set forth in any of the trisaccharides of FIG. 18. In certain instances, compounds of Formulas XVIII-A to XVIII-D are provided by treating the glycosaminoglycan keratan sulfate with a suitable glycosaminoglycan lyase.

In some embodiments, the detection and/or measurement of any one or more trisaccharide of Formula XVIII is utilized in a process for diagnosing MPS IIID. In certain embodiments, the detection and/or measurement of any one or more trisaccharide of Formula XVIII and one or more trisaccharide of Formulas IX and/or X is utilized in a process for diagnosing MPS IIID.

In certain embodiments, methods and processes described herein are utilized to detect and/or measure an oligosaccharide (disaccharide) having the formula:

[Gal6S-GlcNAc-(Gal)$_m$](SO$_3$R)$_n$     Formula XIX

In certain embodiments, oligosaccharides described herein, e.g., those detected and/or measured according to the methods and/or processes described herein, are disaccharides of Formula XIX, wherein n is 0-2 and m is 0-1. The disaccharide is optionally sulfated with n SO$_3$R groups in any suitable location. In more specific embodiments, a disaccharide of Formula XIX has a structure of Gal6S-GlcNAc, Gal6S-GlcNAc6S, or as set forth in any of the disaccharides of FIG. 19. In certain instances, compounds of Formulas XIX-A to XIX-B are provided by treating the glycosaminoglycan keratan sulfate with a suitable glycosaminoglycan lyase.

In some embodiments, the detection and/or measurement of any one or more disaccharide of Formula XIX is utilized in a process for diagnosing MPS IVA.

In certain embodiments, methods and processes described herein are utilized to detect and/or measure an oligosaccharide (disaccharide) having the formula:

[Gal-GlcNAc](SO$_3$R)$_n$     Formula XX

In certain embodiments, oligosaccharides described herein, e.g., those detected and/or measured according to the methods and/or processes described herein, are disaccharides of Formula XX, wherein n is 0-1. The disaccharide is optionally sulfated with n SO$_3$R groups in any suitable location. In more specific embodiments, a disaccharide of Formula XX has a structure of Gal-GlcNAc, Gal-GlcNAc6S, or as set forth in any of the disaccharides of FIG. 20. In certain instances, compounds of Formulas XX-A to XX-B are provided by treating the glycosaminoglycan keratan sulfate with a suitable glycosaminoglycan lyase.

In some embodiments, the detection and/or measurement of any one or more disaccharide of Formula XX is utilized in a process for diagnosing MPS IVB.

In certain embodiments, any analytical method or diagnostic process described herein comprises detecting and/or measuring any one or more of the oligosaccharides of any of Formulas I-XX, wherein the non-reducing end saccharide residue is saturated at 4 and 5 carbons of the non-reducing end saccharide residue, the non-reducing end saccharide residue is free of carbon-carbon unsaturation, or the oligosaccharide is free of carbon-carbon unsaturation. In certain instances, the non-reducing end saccharide residue is on the left end of the oligosaccharides disclosed herein. FIG. 1 illustrates the cleavage of the glycosaminoglycan (GAG) heparan sulfate with a glycosaminoglycan lyase (heparinase II). As illustrated, in certain instances, internal cleavage of glycosaminoglycans with glycosaminoglycan lyases provides oligosaccharides with carbon-carbon unsaturation between the C4 and C5 carbons of the non-reducing end of the oligosaccharide produce (i.e., the newly created oligosaccharide). In some embodiments, the oligosaccharide of any of Formulas I-XX is a disaccharide or trisaccharide comprised of two or three saccharide residues that formed the original two or three saccharide residues of a glycosaminoglycan (GAG) prior to treatment with the one or more glycosaminoglycan (GAG) lyase.

In certain embodiments, methods and processes described herein are utilized to detect and/or measure an oligosaccharide (trisaccharide) having the formula:

[IdoA-GlcN(Ac)$_m$-IdoA](SO$_3$R)$_n$     Formula XXI

In certain embodiments, oligosaccharides described herein, e.g., those detected and/or measured according to the methods and/or processes described herein, are trisaccharides of Formula XXI, wherein m is 0-1 and n is 0-4. The trisaccharide is optionally sulfated with n SO$_3$R groups in any suitable location. In certain instances, compounds of Formulas XXI are provided by treating the glycosaminoglycan heparan sulfate with a suitable glycosaminoglycan lyase.

In certain embodiments, methods and processes described herein are utilized to detect and/or measure an oligosaccharide (trisaccharide) having the formula:

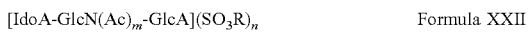

[IdoA-GlcN(Ac)$_m$-GlcA](SO$_3$R)$_n$     Formula XXII

In certain embodiments, oligosaccharides described herein, e.g., those detected and/or measured according to the methods and/or processes described herein, are trisaccharides of Formula XXII, wherein m is 0-1 and n is 0-3. The trisaccharide is optionally sulfated with n SO$_3$R groups in any suitable location. In certain instances, compounds of Formulas XXII are provided by treating the glycosaminoglycan heparan sulfate with a suitable glycosaminoglycan lyase.

In certain embodiments, methods and processes described herein are utilized to detect and/or measure an oligosaccharide (trisaccharide) having the formula:

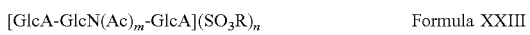

[GlcA-GlcN(Ac)$_m$-GlcA](SO$_3$R)$_n$     Formula XXIII

In certain embodiments, oligosaccharides described herein, e.g., those detected and/or measured according to the methods and/or processes described herein, are trisaccharides of Formula XXIII, wherein m is 0-1 and n is 0-3. The trisaccharide is optionally sulfated with n SO₃R groups in any suitable location. In certain instances, compounds of Formulas XXIII are provided by treating the glycosaminoglycan heparan sulfate with a suitable glycosaminoglycan lyase.

In some embodiments, the detection and/or measurement of any one or more trisaccharide of any of Formulas XXI to XXIII is utilized in a process for diagnosing a disorder associated with the accumulation of heparan sulfate (e.g., a heparan sulfate lysosomal storage disease such as, by way of non-limiting example, MPS I, MPS II, MPS IIIA, MPS IIIB, MPS IIIC, MPS IIID, MPS VII, or a combination thereof). In certain embodiments, an oligosaccharide of any of Formulas XXI to XXIII is saturated or unsaturated at the C4 and C5 positions of the saccharide residue at the non-reducing end of the oligosaccharide. In some embodiments, a process for diagnosing a disorder associated with the accumulation of heparan sulfate (e.g., MPS I, MPS II, MPS IIIA, MPS IIIB, MPS IIIC, MPS IIID, MPS VII, or a combination thereof) further comprises detecting one or more oligosaccharide, as set forth above and as appropriate (e.g., any of Formulas I-XX, as they pertain to the particular disorder being diagnosed).

In certain embodiments, methods and processes described herein are utilized to detect and/or measure an oligosaccharide (trisaccharide) having the formula:

[IdoA-GalNAc-Ido](SO₃R)ₙ          Formula XXIV

In certain embodiments, oligosaccharides described herein, e.g., those detected and/or measured according to the methods and/or processes described herein, are trisaccharides of Formula XXIV, wherein n is 0-4. The trisaccharide is optionally sulfated with n SO₃R groups in any suitable location. In certain instances, compounds of Formulas XXIV are provided by treating the glycosaminoglycan chondroitin and/or dermatan sulfate with a suitable glycosaminoglycan lyase.

In certain embodiments, methods and processes described herein are utilized to detect and/or measure an oligosaccharide (trisaccharide) having the formula:

[IdoA-GalNAc-GlcA](SO₃R)ₙ          Formula XXV

In certain embodiments, oligosaccharides described herein, e.g., those detected and/or measured according to the methods and/or processes described herein, are trisaccharides of Formula XXV, n is 0-3. The trisaccharide is optionally sulfated with n SO₃R groups in any suitable location. In certain instances, compounds of Formulas XXV are provided by treating the glycosaminoglycan chondroitin and/or dermatan sulfate with a suitable glycosaminoglycan lyase.

In certain embodiments, methods and processes described herein are utilized to detect and/or measure an oligosaccharide (trisaccharide) having the formula:

[GlcA-GalNAc-Ido](SO₃R)ₙ          Formula XXVI

In certain embodiments, oligosaccharides described herein, e.g., those detected and/or measured according to the methods and/or processes described herein, are trisaccharides of Formula XXVI, wherein n is 0-3. The trisaccharide is optionally sulfated with n SO₃R groups in any suitable location. In certain instances, compounds of Formulas XXVI are provided by treating the glycosaminoglycan chondroitin and/or dermatan sulfate with a suitable glycosaminoglycan lyase.

In certain embodiments, methods and processes described herein are utilized to detect and/or measure an oligosaccharide (trisaccharide) having the formula:

[GlcA-GalNAc-GlcA](SO₃R)ₙ          Formula XXVII

In certain embodiments, oligosaccharides described herein, e.g., those detected and/or measured according to the methods and/or processes described herein, are trisaccharides of Formula XXVII, wherein n is 0-2. The trisaccharide is optionally sulfated with n SO₃R groups in any suitable location. In certain instances, compounds of Formulas XXVII are provided by treating the glycosaminoglycan chondroitin and/or dermatan sulfate with a suitable glycosaminoglycan lyase.

In some embodiments, the detection and/or measurement of any one or more trisaccharide of any of Formulas XXIV to XXVII is utilized in a process for diagnosing a disorder associated with the accumulation of chondroitin and/or dermatan sulfate (e.g., a chondroitin and/or dermatan sulfate lysosomal storage disease). In certain embodiments, an oligosaccharide of any of Formulas XXIV to XXVII is saturated or unsaturated at the C4 and C5 positions of the saccharide residue at the non-reducing end of the oligosaccharide. In some embodiments, a process for diagnosing a disorder associated with the accumulation of chondroitin and/or dermatan sulfate further comprises detecting one or more oligosaccharide, as set forth above and as appropriate (e.g., any of Formulas I-XX, as they pertain to the particular disorder being diagnosed).

In certain embodiments, methods and processes described herein are utilized to detect and/or measure an oligosaccharide (trisaccharide) having the formula:

GlcA-GlcNAc-GlcA          Formula XXVIII

In certain embodiments, oligosaccharides described herein, e.g., those detected and/or measured according to the methods and/or processes described herein, are trisaccharides of Formula) (XVIII. In certain instances, compounds of Formulas XXVIII are provided by treating the glycosaminoglycan hyaluronan with a suitable glycosaminoglycan lyase.

In some embodiments, the detection and/or measurement of a trisaccharide of Formula XXVIII is utilized in a process for diagnosing a disorder associated with the accumulation of hyaluronan (e.g., a hyaluronan lysosomal storage disease). In certain embodiments, an oligosaccharide of Formula XXVIII is saturated or unsaturated at the C4 and C5 positions of the saccharide residue at the non-reducing end of the oligosaccharide. In some embodiments, a process for diagnosing a disorder associated with the accumulation of hyaluronan further comprises detecting one or more oligosaccharide, as set forth above and as appropriate (e.g., any of Formulas I-XX, as they pertain to the particular disorder being diagnosed).

In certain embodiments, methods and processes described herein are utilized to detect and/or measure an oligosaccharide (trisaccharide) having the formula:

[Gal-GlcNAc-Gal](SO₃R)ₙ          Formula XXIX

In certain embodiments, oligosaccharides described herein, e.g., those detected and/or measured according to the methods and/or processes described herein, are trisaccharides of Formula XXIX, wherein n is 0-3. The trisaccharide is optionally sulfated with n SO₃R groups in any suitable location. In certain instances, compounds of Formulas XXIX are provided by treating the glycosaminoglycan keratan sulfate with a suitable glycosaminoglycan lyase.

In some embodiments, the detection and/or measurement of any one or more trisaccharide of Formula XXIX is utilized in a process for diagnosing a disorder associated with the accumulation of keratan sulfate (e.g., a keratan sulfate lysosomal storage disease). In certain embodiments, an oligosaccharide of Formula XXIX is saturated or unsaturated at the C4 and C5 positions of the saccharide residue at the non-reducing end of the oligosaccharide. In specific embodiments, the oligosaccharide is saturated at the C4 and C5 positions of the saccharide residue at the non-reducing end of the oligosaccharide. In some embodiments, a process for diagnosing a disorder associated with the accumulation of keratan sulfate further comprises detecting one or more oligosaccharide, as set forth above and as appropriate (e.g., any of Formulas I-XX, as they pertain to the particular disorder being diagnosed).

In certain embodiments, methods and processes described herein are utilized to detect and/or measure an oligosaccharide (trisaccharide) having the formula:

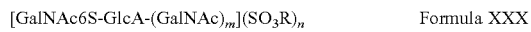

[GalNAc6S-GlcA-(GalNAc)$_m$](SO$_3$R)$_n$    Formula XXX

In certain embodiments, oligosaccharides described herein, e.g., those detected and/or measured according to the methods and/or processes described herein, are di- and tri-saccharides of Formula XXX, wherein n is 0-3. The di- or tri-saccharide is optionally sulfated with n SO$_3$R groups in any suitable location. In certain instances, compounds of Formulas XXX are provided by treating the glycosaminoglycan chondroitin sulfate with a suitable glycosaminoglycan lyase. In some embodiments, the detection and/or measurement of any one or more disaccharide or trisaccharide of Formula XXX is utilized in a process for diagnosing MPS IVA. In some embodiments, a di- or tri-saccharide of Formula XXX has a structure o as set forth in any of the disaccharides of FIG. 21.

In certain embodiments, methods and processes described herein are utilized to detect and/or measure an oligosaccharide (trisaccharide) having the formula:

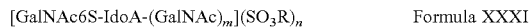

[GalNAc6S-IdoA-(GalNAc)$_m$](SO$_3$R)$_n$    Formula XXXI

Figure 22:
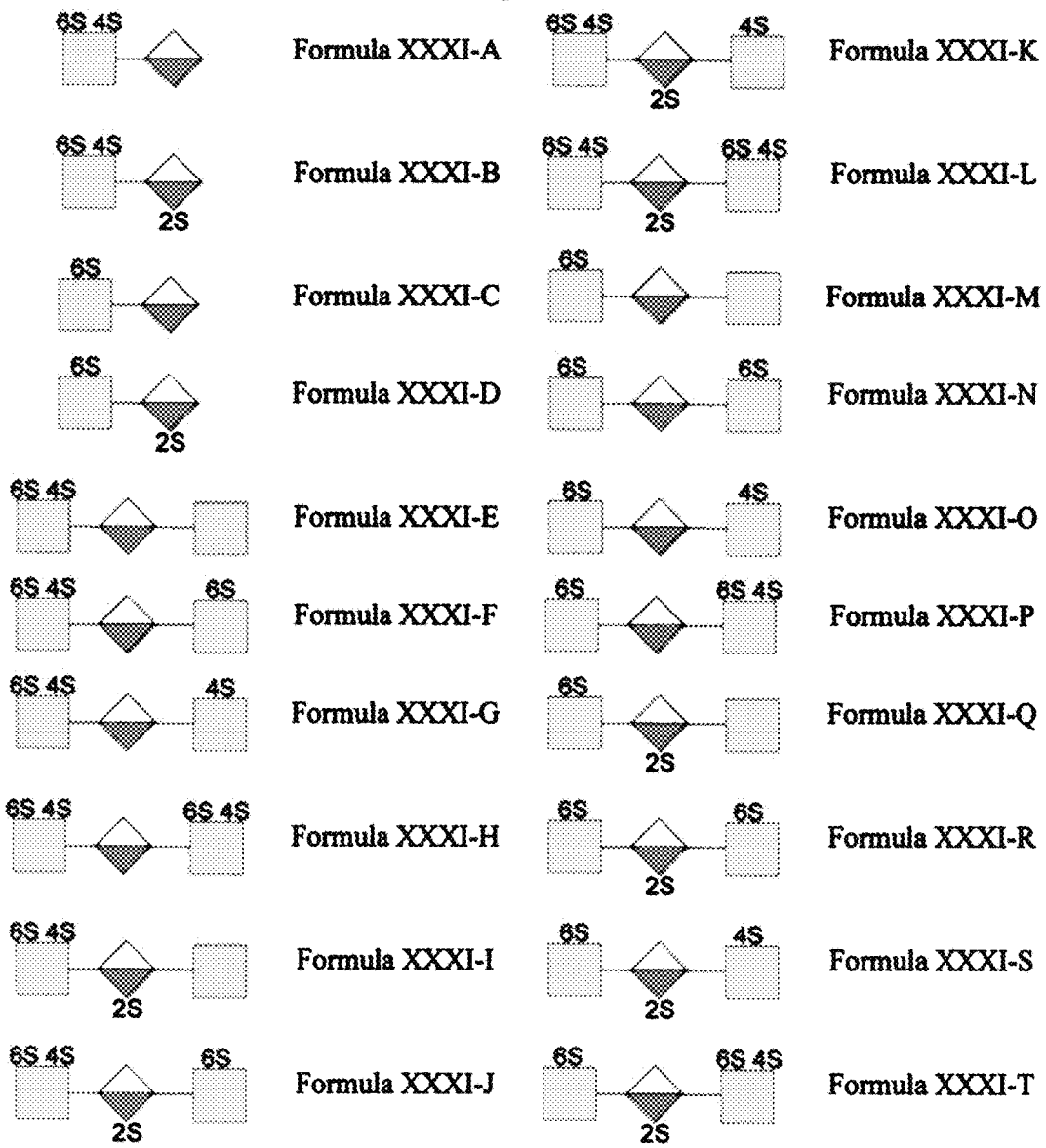
FIG. 22 illustrates oligosaccharides of Formula XXXI.

In certain embodiments, oligosaccharides described herein, e.g., those detected and/or measured according to the methods and/or processes described herein, are di- or tri-saccharides of Formula XXXI, wherein n is 0-4 and m is 0-1. The di- or tri-saccharide is optionally sulfated with n SO$_3$R groups in any suitable location. In more specific embodiments, a disaccharide of Formula XVIII has a structure of any of the di- or tri-saccharides of FIG. 22. In certain instances, compounds of Formulas XXXI-A to XXXI-T are provided by treating the glycosaminoglycan dermatan sulfate with a suitable glycosaminoglycan lyase.

In some embodiments, the detection and/or measurement of any one or more di- or tri-saccharide of Formula XXXI is utilized in a process for diagnosing MPS IVA.

In certain embodiments, methods and processes described herein are utilized to detect and/or measure an oligosaccharide (disaccharide) having the formula:

[GlcA-GalNAc](SO$_3$R)$_n$    Formula XXXII

In certain embodiments, oligosaccharides described herein, e.g., those detected and/or measured according to the methods and/or processes described herein, are disaccharides of Formula XXXII, wherein n is 0-2. The disaccharide is optionally sulfated with n SO$_3$R groups in any suitable location. In more specific embodiments, a disaccharide of Formula XXXII has a structure as set forth in any of the disaccharides of FIG. 23. In certain instances, compounds of Formulas XXXII-A to XXXII-C are provided by treating the glycosaminoglycan chondroitin sulfate with a suitable glycosaminoglycan lyase.

In some embodiments, the detection and/or measurement of any one or more disaccharide of Formula XXXII is utilized in a process for diagnosing MPS VII.

In certain embodiments, an oligosaccharide of any of Formulas XXX to XXXII is saturated or unsaturated at the C4 and C5 positions of the saccharide residue at the non-reducing end of the oligosaccharide.

In certain embodiments, any of the processes or methods provided herein comprise detecting and/or measuring the amount of any oligosaccharide provided in any of Formulas I to XX, any of Formulas XXI to XXIX, or any of Formulas I to XXXII. In further embodiments, any process or method provided herein comprises detecting and/or measuring the amount of any oligosaccharide provided in any of Formulas I to XX, any of Formulas XXI to XXIX, or any of Formulas I to XXXII, wherein the oligosaccharide is attached to a detectable label at the reducing end of the oligosaccharide.

In certain embodiments, provided herein is a compound of any of Formulas I to XX, any one of Formulas XXI to XXIX, or any of Formulas I to XXXII. In some embodiments, provided herein is a compound of any of FIGS. 4-23. In certain embodiments, the compound of any of Formulas I to XXXII or FIGS. 4-23 is an isolated and/or purified compound. In some embodiments, the isolated and/or purified compound of any of Formulas I to XXXII or FIGS. 4-23 is substantially free of oligosaccharides comprising a saccharide residue at the non-reducing end of the oligosaccharide that is unsaturated at the C4 and C5 positions. As an illustrative example of non-reducing end saccharide residues that are saturated and unsaturated at the C4 and C5 positions, an L-iduronic acid (IdoA) residue that is saturated at the C4 and C5 positions has a structure as follows:

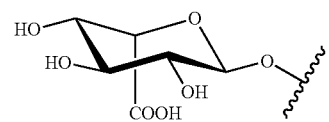

whereas an L-iduronic acid (IdoA) residue at the non-reducing end of the oligosaccharide that is unsaturated at the C4 and C5 positions may have a structure as follows:

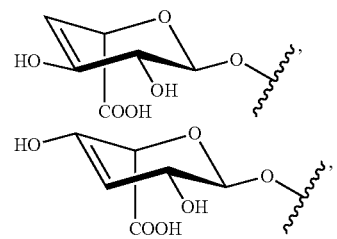

or the like. Oligosaccharides having non-reducing end saccharide residues that are saturated at the C4 and C5 position are referred to herein as "C4-C5 non-reducing end saturated oligosaccharides".

In certain embodiments, unsaturated saccharide residues include the unsaturated residue of IdoA, which is denoted by ; and the unsaturated residue of GlcA which is denoted by ◆.

In some embodiments, the isolated and/or purified compound described herein comprises at least at least 50%, at least 60%, at least 70%, at least 80%, at least 90%, at least 95%, at least 97%, at least 98%, or at least 99% oligosaccharide (by weight). In further or alternative embodiments, the isolated and/or purified compound comprises 20%, at least 30%, at least 40%, at least 50%, at least 60%, at least 70%, at least 80%, at least 90%, at least 95%, at least 97%, at least 98%, or at least 99% NRE-saturated oligosaccharide (by weight).

In some embodiments, provided herein is a composition comprising one or more isolated oligosaccharide of any of FIGS. 4-23. In certain embodiments, the oligosaccharide present in the composition is less than 90% by weight non-reducing end unsaturated oligosaccharide. In certain embodiments, the oligosaccharide present in the composition is less than 80% by weight non-reducing end unsaturated oligosaccharide. In certain embodiments, the oligosaccharide present in the composition is less than 70% by weight non-reducing end unsaturated oligosaccharide. In certain embodiments, the oligosaccharide present in the composition is less than 60% by weight non-reducing end unsaturated oligosaccharide. In certain embodiments, the oligosaccharide present in the composition is less than 50% by weight non-reducing end unsaturated oligosaccharide. In certain embodiments, the oligosaccharide present in the composition is less than 40% by weight non-reducing end unsaturated oligosaccharide. In certain embodiments, the oligosaccharide present in the composition is less than 30% by weight non-reducing end unsaturated oligosaccharide. In certain embodiments, the oligosaccharide present in the composition is less than 25% by weight non-reducing end unsaturated oligosaccharide. In certain embodiments, the oligosaccharide present in the composition is less than 20% by weight non-reducing end unsaturated oligosaccharide. In certain embodiments, the oligosaccharide present in the composition is less than 15% by weight non-reducing end unsaturated oligosaccharide. In certain embodiments, the oligosaccharide present in the composition is less than 10% by weight non-reducing end unsaturated oligosaccharide. In certain embodiments, the oligosaccharide present in the composition is less than 5% by weight non-reducing end unsaturated oligosaccharide. In some embodiments, the composition further comprises chromatographic resin or electrophoretic resin. In some embodiments, the resin is a high performance liquid chromatographic resin, or the like.

The compounds of any of Formulas I-XXXII or FIGS. 4-23 are obtained in any suitable manner, e.g., by generation and purification from natural sources, chemical synthesis, or any other suitable method. These structures do not naturally exist in an isolated and/or purified form.

The described di- and trisaccharides are optionally generated and purified from natural sources. In certain embodiments, starting with glycosaminoglycans from natural sources (for example, chondroitin sulfate, heparan sulfate, heparin, or synthetic heparin (or heparan) like carbohydrates), these di- and trisaccharides are generated by treating the glycan with glycosaminoglycan lyases (for example heparin lyases or chondroitinases) and purifying the di- and trisaccharides liberated from the preexisting non-reducing ends. In specific instances, the di- and trisaccharides liberated from the preexisting non-reducing end are unique because they do not contain a c4-5 double bond due to the action of the lyase.

Figure 24:
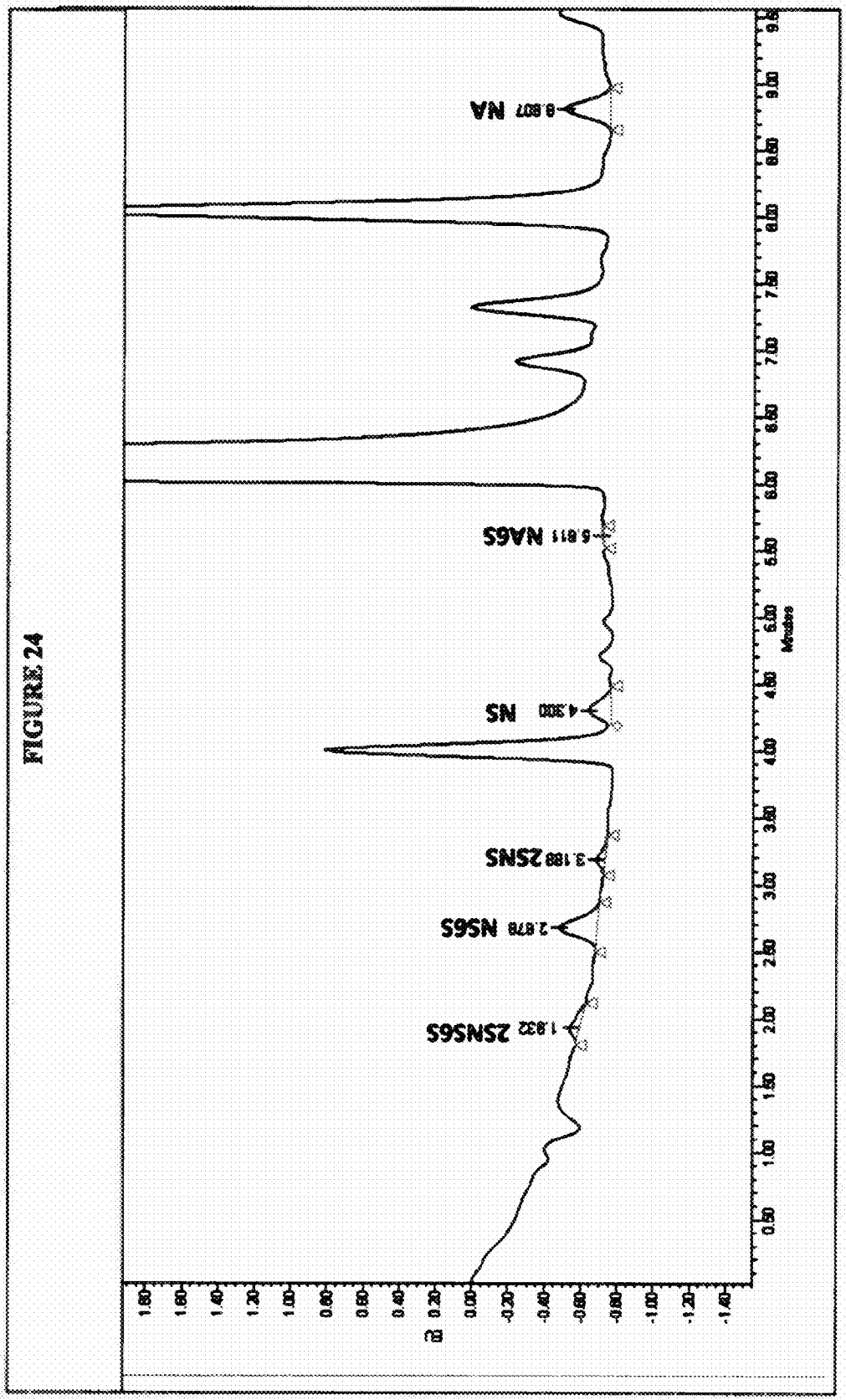
FIG. 24 illustrates disaccharides isolated from heparan sulfate from a normal human sample.
Figure 25:
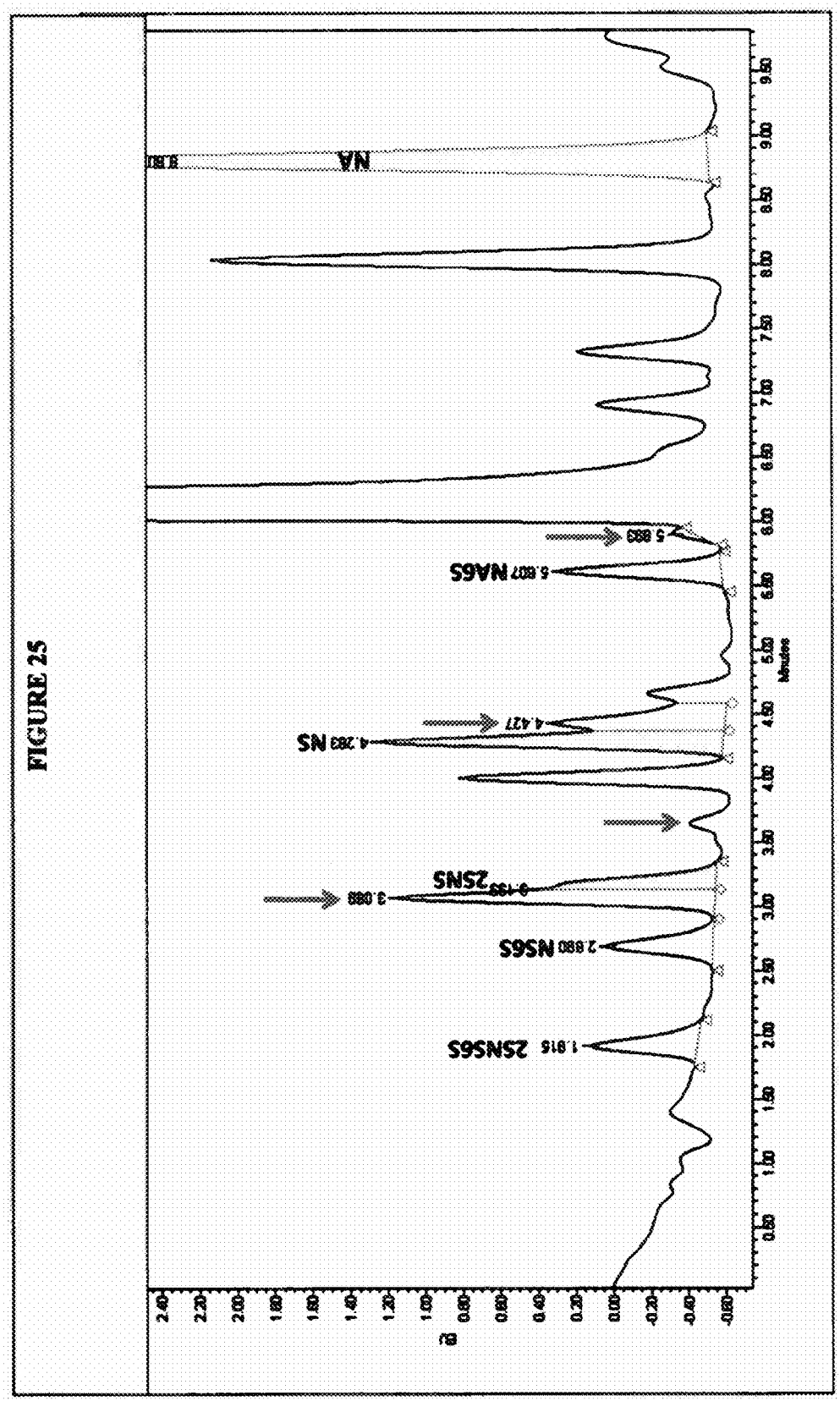
FIG. 25 illustrates disaccharides isolated from an MPS I (iduronidase deficient) sample.

In certain embodiments, the yield of the desired di- and trisaccharides are increased by using glycosaminoglycans that have been treated with glycan degradative enzymes (for example, heparanase or lysosomal exo-enzymes such as the 2-sulfatase, N-sulfatase, etc) to generate smaller fragments or fragments with a greater number of desirable non-reducing ends. In further or alternative embodiments, the yield is increased by starting with glycosaminoglycans that have been isolated from an organism or cell that has a defect in glycosaminoglycan degradation such that the desirable non-reducing ends are enriched (for example, glycosaminoglycans from iduronidase deficient systems, would be enriched in glycosaminoglycans that terminal on the non-reducing end with iduronate residues). As shown in FIGS. 24 and 25, these unique non-reducing end disaccharides can be isolated by HPLC. FIG. 24 shows disaccharides isolated from heparan sulfate from a normal human sample, while FIG. 25 shows disaccharides isolated from an MPS I (iduronidase deficient) sample. The saturated disaccharides (indicated with red arrows) can be isolated by collecting the appropriate fractions from this or a similar preparative chromatography.

Additional or alternative methods of obtaining such compounds include, e.g., chemical transformation of the unsaturated saccharides into the saturated saccharides. The described di- and trisaccharides can be synthesized by chemical or chemoenzymatic methods. Chemical methods for the synthesis of these saturated di- and trisaccharides are optionally converted from the methods described by Prabhu, Venot, and Boons (Organic Letters 2003 Vol. 5, No. 26 4975-4978), which is incorporated herein for such synthesis.

In further embodiments, provided herein is a compound of any of Formulas I-XXXII or FIGS. 4-23, wherein the compound is tagged with any label as described herein.

In some embodiments, an isolated or otherwise generated oligosaccharide described herein has a molecular weight of less than 2000 g/mol, less than 1500 g/mol, less than 1000 g/mol, less than 500 g/mol, less than 400 g/mol, less than 300 g/mol, less than 260 g/mol, less than 200 g/mol, less than 100 g/mol, or the like (e.g., prior to tagging with any detectable label that may be included in a process described herein).

Detection/Measurement Methods

Oligosaccharides (including e.g., oligosaccharides tagged with detectable labels) described herein are detected and/or measured in processes described herein in any suitable manner. In certain embodiments, detectable labels are detected and/or quantified according to any process described herein using any technique, particularly any technique suitable for the detectable label utilized. In some embodiments, suitable detection techniques include, by way of non-limiting example, one or more of a mass spectrometer, a nuclear magnetic resonance spectrometer, a UV-Vis spectrometer, an IR spectrometer, a fluorimeter, a phosphorimeter, a radiation spectrometer (e.g., a scintillation counter), a thin layer chromatographic technique, or the like. In certain embodiments, in any process described herein, oligosaccharides are optionally directly detected using a suitable technique, such as quantitative nuclear magnetic resonance. Quantitative nuclear magnetic resonance is also optionally utilized to quantify and/or detect the presence of a detectable label. In certain embodiments, one or more oligosaccharides are optionally detected using a suitable liquid chromatography mass spectrometer (LC-MS).

In some embodiments, oligosaccharides are tagged with an antibody or probe, and are quantified using any suitable method (e.g., dot blot techniques, immune detection techniques (e.g., ELISA), or the like).

Various analytical methods useful for the processes described herein include, by way of non-limiting example, mass spectrometry, chromatography, HPLC, UPLC, TLC, GC, HPAEC-PAD, electrophoresis—capillary or gel, or the like. In certain embodiments, wherein a chromatographic technique is utilized, any suitable solvent system is optionally employed. In certain embodiments, a column (e.g., Cosmogel DEAE, Tsk Gel DEAE, Cosmogel QA, Cosmogel CM, Cosmogel SP, 130A BEH particle Phenyl (1.7, 2.5, 3.5, 5, or 10 uM particle size), 130A BEH particle C18 (1.7, 2.5, 3.5, 5, or 10 uM particle size), HSS particle C18 (1.8, 3.5, or 5 uM particle size), 300A BEH particle C18 (1.7, 3.5, 5, 10 uM particle size), or the like with suitable length and internal diameter) is optionally loaded with an equilibrating solvent (e.g., a buffer or salt solution, such as a potassium acetate solution, sodium chloride solution, sodium acetate solution, ammonium acetate solution, or the like), e.g., with a pH of about 6, 7, or 8. In some embodiments, the buffer or salt solution has a concentration of about 10 mM, 20 mM, 30 mM, 50 mM, 100 mM, 500 mM, 1 M, 2 M, or the like. Any suitable flow rate is used, e.g., 0.5 mL/min, 1 mL, min, 1.5 mL/min, 2 mL/min, or the like. Following equilibration, a linear gradient is optionally utilized. In some embodiments, the linear gradient is run over 1-20 min, 1-10 min, 10-20 min, 1-5 min, 5-10 min, or the like. In certain embodiments, the gradient is a buffer or salt solution, e.g., as described above (e.g., from 0 M to 0.5 M, from 0 M to 3 M, from 0.5 M to 2 M, from 0 M to 2 M, from 1 M to 2 M, from 0 M to 3 M, from 2 M to 0 M, from 3 M to 0 M, or the like). Once the gradient has reached a final concentration, the eluent is optionally held at the final concentration for a suitable period of time (e.g., 1-20 min, 5-10 min, 10-15 min, 1-5 min, 1-10 min, 15-20 min, or the like). After the optional holding of the final concentration, the eluent may be switched to a second solvent or solvent system (e.g., an alcohol, such as methanol, ethanol, or isopropanol, acetonitrile, water, or the like). The switch to the second solvent system may be over a period of time, e.g., 15 seconds, 30 seconds, 45 seconds, 60 seconds, 2 min, 3 min, or the like. The second solvent system is optionally held for a period of time, such as 1 min, 2 min, 3 min, 4 min, 5 min, 6 min, or the like. Following the second solvent system cycle, the column is optionally restored to initial solvent conditions.

In certain embodiments, detection or measurement of an analytical device provides for diagnosis of a disease, diagnosis of severity of a disease, of efficacy of a therapy, or analysis based on other processes described herein. For example, in some embodiments, absence of a peak or signal (e.g., a peak or signal indicative of the presence of a particular oligosaccharide) indicates that an individual is in a non-diseased state, in remission for a disease state, or undergoing effective therapy for a disease, depending on the circumstances of the diagnosis. In certain embodiments, the presence and/or area of a peak or signal (including, e.g., the presence of a certain signal or peak pattern or fingerprint) is utilized to determine the severity of a disease. In some embodiments, the presence and/or area of a peak or signal is utilized to determine disease, disease severity, disease carrier status or the like, based on a certain threshold value for the disease, disease severity, disease carrier status. Such thresholds are optionally determined in any suitable manner, e.g., by analyzing control samples, such control samples coming from non-diseased individuals, diseased individuals, or the like.

In certain embodiments, a control biological sample utilized in any process described herein was provided from an individual that does not suffer from a disorder being diagnosed. In other embodiments, a control biological sample is taken from an individual suffering from a disorder being diagnosed. In certain embodiments, the result obtained from the control biological sample is stored in a database. In such cases a test sample is optionally compared to a plurality of control data in a database. Moreover in certain embodiments, any diagnostic process described herein is optionally utilized alone or in combination with other diagnostic techniques. Other diagnostic techniques include, by way of non-limiting example, symptom analysis, biopsies, detection of accumulation of other compounds in biological samples, or the like. In some embodiments, control biological samples are optionally taken from the same individual at substantially the same time, simply from a different location (e.g., one inflamed/arthritic synovial joint fluid vs the contralateral non-arthritic synovial joint). In other embodiments, control biological samples are optionally taken from the same individual at different points in time (e.g., before therapy and after therapy if the method being utilized is a method of monitoring a treatment therapy).

Detectable Labels

In the various embodiments of any process or method described herein, any suitable detectable label is optionally utilized. In some embodiments, detectable labels useful in the processes or methods described herein include, by way of non-limiting example, mass labels, antibodies, affinity labels, radiolabels, chromophores, fluorescent labels, or the like.

Fluorescent labels suitable for use in various embodiments herein include, by way of non-limiting example, 2-aminopyridine (2-AP), 2-aminobenzoic acid (2-AA), 2-aminobenzamide (2-AB), 2-aminoacridone (AMAC), p-aminobenzoic acid ethyl ester (ABEE), p-aminobenzonitrile (ABN), 2-amino-6-cyanoethylpyridine (ACP), 7-amino-4-methylcoumarine (AMC), 8-aminonaphthalene-1,3,6-trisulfate (ANTS), 7-aminonaphthalene-1,3-disulfide (ANDS), and 8-aminopyrene-1,3,6-trisulfate (APTS), or the like. The fluorescent labels can be attached by reductive amination with the fluorescent label and sodium cyanoborohydride or the like.

Mass labels suitable for use in various embodiments herein include, by way of non-limiting example, D-2-anthranilic acid, D-2-aminopyridine, D-methyl iodide, $^{13}$C methyl iodide, deuterated-pyridyl-amine, D-biotin or the like. The mass labels can be attached by permethylation or reductive amination by any method that is known to those of skill in the art.

Affinity labels suitable for use in various embodiments herein include, by way of non-limiting example, biotin and derivatives.

Radio labels suitable for use in various embodiments herein include, by way of non-limiting example, sodium borotritide ($NaB^3H_4$), or the like.

Chromophores suitable for use in various embodiments herein include, by way of non-limiting example, 4-amino-1,1'-azobenzene, 4'-N,N-dimethylamino-4-aminoazobenzene, aminoazobenzene, diaminoazobenzene, Direct Red 16, CI Acid Red 57, CI Acid Blue 45, CI Acid Blue 22, CL Mordant Brown 13, CI Direct Orange 75, or the like. The chromophores may be labeled by any method that is known to those of skill in the art, such as reductive amination with the chromophore and sodium cyanoborohydride.

In some embodiments, the detectable label is an antibody. In specific embodiments, the antibody is attached to a detectable compound, such as mass labels, radiolabels, chromophores, fluorescent labels, or the like. In some embodiments, antibodies are themselves detected and/or are detectable in various manners, e.g., as a chromophore, a fluorophore, or the like; or with a probe (e.g., using dot blot techniques, immune-detection techniques, or the like).

Purification Methods

In some embodiments, the processes described herein comprises further treatment steps of the test and/or control samples. For example, in some embodiments, the samples are homogenized and/or purified. In specific embodiments homogenization is achieved in any suitable manner including, by way of non-limiting example, with a basic solution (e.g., 0.1 N NaOH), sonication, tissue grinding or other chemical agents).

In certain embodiments, samples, including test samples and/or control samples, described herein are optionally purified prior to glycosaminoglycan processing (e.g., lyase treatment) and/or characterization. Test samples and/or control samples (i.e., one or more or all of the glycans found therein) are optionally purified using any suitable purification technique. Test samples and/or control samples are optionally purified at any suitable point in a process described herein, including before or after tagging of the glycans founds within the sample. In certain embodiments, purification techniques include centrifugation, electrophoresis, chromatography (e.g., silica gel or alumina column chromatography), gas chromatography, high performance liquid chromatography (HPLC) (e.g., reverse phase HPLC on chiral or achiral columns), thin layer chromatography, ion exchange chromatography, gel chromatography (e.g., gel filtration or permeation or size exclusion chromatography, gel electrophoresis), molecular sieve chromatography, affinity chromatography, size exclusion, filtration (e.g. through a florisil or activated charcoal plug), precipitation, osmosis, recrystallization, fluorous phase purification, distillation, extraction, chromatofocusing, supercritical fluid extraction, preparative flash chromatography (e.g., flash chromatography using a UV-Vis detector and/or a mass spectrometer (e.g., using the Biotage® suite of products) or the like.

In some embodiments, glycosaminoglycans, such as heparan sulfate, are naturally found attached to a core protein (together forming a proteoglycan). In some embodiments, provided herein are purification processes of separating glycosaminoglycan fragments (e.g., heparan sulfate fragments) from proteoglycans prior to processing the glycosaminoglycans for detection.

Therapeutic Methods

Provided in certain embodiments are methods of treating disorders associated with the abnormal degradation, biosynthesis and/or accumulation of glycosaminoglycans (GAGs), the methods comprising:
  a. administering an agent for treating MPS (e.g., an agent that modulates (e.g., promotes and/or inhibits) glycosaminoglycan biosynthesis and/or degradation) to an individual in need thereof;
  b. monitoring the accumulation of glycosaminoglycans in the individual using any process described herein for detecting or quantifying the amount of oligosaccharides (e.g., di- and/or tri-saccharides, such as GAG oligosaccharides, including heparan sulfate fragments) present in a lyase digested biological sample (e.g., urine, serum, plasma, or CSF sample) according to any process described herein.

Provided in further or alternative embodiments are methods of monitoring the treatment of disorders associated with the abnormal degradation, biosynthesis and/or accumulation of glycosaminoglycans (GAGs), the methods comprising:
  a. following administration of an agent for treating MPS (e.g., an agent that modulates (e.g., promotes and/or inhibits) glycosaminoglycan biosynthesis and/or degradation) to an individual in need thereof, using an analytical instrument to detect the presence of and/or measure the amount of a population of one or more C4-C5 non-reducing end saturated oligosaccharides present in a transformed biological sample that has been prepared by: treating a population of glycosaminoglycans, in or isolated from a biological sample taken from the individual, with at least one digesting glycosaminoglycan lyase to transform the glycosaminoglycans into the population of the one or more C4-C5 non-reducing end saturated oligosaccharide;
  b. displaying or recording the presence of or a measure of a population of one or more oligosaccharide.

In specific embodiments, the oligosaccharide(s) detected or measured is one or more C4-C5 non-reducing end saturated oligosaccharide(s). In some embodiments, the agent is administered one or more times. In certain embodiments, the agent is administered multiple times. In some embodiments, the agent is administered in a loading dose one or more times (e.g., in a loading dosing schedule) and subsequently administered in a maintenance dose (e.g., in a maintenance dosing schedule, such as three times a day, twice a day, once a day, once every two days, once every three days, once every four days, once a week, or the like). In some embodiments, when GAG oligosaccharide accumulation begins to increase or accelerate, the dose is optionally adjusted (e.g., the maintenance dose is increased, or an additional loading dose or dosing schedule is utilized).

In some embodiments, monitoring the accumulation of glycosaminoglycans comprises repeating the step of: using an analytical instrument to detect the presence of and/or measure the amount of a population of one or more oligosaccharides present in a transformed biological sample that has been prepared by treating a population of glycosaminoglycans, in or isolated from a biological sample from the individual, with at least one digesting glycosaminoglycan lyase to transform the glycosaminoglycans into the population of the one or more oligosaccharide. In specific embodiments, the step is repeated at periodic intervals (e.g., every day, every other day, every 2 days, every 3 days, every 4 days, every week, every month, every 3 months, quarterly, every 6 months, yearly, or the like), at regular times following a dose (e.g., 4 hours after a administration of the agent, 6 hours after administration of the agent, 8 hours after administration of the agent, 12 hours after administration of the agent, or the like), prior to administration of the dose (e.g., immediately prior to administration of the agent, 2 hours prior to administration of the agent, or the like), or any other monitoring schedule.

In some embodiments, the monitoring of the accumulation of glycosaminoglycans is conducted over a period of time, e.g., over a week, two weeks, a month, two months, three months, six months, a year, or the like. In some embodiments, the method for quantifying the amount of one or more oligosaccharides in a lyase digested biological sample (e.g., urine, serum, plasma, or CSF) comprises detecting and/or measuring (e.g., with an analytical device), one or more oligosaccharides within the lyase digested biological sample from the individual after the biological sample obtained from the individual has been treated with one or more glycosaminoglycan lyases. In certain embodiments, such glycosaminoglycan lyases are suitable for preparing di- and/or tri-saccharides from the glycosaminoglycans present in the biological sample obtained from the individual. In certain instances, the reducing end of a representative portion of the one or more oligosaccharides in the transformed biological sample is tagged with any suitable detectable label (e.g., a mass label, a radio label, a fluorescent label, a chromophore label, affinity label, an antibody). In some embodiments, the process comprises displaying or recording such a characterization of the population of oligosaccharides and/or tagged oligosaccharides.

In some embodiments, the agent that modulates glycosaminoglycan biosynthesis includes glycosaminoglycan accumulation inhibitors, agents that promote glycosaminoglycan degradation, agents that activate enzymes that degrade glycosaminoglycans, agents that inhibit biosynthesis of glycosaminoglycans, or the like. In some embodiments, the agent that modulates glycosaminoglycan biosynthesis is an agent that selectively modulates heparan sulfate biosynthesis, an agent that selectively modulates chondroitin sulfate biosynthesis, an agent that selectively modulates dermatan sulfate biosynthesis, an agent that selectively modulates keratan sulfate biosynthesis, an agent that selectively modulates hyaluronan biosynthesis, or a combination thereof.

In some instances, the detection and/or the quantification of the identity and/or amount of oligosaccharides present in a biological sample is used to identify and/or diagnose a disorder associated with abnormal degradation, biosynthesis and/or accumulation of glycosaminoglycans in an individual suspected of having such a disorder.

In some instances, the detection and/or the quantification of the identity and/or amount of oligosaccharides present in the biological sample is used to monitor severity and course of the disease in an individual diagnosed with or suspected of having a disorder associated with the abnormal degradation, biosynthesis and/or accumulation of glycosaminoglycans. In some instances, the detection and/or the quantification of the identity and/or amount of oligosaccharides present in the biological sample is used to calculate the administered dose of an agent that modulates (e.g., promotes and/or inhibits) glycosaminoglycan biosynthesis and/or degradation.

In certain instances, wherein following administration of a selected dose of a an agent that modulates (e.g., promotes and/or inhibits) glycosaminoglycan biosynthesis and/or degradation, an individual's condition does not improve, the detection and/or the quantification of the identity and/or amount of oligosaccharides present in a biological sample provides for a treatment regimen to be modified depending on the severity and course of the disease, disorder or condition, previous therapy, the individual's health status and response to the drugs, and the judgment of the treating physician.

In certain embodiments, monitoring the accumulation of glycosaminoglycans in the individual comprises detecting or quantifying the amount of an oligosaccharide (or one or more oligosaccharides) in a sample obtained from the individual (e.g., according to any method described herein) to obtain a first accumulation result (e.g., an initial reading before treatment has begun, or at any other time) and a second accumulation result that is subsequent to obtaining the first result. In some embodiments, the second result is compared to the first result to determine if the treatment is effectively reducing, maintaining, or reducing the rate of increasing the oligosaccharide levels in a substantially identically obtained sample from the individual being treated. In certain embodiments, depending on the difference between the first and second results, the treatment can be altered, e.g., to increase or decrease the amount of agent administered; to substitute the therapeutic agent with an alternative therapeutic agent; or the like. In certain embodiments, the dose of the therapeutic agent is decreased to a maintenance level (e.g., if the oligosaccharide level has been reduced sufficiently); further monitoring of oligosaccharide levels is optional in such situation, e.g., to ensure that reduced or maintained levels of oligosaccharide (e.g., GAG oligosaccharide(s)) are achieved.

Alternatively, provided herein is a method of detecting response to therapy in an individual or a method of predicting response to therapy in an individual comprising:

a. administering an agent for treating MPS (e.g., an agent that modulates (e.g., promotes and/or inhibits) glycosaminoglycan biosynthesis and/or degradation) to a plurality of cells from an individual in need thereof (e.g., a plurality of fibroblasts, serum, plasma, or CSF cells from a human suffering from MPS);

b. monitoring the accumulation of glycosaminoglycans in the plurality of cells using any process described herein for detecting or quantifying the amount of oligosaccharides (e.g., di- and/or tri-saccharides, such as GAG oligosaccharides, including heparan sulfate fragments) present in a lyase digested biological sample from the plurality of cells according to any process described herein.

In specific embodiments, the oligosaccharide(s) detected or measured is one or more C4-C5 non-reducing end saturated oligosaccharide(s). It is to be understood that a plurality of cells from an individual includes cells that are directly taken from the individual, and/or cells that are taken from an individual followed by culturing to expand the population thereof.

As discussed above, FIGS. 24 and 25 illustrate that C4-C5 non-reducing end saturated oligosaccharides can be isolated by, e.g., HPLC.

In some embodiments, monitoring the accumulation of glycosaminoglycans comprises repeating the step of: using an analytical instrument to detect the presence of and/or measure the amount of a population of one or more oligosaccharides present in a transformed biological sample that has been prepared by treating a population of glycosaminoglycans, in or isolated from a biological sample from the individual, with at least one digesting glycosaminoglycan lyase to transform the glycosaminoglycans into the population of the one or more oligosaccharide. In specific embodiments, the step is repeated at periodic intervals (e.g., every day, every other day, every 2 days, every 3 days, every 4 days, every week, or the like), or any other monitoring schedule.

Disorders

Disorders associated with the abnormal degradation, biosynthesis and/or accumulation of glycosaminoglycans useful in the treatment and diagnostic methods and processes described herein include any disorder wherein accumulation of glycosaminoglycans and/or fragments thereof can be detected in a biological sample taken from an individual suffering from such a disorder. As discussed herein, disorders associated with abnormal glycosaminoglycan degradation, biosynthesis, and/or accumulation include e.g., lysosomal storage diseases. In specific embodiments, a lysosomal storage disease is mucopolysaccharidosis (MPS). In some embodiments, a mucopolysaccharidosis (MPS) is MPS I, MPS II, MPS IIIA, MPS IIIB, MPS IIIC, MPS IIID, MPS IVA, MPS IVB, MPS VI, MPS VII, MPS IX, or a combination thereof.

Figure 26:
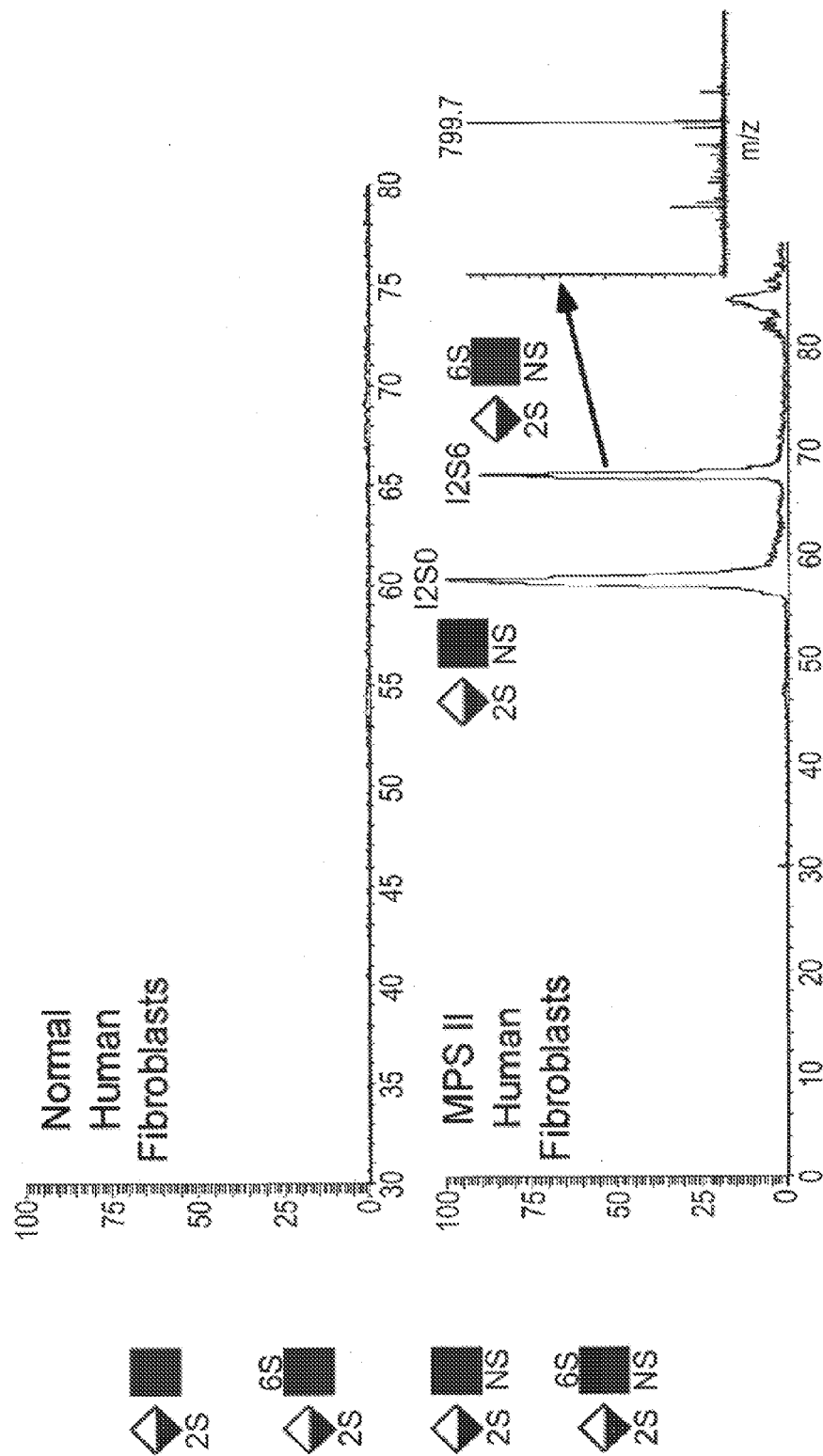
FIG. 26 illustrates the detection of oligosaccharides described herein in individuals having an MPS disease state as compared to individuals lacking an MPS disease state.
Figure 27:
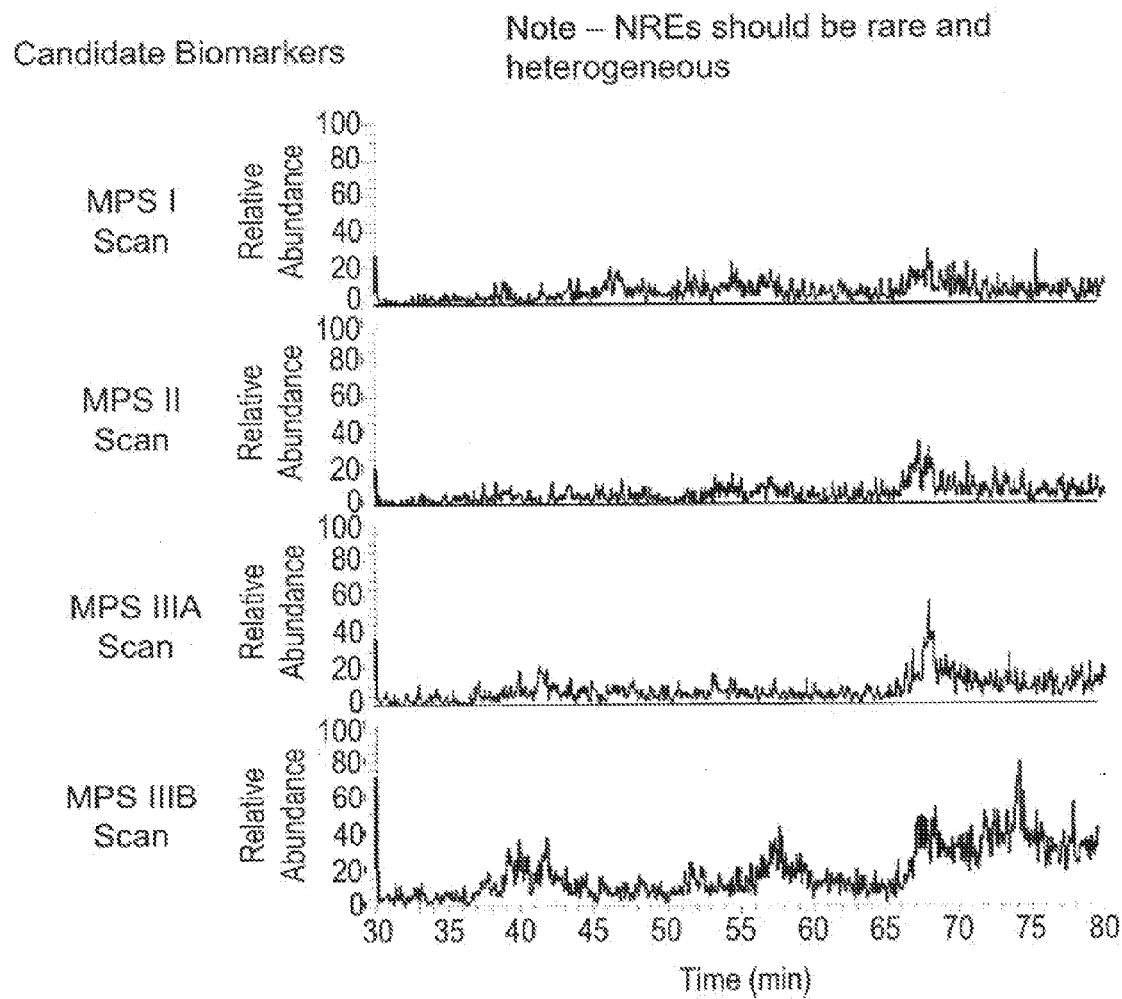
FIG. 27 illustrates mass spectrometry results for non-reducing end oligosaccharides in a non-MPS sample.
Figure 28A:
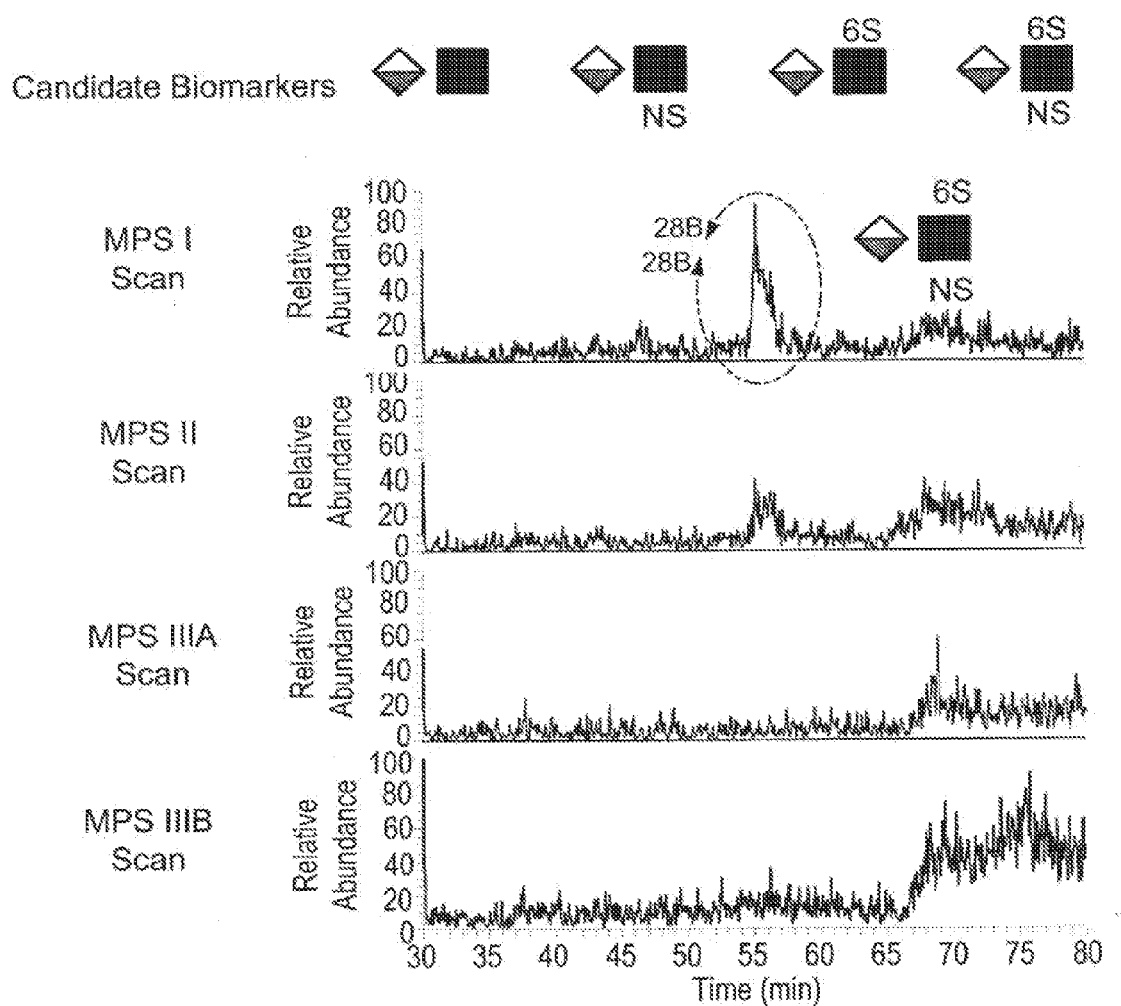
FIG. 28A illustrates mass spectrometry results for non-reducing end oligosaccharides in a MPS I sample.
Figure 28B:
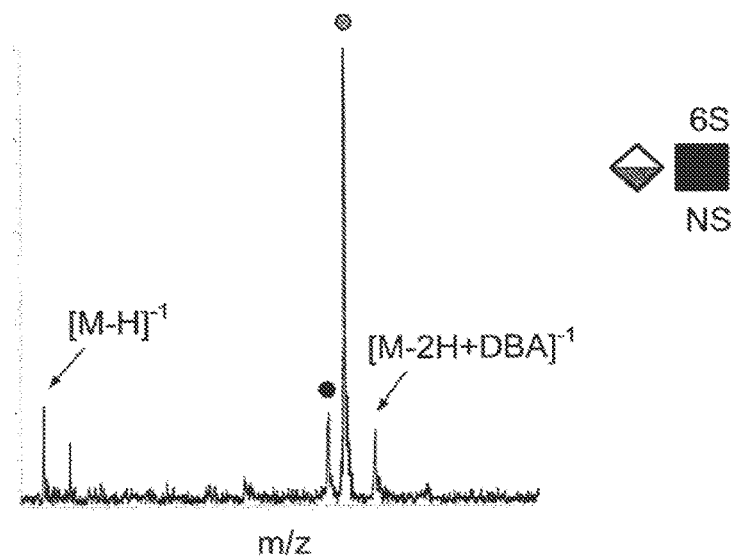
FIG. 28B is an enlarged representation of the '28B' region of FIG. 28A.
Figure 29B:
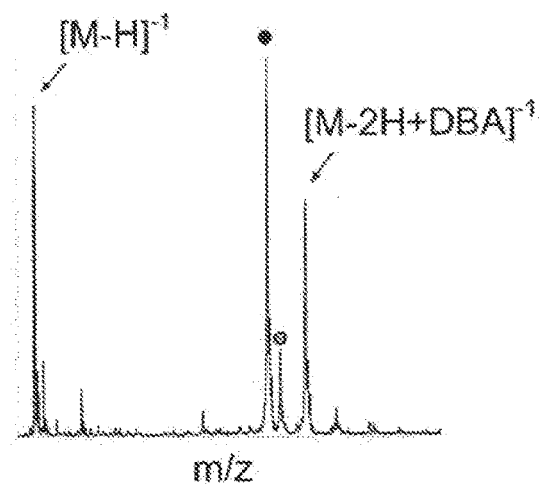
FIG. 29B is an enlarged representation of the '29B' region of FIG. 29A.
Figure 29C:
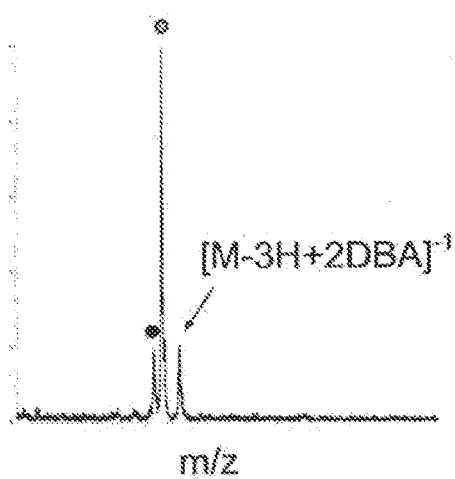
FIG. 29C is an enlarged representation of the '29C' region of FIG. 29A.
Figure 30A:
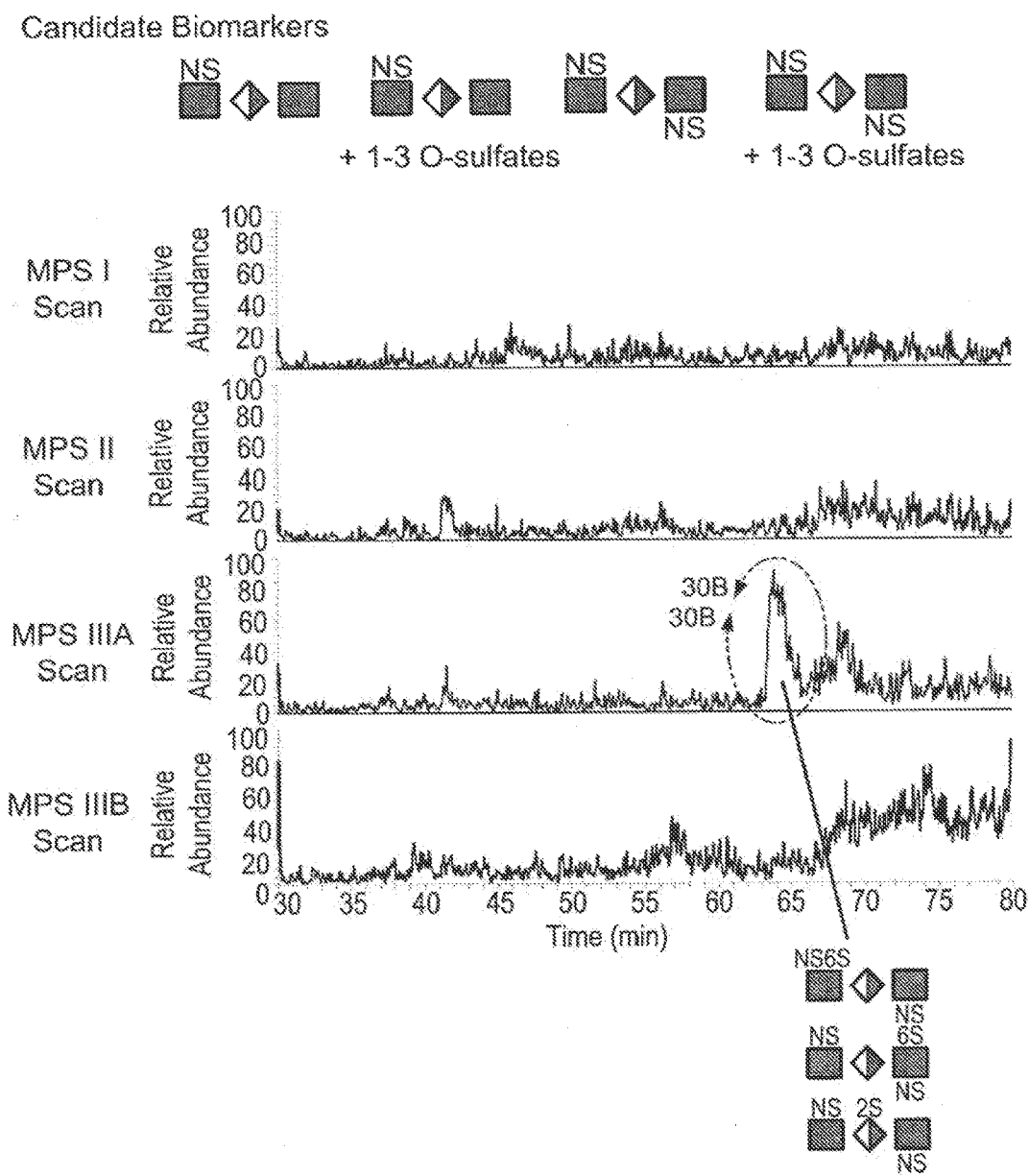
FIG. 30A illustrates mass spectrometry results for non-reducing end oligosaccharides in a MPS IIIA sample.
Figure 30B:
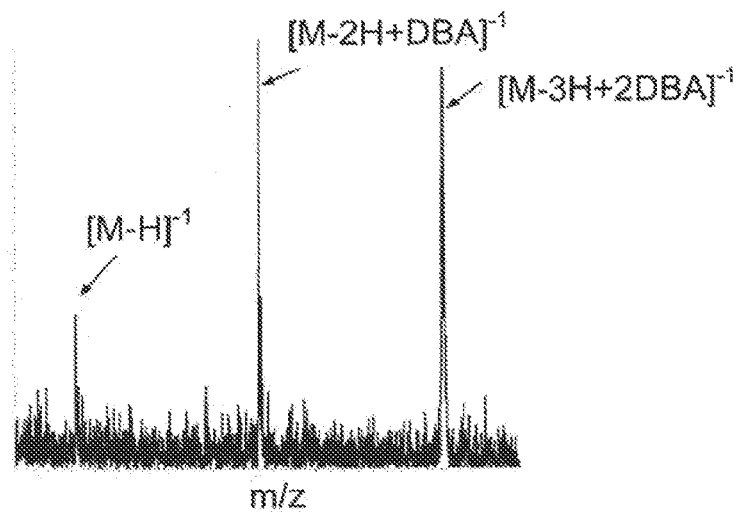
FIG. 30B is an enlarged representation of the '30B' region of FIG. 30A.
Figure 31A:
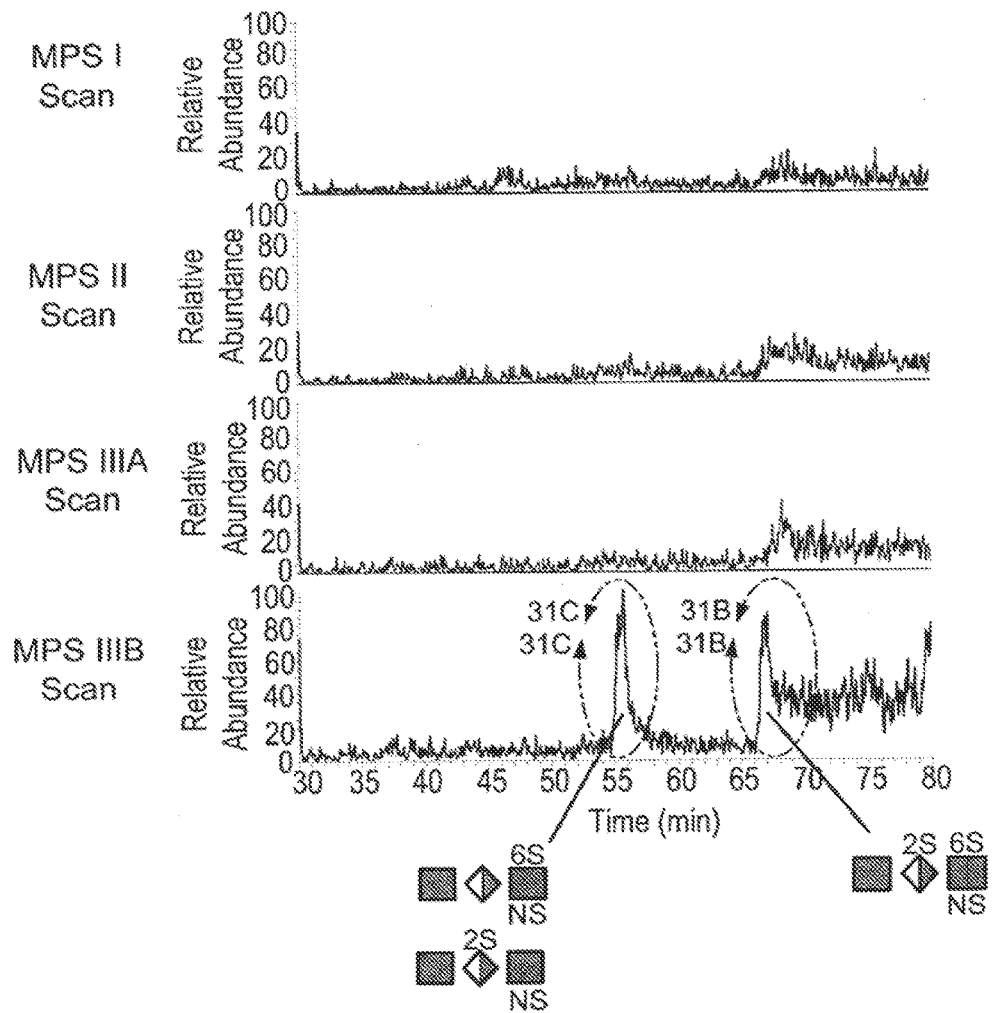
FIG. 31A illustrates mass spectrometry results for non-reducing end oligosaccharides in a MPS IIIB sample.
Figure 31B:
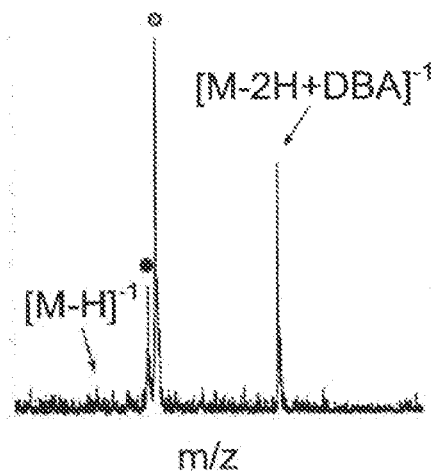
FIG. 31B is an enlarged representation of the '31B' region of FIG. 31A.
Figure 31C:
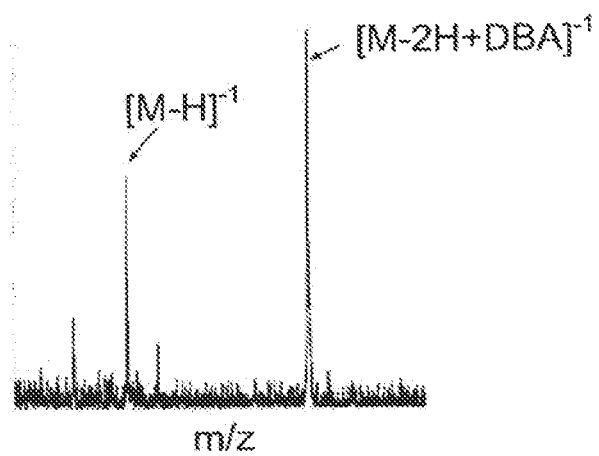
FIG. 31C is an enlarged representation of the '31C' region of FIG. 31A.
Figure 32:
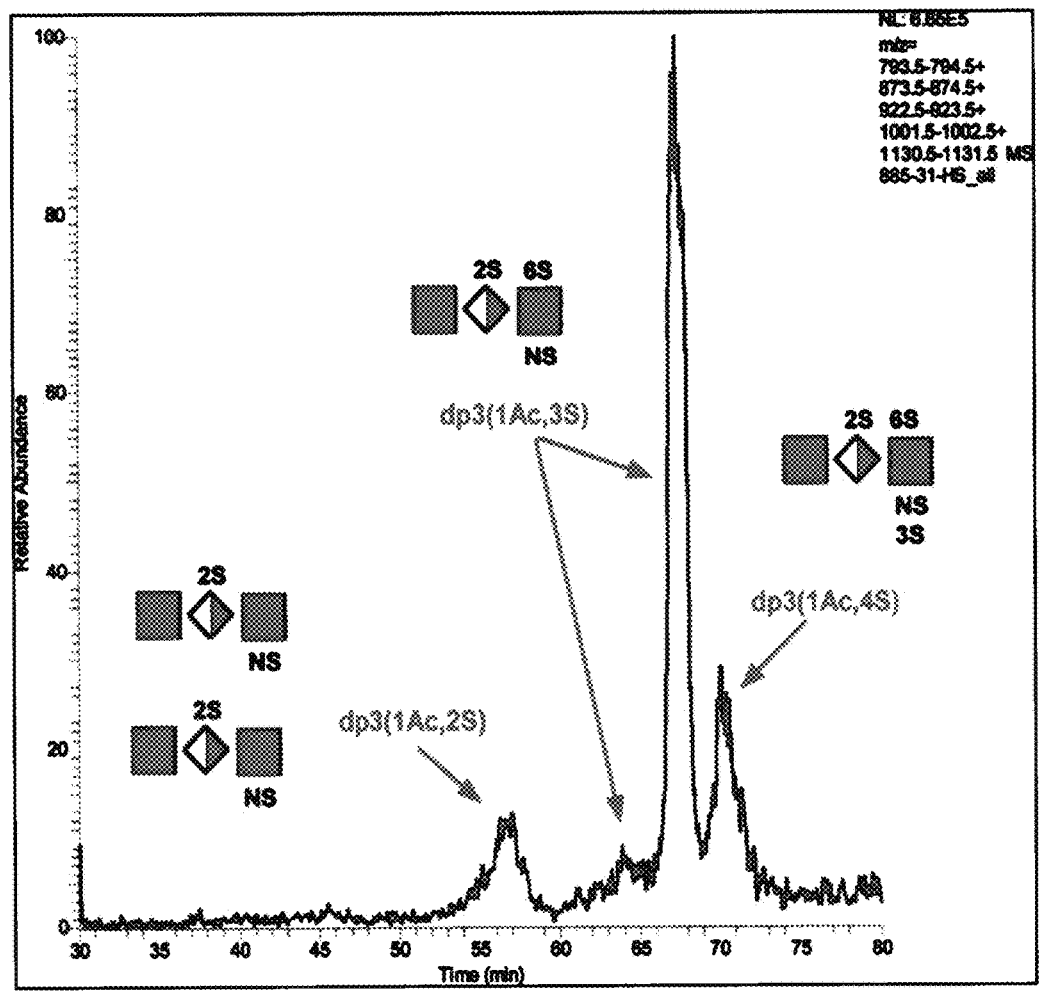
FIG. 32 illustrates mass spectrometry results showing the accumulation of GAG non-reducing end trisaccharide residues in the liver of an MPS IIIB mouse.
Figure 33:
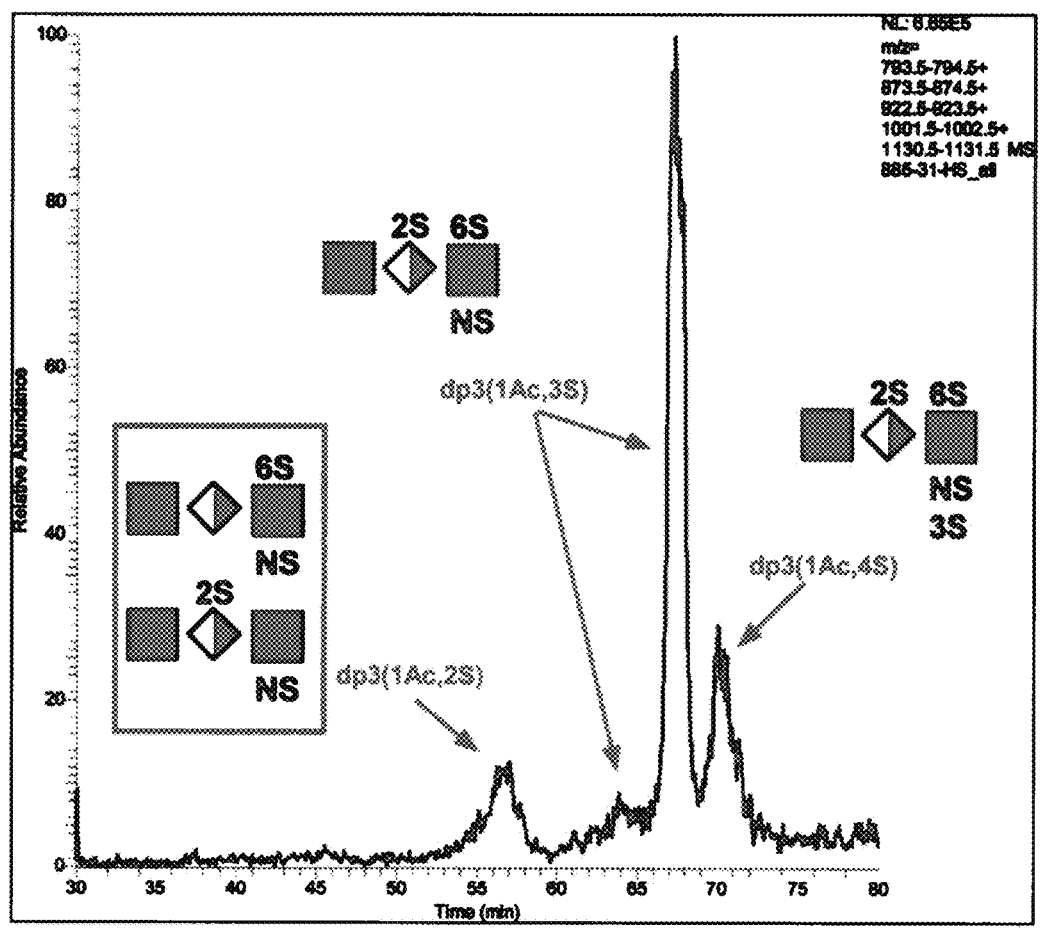
FIG. 33 illustrates mass spectrometry results showing the accumulation of GAG non-reducing end trisaccharide residues in the brain of an MPS IIIB mouse.
Figure 34:
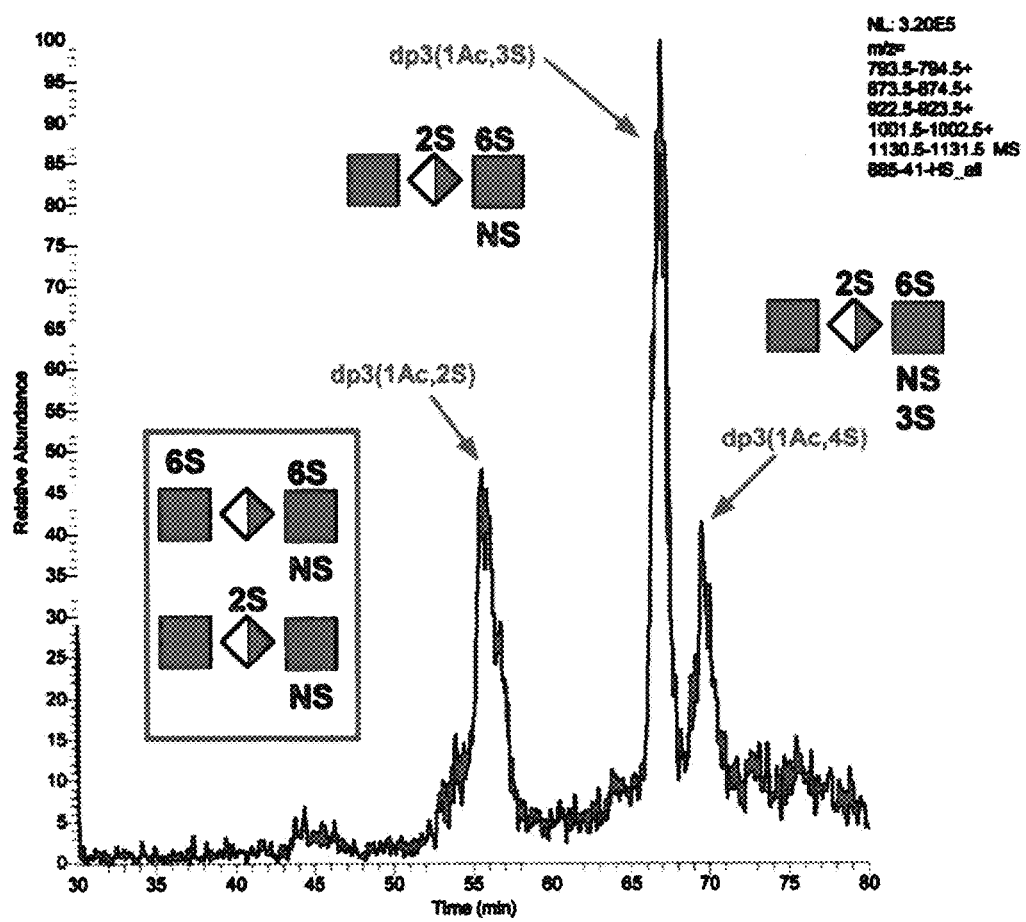
FIG. 34 illustrates mass spectrometry results showing the accumulation of GAG non-reducing end trisaccharide residues in the kidney of an MPS IIIB mouse.

In some instances, a lysosomal storage disease is caused by abnormal glycosaminoglycan degradation. In some instances, a lysosomal storage disease causes an accumulation of heparan sulfate and/or dermatan sulfate (e.g., MPS I)

and is caused by an iduronidase deficiency. In some instances, a lysosomal storage disease causes an accumulation of heparan sulfate and/or dermatan sulfate (e.g., MPS II) and is caused by a 2-sulfatase deficiency. FIG. 26 illustrates accumulation of oligosaccharides in MPS II human fibroblast versus the accumulation of oligosaccharides in normal human fibroblasts. In some instances, a lysosomal storage disease causes an accumulation of heparan sulfate and/or hyaluronan (e.g., MPS IIIB) and is caused by an N-acetylglulcosaminidase deficiency. In some instances, a lysosomal storage disease causes an accumulation of heparan sulfate (e.g., MPS IIIC) and is caused by a glucosamine acetyltransferase deficiency. In some instances, a lysosomal storage disease causes an accumulation of heparan sulfate and/or keratan sulfate (e.g., MPS IIID) and is caused by a N-acetylglucosamine 6-sulfatase deficiency. In some instances, a lysosomal storage disease causes an accumulation of keratan sulfate (e.g., MPS IVA) and is caused by a galactose 6-sulfatase deficiency. In some instances, a lysosomal storage disease causes an accumulation of keratan sulfate (e.g., MPS IVB) and is caused by an N-acetylglactosamine 4-sulfatase deficiency. In some instances, a lysosomal storage disease causes an accumulation of heparan sulfate and/or hyaluronan (e.g., MPS VII) and is caused by a glucuronidase deficiency. In some instances, a lysosomal storage disease causes an accumulation of hyaluronan (e.g., MPS IX) and is caused by a hyaluronidase deficiency.

In some embodiments, a MPS is Hunter's disease. In certain embodiments, Hunter's disease causes an accumulation of dermatan sulfate and heparan sulfate glycosaminoglycans. In certain instances, the accumulation of dermatan sulfate and heparan sulfate glycosaminoglycans in Hunter's disease is associated with a deficiency in a sulfatase. In some embodiments, the MPS is Hurler's disease. In certain instances, Hurler's disease causes an accumulation of dermatan sulfate and heparan sulfate glycosaminoglycans. In some instances, the accumulation of dermatan sulfate and heparan sulfate glycosaminoglycans in Hurler's disease is associated with a deficiency in an iduronidase.

In some embodiments, a disorder associated with abnormal glycosaminoglycan degradation, biosynthesis and/or accumulation is undesired angiogenesis (e.g., angiogenesis associated with cancer, diabetic blindness, age-related macular degeneration, rheumatoid arthritis, or psoriasis), insufficient angiogenesis (e.g., coronary artery disease, stroke, or delayed wound healing), amyloidosis, a spinal cord injury, hypertriglyceridemia, inflammation, or a wound.

In some instances, amyloidosis is present in various diseases including, e.g., Alzheimer's disease, Parkinson's disease, type-2 diabetes, Huntington's disease, spongiform encephalopathies (Creutzfeld-Jakob, Kuru, Mad Cow), diabetic amyloidosis, rheumatoid arthritis, juvenile chronic arthritis, Ankylosing spondylitis, psoriasis, psoriatic arthritis, adult still disease, Becet syndrome, famalial Mediterranean fever, Crohn's disease, leprosy, osteomyelitis, tuberculosis, chronic bronciectasis, Castleman disease, Hodgkin's disease, renal cell carcinoma, carcinoma of the gut, lung or urogenital tract. In some instances, the Alzheimer's disease is associated with changes in the content and structure of one or more GAG (e.g., heparan sulfate, keratan sulfate, or the like).

In some embodiments, disorders associated with abnormal glycosaminoglycan accumulation include disorders associated with abnormal biosynthesis (e.g., polymerization and/or sulfation) of glycosaminoglycans. In certain instances, the abnormal biosynthesis of glycosaminoglycans results in glycosaminoglycans that are not readily degraded by normal glycosaminoglycan degrading enzymes. In some instances, disorders associated with abnormal GAG biosynthesis include osteoarthritis. In certain instances, osteoarthritis is associated with changes in sulfation of chondroitin sulfate, changes in length of chondroitin sulfate, changes in expression levels of chondroitin sulfate, or any combination of thereof. In some instances, osteoarthritis is associated abnormal chondroitin sulfate sulfotransferase. In certain instances, the osteoarthritis is associated with changes in sulfation of dermatan sulfate, changes in length of dermatan sulfate, changes in expression levels of dermatan sulfate, or any combination of thereof. In certain instances, the osteoarthritis is associated with changes in sulfation of keratan sulfate, changes in length of keratan sulfate, changes in expression levels of keratan sulfate, or any combination of thereof.

In some embodiments, a disorder associated with abnormal glycosaminoglycan degradation, biosynthesis and/or accumulation is macular corneal dystrophy. In some instances, macular corneal dystrophy is associated with low amounts of keratan sulfate. In more specific embodiments, the keratan sulfate levels are due to failure to initiate keratan sulfate synthesis, polymerize the keratan sulfate chain length, or any combination thereof.

In some embodiments, a disorder associated with abnormal glycosaminoglycan degradation, biosynthesis and/or accumulation is an infectious or viral disease. In some embodiments, the infectious or viral disease includes herpes, diphtheria, papilloma virus, hepatitis, HIV, coronavirus, or adenovirus.

In some embodiments, a disorder associated with abnormal glycosaminoglycan degradation, biosynthesis and/or accumulation is a cancer. In certain embodiments, the cancer is breast cancer, ovarian cancer, colorectal cancer, cervical cancer, pancreatic cancer, gastric cancer, esophageal cancer, head and neck cancer, hepatocellular cancer, prostate cancer, melanoma, osteosarcoma, endometrial cancer, multiple myeloma, gastric cancer, lung cancer, glioma, kidney cancer, bladder cancer, thyroid cancer, neuroblastoma, or non-Hodgkin lymphoma.

In certain instances, cancer is associated with abnormal heparan sulfate depolymerization and degradation that results in unbound, accumulated heparan sulfate. In some instances, abnormal heparan sulfate depolymerization and degradation is associated with melanomas, gliomas, multiple myelomas, ovarian, breast, colon, cervical, pancreatic, gastric, and esophageal cancers. In certain instances, abnormal heparan sulfate depolymerization and degradation contributes to angiogenesis, metastasis and growth factor mobilization. In some instances, the abnormal heparan sulfate depolymerization and degradation is from increased activity of a heparanase.

In certain instances, cancer is associated with abnormal heparan sulfate sulfation that results in accumulated heparan sulfate. In some instances, abnormal heparan sulfate sulfation is associated with colon carcinoma, myeloma, ovarian cancer, hepatocellular carcinoma, head and neck squamous cell carcinoma and prostate cancer. In some instances, heparan sulfate sulfation is decreased in certain cancers, while in other embodiments; the heparan sulfate sulfation is increased. In some instances, abnormal heparan sulfate sulfation is caused by abnormal heparan sulfate sulfotransferase function.

In certain instances, cancer is associated with abnormal chondroitin sulfate sulfation. In more specific embodiments, the abnormal chondroitin sulfate sulfation is associated with lung cancer. In some instances, the chondroitin sulfate sulfation is increased in certain cancers. In certain instances, the abnormal chondroitin sulfate sulfation is caused by abnormal chondroitin sulfate sulfotransferase function. In some instances, increased production of chondroitin sulfate is associated in breast cancer, melanoma, and transformed fibroblasts.

In certain instances, cancer is associated with dermatan sulfate epimerase expression. In some instances, the dermatan sulfate epimerase expression is increased in squamous cell carcinoma, glioma, gynecological cancer, pancreatic cancer, colorectal carcinoma, and prostate cancer. In certain instances, the cancer is associated with accumulation of dermatan sulfate levels. In some instances, the dermatan sulfate levels are increased in pancreatic cancer.

In certain instances, cancer is associated with abnormal keratan sulfate sulfation. In some instances, the abnormal keratan sulfate sulfation is associated with glioblastomas. In certain instances, abnormal keratan sulfate sulfation is caused by abnormal keratan sulfate sulfotransferase function. In some instances, keratan sulfate expression is increased in glioblastomas.

In certain instances, cancer is associated with abnormal hyaluronan accumulation. In some instances, abnormal hyaluronan accumulation is associated with breast cancer, prostate cancer, aggressive subtypes of non-Hodgkin lymphoma, and colorectal cancer. In certain instances, hyaluronan accumulation contributes to metastasis of certain cancers. In some instances, the hyaluronan accumulation results from the over expression of a hyaluronan synthase.

Drug Screens

Provided in certain embodiments herein is a process for identifying an agent that inhibits the accumulation of glycosaminoglycans in a cell, the process comprising:
a. contacting a plurality of mammalian cells with a compound, the plurality of mammalian cells being of a cell line that accumulates an abnormal amount of glycosaminoglycans;
b. incubating the mammalian cells with the compound;
c. optionally transforming the mammalian cells e.g., by isolating a population of glycosaminoglycans from the cells (e.g., using any suitable method described herein);
d. contacting the mammalian cells and/or the isolated population of glycosaminoglycans from step (c) with a GAG lyase (e.g., heparin lyase);
e. purifying a sub-population of oligosaccharides from step (d) (e.g., using any suitable method described herein);
f. detecting the presence of and/or measuring the amount of one or more oligosaccharides present in the sub-population (e.g., using LC-MS or GC-MS); and
g. displaying or recording a characterization of the sub-population of one or more oligosaccharides.

In certain instances, the mammalian cells are optionally transformed by e.g., tagging a population of glycosaminoglycans on and/or in the cells with a detectable label. In some instances, the mammalian cells are optionally transformed by e.g., isolating a population of glycosaminoglycans on and/or in the cells using any suitable purification technique described herein.

In certain embodiments, the cell is present in an individual (e.g., a human or other mammal) and is incubated at body temperature. In some embodiments, the cell line that accumulates an abnormal amount of glycosaminoglycans being a mucopolysaccharidosis (MPS) cell line (e.g., a human MPS cell line). In more specific embodiments, the MPS cell line is a cell line for MPS I, MPS II, MPS IIIA, MPS IIIB, MPS IIIC, MPS IIID, MPS IVA, MPS IVB, MPS VI, MPS VII, MPS IX, or a combination thereof. In some embodiments, the human MPS cell line is present in a human or other mammal. In some embodiments, inhibitors of the accumulation of glycosaminoglycans are compounds that reduce the rate of accumulation of glycosaminoglycans in the cell, and/or agents that reduce the total amount of glycosaminoglycans accumulated in the cell (i.e., diminish the amount of glycosaminoglycan that has been accumulated in the cell). Agents that are optionally tested for the screening process described herein include any compound such as, by way of non-limiting example, a polynucleotide (e.g., siRNA), a polypeptide, or a small molecule compound (e.g., having a molecular weight of less than 2,000 g/mol).

EXAMPLES

Example 1

Purification

The biological sample (cells, tissue, blood, serum, or the like) is homogenized and solubilzed in 0.1-1.0 N NaOH (e.g., 0.1 N, 0.2 N, 0.3 N, 0.4 N, 0.5 N, 0.6 N, 0.7 N, 0.8 N, 0.9 N, or 1.0 N) or acetic acid and then neutralized with acetic acid or NaOH. Next a small sample is taken to measure protein content of the sample using standard methods. 0.01-0.5 mg/mL (0.01 mg/mL, 0.07 mg/mL, 0.12 mg/mL, 0.17 mg/mL, 0.22 mg/mL, 0.27 mg/mL, 0.32 mg/mL, 0.37 mg/mL, 0.42 mg/mL, or 0.5 mg/mL) protease (trypsin, chymotrypsin, pepsin, pronase, papain, or elastase) is treated in 0.1-0.5 M (e.g., 0.1 M, 0.16 M, 0.23 M, 0.32 M, 0.39 M, 0.44 M, or 0.5 M) NaCl, 0.01-0.1 M (e.g., 0.01 M, 0.02 M, 0.04 M, 0.06 M, 0.08 M, 0.1 M) NaOAc, at pH 5.5-7.5 (e.g., 5.5, 6.0, 6.5, 7.0, or 7.5) and 25-40 C (e.g., 25 C, 30 C, 35 C, or 40 C) for 1-24 hours (e.g., 1 h, 2 h, 4 h, 6 h, 8 h, 12 h, 18 h, 24 h). The sample is diluted to reduce the ionic strength and loaded onto an ion exchange column in 5-100 mM (e.g., 5 mM, 10 mM, 20 mM, 30 mM, 40 mM, 50 mM, 60 mM, 70 mM, 75 mM, 80 mM, 90 mM, 95 mM, 100 mM) NaOAc pH 5-7 with 0-300 mM NaCl. After washing, the bound glycosaminoglycans are eluted with 5-100 mM NaOAc pH 5-7 (e.g., 5, 5.5, 6, 6.5, 7) with 0.8-3M (e.g., 0.8 M, 1 M, 1.2 M, 1.4 M, 1.6 M, 1.8 M, 2 M, 2.5 M, or 3 M) NaCl. The eluted glycans are then concentrated and desalted by ethanol precipitation, size exclusion, or other methods. The purified glycans are dried for further analysis.

Example 2

Digestion

Lyase digestion: The purified glycans are resuspended in 10-300 mM sodium acetate, tris, phosphate, or other suitable buffer, 0.02-1 mM (e.g., 0.02, 0.04, 0.06, 0.08, 0.1, 0.2, 0.3, 0.4, 0.5, 0.6, 0.7, 0.8, 0.9, or 1) calcium acetate, pH 5-8 (e.g., 5, 5.5, 6, 6.5, 7, 7.5, or 8), were digested with heparin lyases I, II, III, I and II, I and III, II and III, or I, II, and III (0.0.15-1.5 milliunits of each in 100-ul reactions, IBEX, Montreal, Canada) at 25 to 37° C. for 1 to 24 hours.

Example 3

Tagging

Dried glycan sample is re-suspended in 2-100 μL 0.003-0.1 M (e.g., 0.003 M, 0.003 M, 0.03 M, 0.06 M, 0.1 M) AB, AA, AMAC, or Bodipy dye and incubated at room temperature for 1-120 minutes (e.g., 1-10 min, 10-15 min, 15-20 min, 20-25 min, 25-30 min, 30-40 min, 40-50 min, 50-60 min, 60-90 min, 90-120 min). Next, the reaction is initiated with 2-100 μL (2 μL, 5 μL, 10 μL, 15 μL, 20 μL, 25 μL, 30 μL, 40 μL, 50 μL, 60 μL, 70 μL, 80 μL, 90 μL, or 100 μL) 1 M NaCNBH$_4$ and the reaction is allowed to proceed at 25-100 C. (e.g., 25 C, 30 C, 35 C, 40 C, 50 C, 60 C, 70 C, 80 C, 90 C, 100 C).

Example 4

Detecting

HPLC separation of tagged saccharides was performed utilizing the following conditions:
Column types: 130A BEH particle Phenyl (1.7, 2.5, 3.5, 5, or 10 uM particle size), 130A BEH particle C18 (1.7, 2.5, 3.5, 5, or 10 uM particle size), HSS particle C18 (1.8, 3.5, or 5 uM particle size), or 300A BEH particle C18 (1.7, 3.5, 5, 10 uM particle size) with suitable length and internal diameter.
Buffer Conditions:
  A=10 mM Ammonium Acetate with 0-20% methanol
  B=100% Methanol
  Initial Conditions: 70-95% A, 0-30% B
Flow Rate is constant at 0.05-1 ml/min
Runs a gradient down to 70-90% A, 10-30% B over 5-65 min.
At 8.1 min runs a gradient to 0-20% A, 80-100% B over 5-20 min.
5-65 min returns to initial conditions
Fluorescently tagged oligosaccharides (disaccharides) were detected at various elution times depending on the specific marker produced of interest. Elution order of unsaturated disaccharide standards was:
  2SNS6S
  NS6S
  2SNS
  NS
  NA6S
  NA Example 5

Tested was the ability of a non-reducing end detection method to identify and classify MPS samples by blindly analyzing normal and MPS GAGs from cultured fibroblasts. Human primary fibroblast cultures from MPS patients with MPS I, II, IIA, and IIIB (GM01256, GM00298, GM00879, and GM01426, respectively) were obtained from the NIGMS Human Genetic Cell Repository. Cells were seeded at high density and allowed to accumulate GAGs for 7-14 days. At harvest, GAGs were isolated using the procedure described in the specifications. Total GAGs were digested with heparin lyases to completion. A portion of the digested GAG fragments were analyzed by liquid chromatography tandem atmospheric pressure electrospray mass spectrometry of aniline derivatized oligosaccharides to determine if the diagnostic biomarkers were present. FIGS. 27, 28A, 29A, 30A and 31A—Panel A shows representative structures of predicted oligosaccharides for each class of MPS. FIGS. 27, 28A, 29A, 30A and 31A—Panels B, C, D, and E show the extracted ion currents for representative biomarker(s) for MPS I (m/z=590.5-591.5+719.5-720.5), MPS II (m/z=719.5-720.5+799.5-800.5), MPS IIIA (m/z=831.5-832.5+960.5-961.5+1088.5-1089.5), and MPS IIIB (m/z=793.5-794.5+873.5-874.5+922.5-923.5+1002.5-1003.5+1130.5-1131.5), respectively. MS analysis was done according to the methods of Lawrence et al. J Biol Chem. 2008 Nov. 28; 283(48):33674-84. Insets are the corresponding MS spectra for the non-reducing end structures detected. By combining the known degradative defect with the mass spectrometry data, the actual structures of the biomarkers can be deduced or reduced to a few likely structures. The sensitivity of the method to detect and correctly identify MPS disease from small cell culture samples indicates that this method has the sensitivity to work on clinically relevant samples such as blood or urine.

Example 6

The non-reducing end biomarker method was used to measure the accumulation of GAGs in the MPS IIIB mouse model. Previous reports have had difficulty measuring GAG accumulation in the brain, despite microscopic validation of lysosomal inclusions. This has been especially puzzling because the primary phenotype in MPS IIIB patients are neurological symptoms. We used this challenging case to determine if this biomarker method can detect GAG accumulation in difficult tissues. 20 mg (wet weight) tissue samples were homogenized and total cellular GAGs were purified using the method described in the specifications. The purified GAGs were them treated with heparin lyases to liberate the unique non-reducing ends from the heterogeneous collection of fragments. The presence of the MPS IIIB biomarkers {(dp3-1Ac,2S), (dp3(1Ac,3S), and (dp3(1Ac,4S)} was analyzed by LC-MS. These studies verify that the GAG accumulation is occurring in the brain.

Example 7

Diagnosing Disease

The following data is generated by measuring the abundance of a saturated disaccharide liberated from GAGs by heparin lyases that accumulate in MPS I samples. Using the described method, the analyzed saturated disaccharide elutes at 3.07 minutes.

Example 7A

Figure 35:
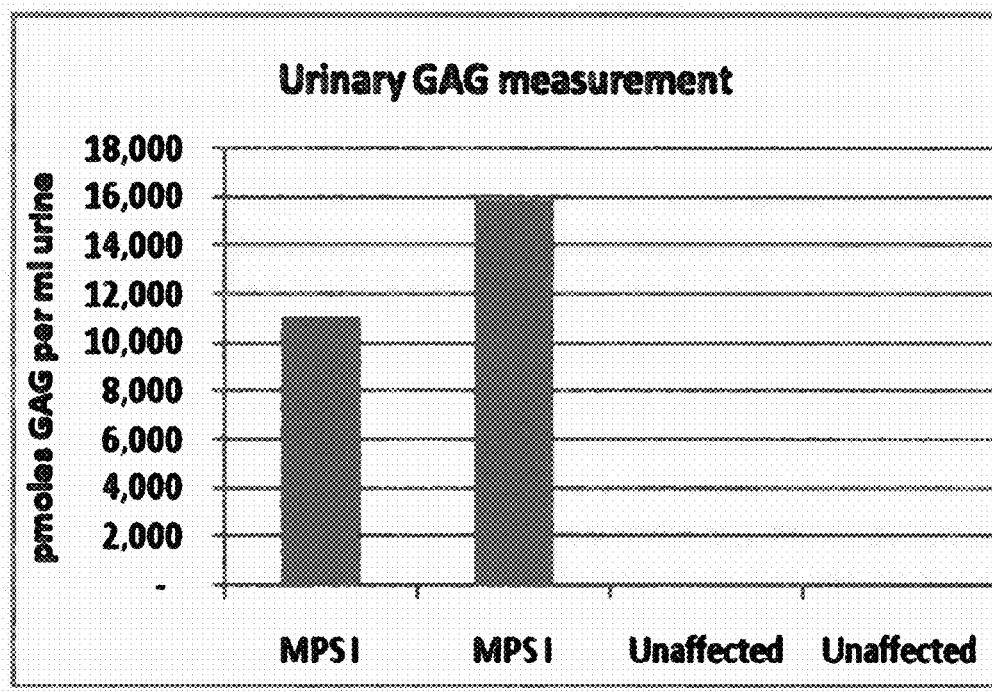
FIG. 35 illustrates the detection of MPS disease in urine samples.

In these studies, 9 μL frozen urine samples from MPS I affected dogs and carrier dogs (unaffected) were analyzed for the presence of saturated disaccharide liberated from the non-reducing end of the disease causing glycans. Picomoles of saturated disaccharide per milliliter of serum are shown in FIG. 35. FIG. 35 illustrates that the assay is useful for detecting the presence of MPS disease in urine samples.

Example 7B

Figure 36:
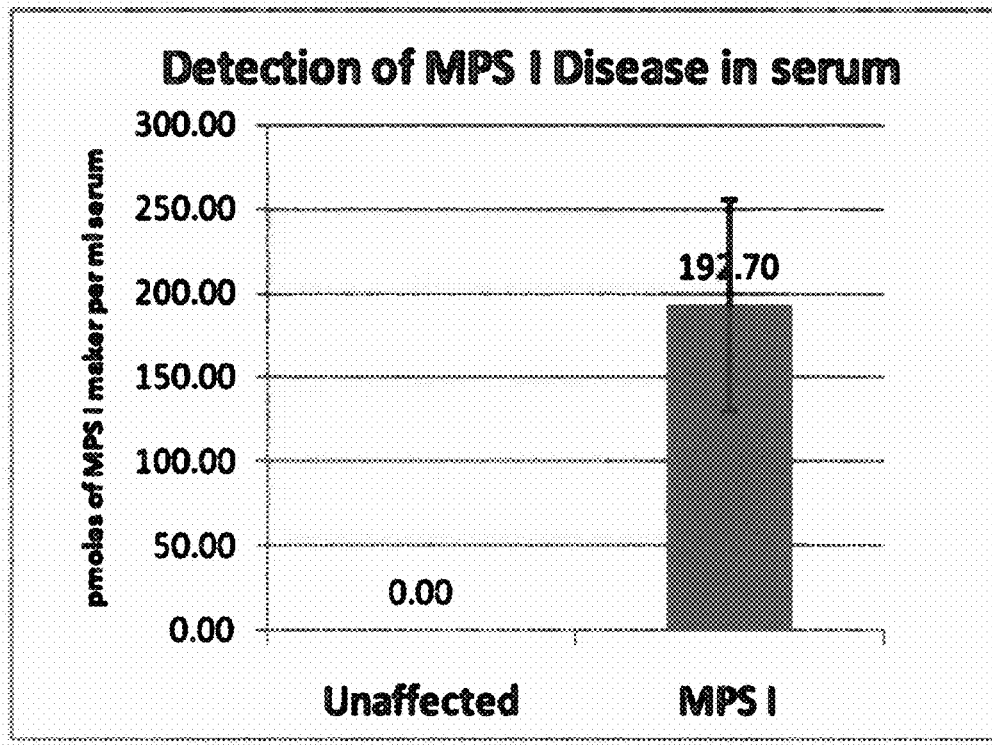
FIG. 36 illustrates the detection of MPS disease in serum samples.

In these studies 30 μL frozen serum samples from MPS I affected dogs and carrier dogs (unaffected) were analyzed for the presence of saturated disaccharide liberated from the non-reducing end of the disease causing glycans. Picomoles of saturated disaccharide per milliliter of serum are shown in FIG. 36. FIG. 36 illustrates that this assay is useful for identifying the presence of MPS (e.g., MPS I) disease in serum. By using the unique markers appropriate for other MPS classes, the same is accomplished for other MPS classes.

Example 7C

Figure 37:
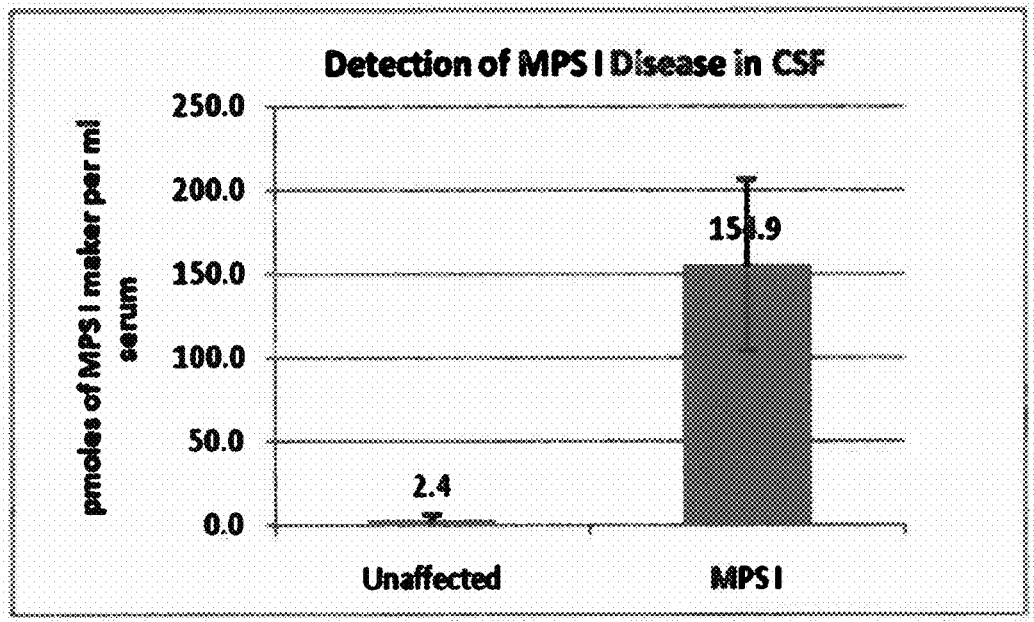
FIG. 37 illustrates the detection of MPS disease in CSF samples.

In these studies 30 μL frozen CSF samples from MPS I affected dogs and carrier dogs (unaffected) were analyzed for the presence of saturated disaccharide liberated from the non-reducing end of the disease causing glycans. Picomoles of saturated disaccharide per milliliter of CSF are shown in FIG. 37. FIG. 37 illustrates that this method is useful for detecting disease in CSF from MPS patients.

Example 7D

Figure 38:
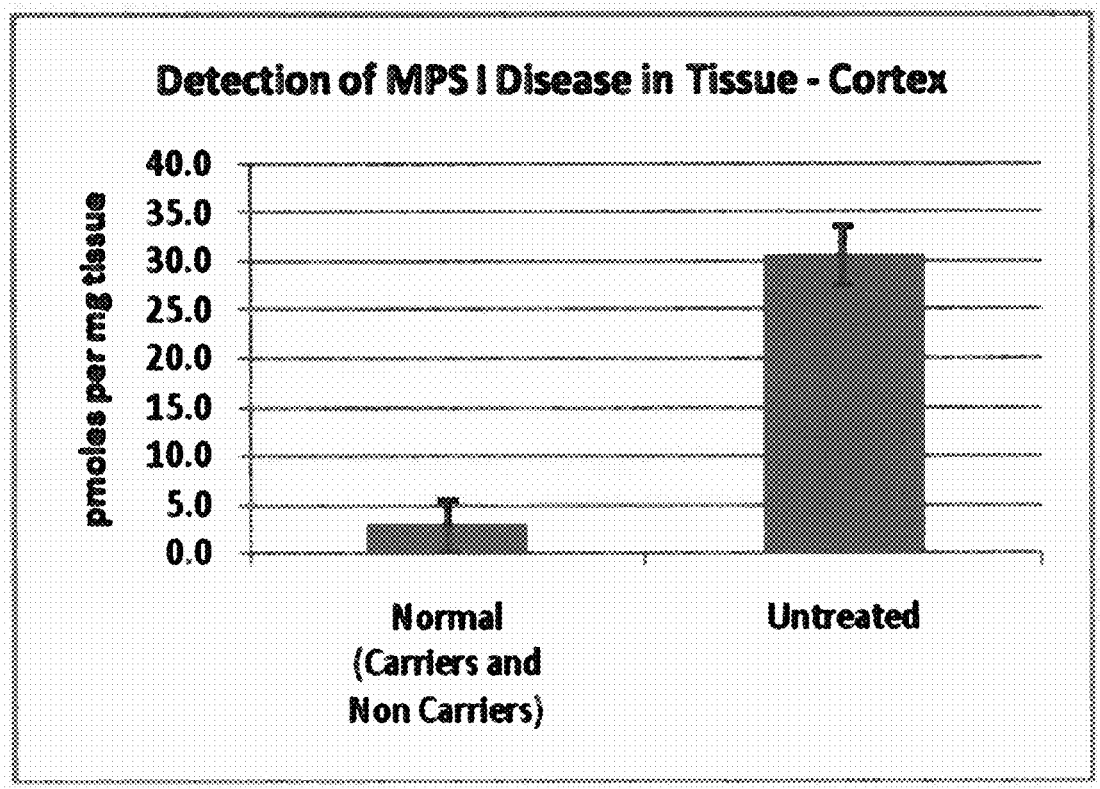
FIG. 38 illustrates the detection of MPS disease in tissue samples.

To determine if the GAG accumulation assay described here is able to detect MPS I disease in tissue samples, we analyzed the GAG accumulation in 2.5 mg samples of cortex taken from unaffected and affected MPS I dogs. Samples were analyzed for the presence of saturated disaccharide liberated from the non-reducing end of the disease causing glycans. Picomoles of saturated disaccharide per milligram of cortex are shown in FIG. 38. FIG. 38 illustrates this method is useful for detecting MPS disease in tissue samples from patients.

Example 8

Diagnosing Severity of Disease

The following data is generated by measuring the abundance of a saturated disaccharide liberated from GAGs by heparin lyases that accumulate in MPS I samples. Using the described method, this analyzed saturated disaccharide elutes at 3.07 minutes.

Figure 39:
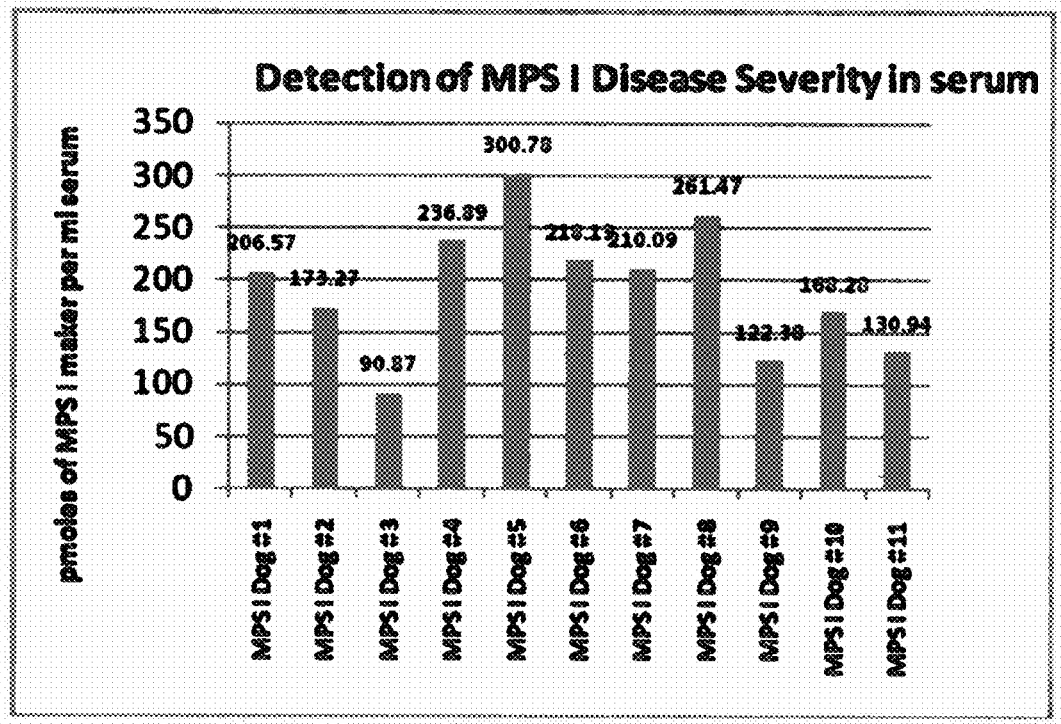
FIG. 39 illustrates monitoring and detecting the response to therapy in serum from MPS patients.

In these studies 30 µL frozen serum samples from MPS I affected dogs were analyzed to measure the level of GAG accumulation in each dog. Because the MPS I dog model is a naturally occurring and genetically heterogeneous model, there is significant variation in disease severity between individual dogs. These differences in disease severity are revealed by variations in the level of GAG accumulation between the individual dogs using the methods described here. Samples were analyzed for the presence of saturated disaccharide liberated from the non-reducing end of the disease causing glycans. Picomoles of saturated disaccharide per milliliter of serum are shown in FIG. 39. FIG. 39 illustrates that this method can be used to detect the response to therapy in serum from MPS patients.

Example 9

Monitoring Response to Therapy

The following data is generated by measuring the abundance of a saturated disaccharide liberated from GAGs by heparin lyases that accumulate in MPS I samples. Using the described method, this analyzed saturated disaccharide elutes at 3.07 minutes.

Example 9A

Figure 40:
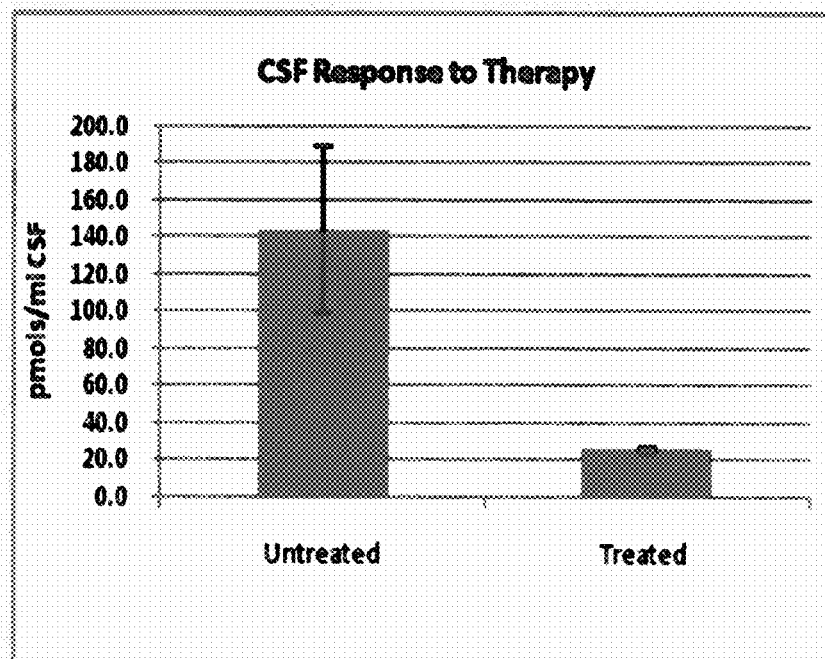
FIG. 40 illustrates monitoring and detecting MPS disease severity.

In these studies 30 µL frozen CSF samples from MPS I affected dogs before treatment (untreated) and after monthly intrathecal (IT) treatment with laronidase (treated). Samples were analyzed for the presence of saturated disaccharide liberated from the non-reducing end of the disease causing glycans. Picomoles of saturated disaccharide per milliliter of CSF are shown in FIG. 40. FIG. 40 illustrates that this method is useful for detecting the response to therapy in CSF from MPS patients.

Example 9B

Figure 41:
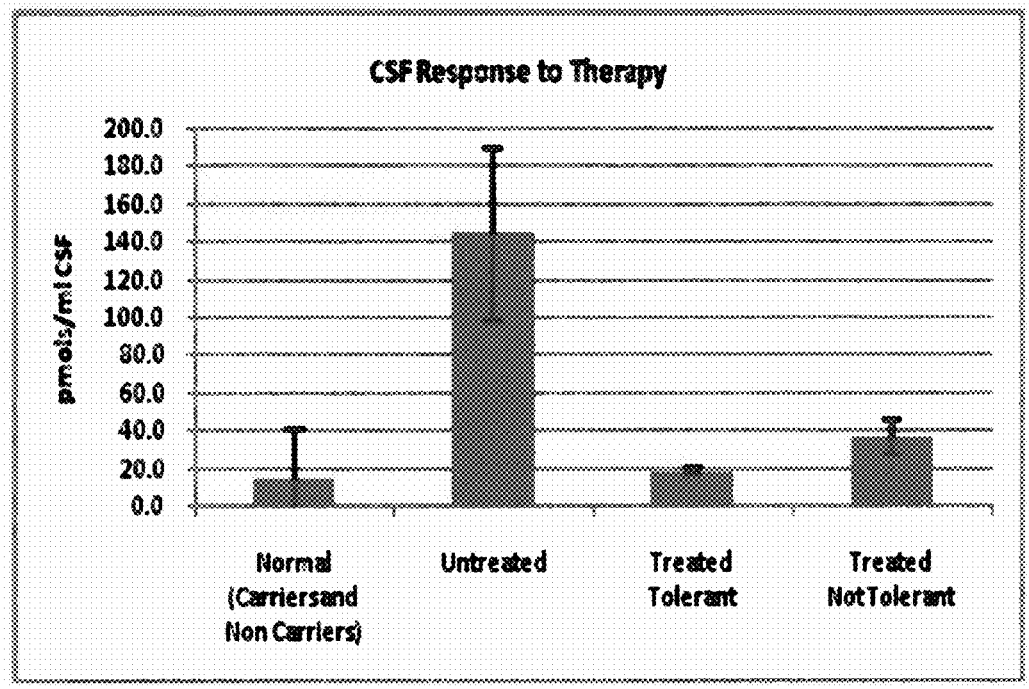
FIG. 41 illustrates monitoring and detecting the differential response to therapy in CSF from MPS patients.

To determine if the GAG accumulation assay described here is able to measure different levels of response to treatments, a group of MPS I dogs who were treated with IT laronidase were analyzed with respect to their level of therapy directed antibodies. "Tolerant" dogs are dogs that do not mount a significant immune reaction to the laronidase treatment while "not tolerant" dogs mount a significant antibody response. This antibody response is expected to reduce the efficacy of the enzyme replacement therapy, laronidase. To determine if the assay can detect this differential response, 30 µL frozen CSF samples from MPS I affected dogs before treatment (untreated) and after monthly intrathecal (IT) treatment with 0.58 mg/kg laronidase (treated). Samples were analyzed for the presence of saturated disaccharide liberated from the non-reducing end of the disease causing glycans and summarized with respect to their tolerance class. The response to therapy is shown for three different dogs affected with MPS I. Picomoles of saturated disaccharide per milliliter of CSF are shown in FIG. 41. FIG. 41 illustrates that this method is useful for detecting the differential response to therapy in CSF from MPS patients. In some embodiments, this process is used to guide the treatment for individual patients.

Example 9C

Figure 42:
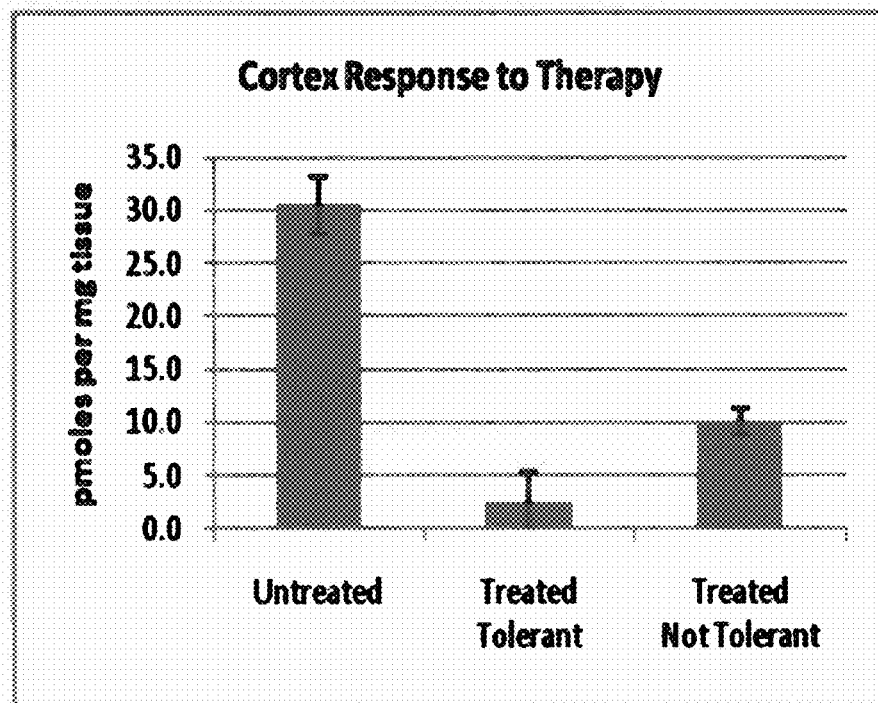
FIG. 42 illustrates monitoring and detecting response to therapy in tissue samples from MPS patients.

To determine if the GAG accumulation assay described here is able to detect a response to therapy in MPS I disease in tissue samples treated with IT laronidase, we analyzed the GAG accumulation in 2.5 mg samples of cortex taken from unaffected and affected MPS I dogs. Differential response to therapy is seen based on the tolerance status of the specific dogs. Samples were analyzed for the presence of saturated disaccharide liberated from the non-reducing end of the disease causing glycans and summarized with respect to their tolerance class. The response to therapy is shown for three different dogs affected with MPS I. Picomoles of saturated disaccharide per milliliter of CSF are shown in FIG. 42. FIG. 42 illustrates that this method is useful for detecting response to therapy in tissue samples from patients.

Example 9D

Figure 43A:
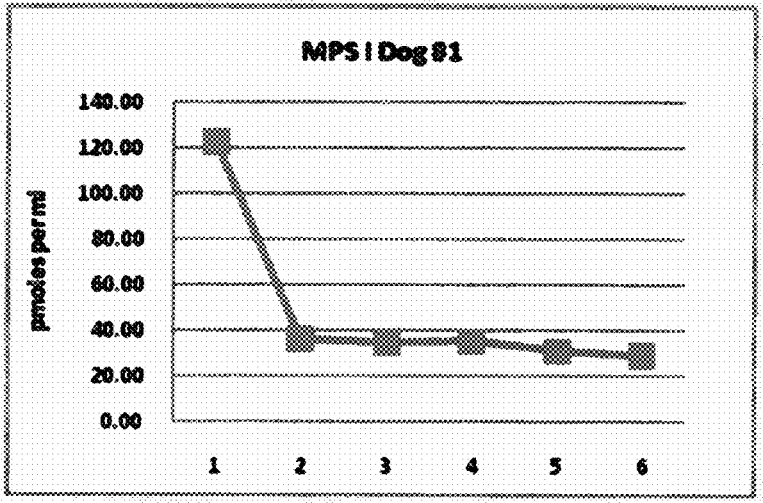
FIGS. 43A, 43B, and 43C illustrate monitoring and detecting the response to therapy in serum from individuals suffering from MPS.
Figure 43B:
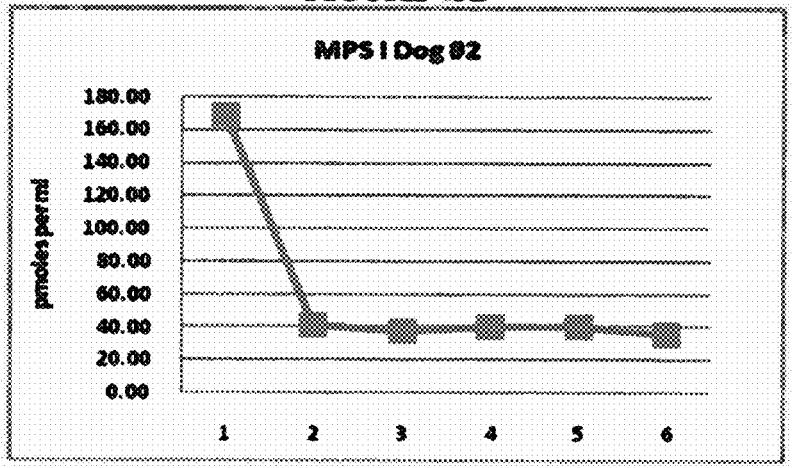
Figure 43C:
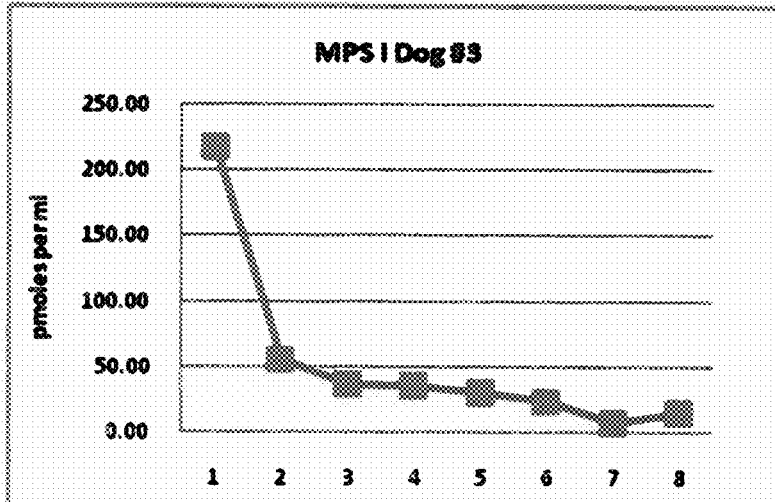

In these studies 30 µL frozen serum samples from MPS I affected dogs before treatment (sample #1) and monthly samples through weekly IV treatment with laronidase (samples #2, 3, 4 etc.). Serum samples were taken immediately prior to the next IV infusion. Samples were analyzed for the presence of unsaturated disaccharides liberated from the non-reducing end of the disease causing glycans. The response to therapy is shown for three different dogs affected with MPS I. Picomoles of these structures per milliliter of serum are shown in FIG. 43A, 43B, and 43C. FIG. 43A, 43B, and 43C illustrate that this method is useful for detecting the response to therapy in serum from MPS patients.

Example 10

Diagnosing Carriers

To determine if the GAG accumulation assay described here is able to detect carriers of the genetic cause of MPS, we analyzed wild-type dogs and dogs that are heterozygous for the MPS I causing mutation. Carriers are presumed to lack any clinical manifestation of MPS I; however, it is possible that the partial deficiency in a lysosomal enzyme will lead to low levels of GAG accumulation that can be detected with this assay. Samples were analyzed for the presence of unsaturated saturated disaccharide liberated from the non-reducing end of the disease causing glycans and summarized with respect to their tolerance class. Picomoles of saturated disaccharide per milligram of tissue are shown in FIG. 44. FIG. 44 illustrates that the method described herein is useful for detecting carriers of the genetic cause of MPS.

What is claimed is:

1. A method of determining in an individual the presence, identity, and/or severity of an MPS III disorder, the method comprising:
    (a) generating a biomarker comprising one or more saturated non-reducing end oligosaccharides, wherein the biomarker is generated by treating a population of heparan sulfate oligosaccharides, in or isolated from a biological sample from the individual, with at least one digesting glycosaminoglycan lyase, wherein prior to lyase treatment, the biomarker is not present in abundance in samples from individuals with the MPS III disorder relative to individuals without the MPS III disorder; and
    (b) using an analytical instrument to detect the presence of and/or measure the amount of the biomarker produced and displaying or recording the presence of or the measure of the biomarker produced;
    wherein the presence of and/or measure of the amounts of the biomarker are utilized to determine the presence, identity, and/or severity of the MPS III disorder; and
    wherein the biomarker is selected from a group consisting of
    Formula III: $[GlcNS\text{-}IdoA\text{-}GlcN(Ac)_{0\text{-}1}](SO_3R)_{0\text{-}3}$;
    Formula IV: $[GlcNS\text{-}GlcA\text{-}GlcN(Ac)_{0\text{-}1}](SO_3R)_{0\text{-}2}$;
    Formula V: $[GlcNAc\text{-}IdoA\text{-}GlcN(Ac)_{0\text{-}1}](SO_3R)_{0\text{-}3}$;
    Formula VI: $[GlcNAc\text{-}GlcA\text{-}GlcN(Ac)_{0\text{-}1}](SO_3R)_{0\text{-}2}$;
    Formula VIII: $[GlcN\text{-}GlcA\text{-}GlcN(Ac)_{0\text{-}1}](SO_3R)_{0\text{-}4}$;
    Formula IX: $[GlcNAc6S\text{-}IdoA\text{-}GlcN(Ac)_{0\text{-}1}](SO_3R)_{0\text{-}3}$;
    Formula X: $[GlcNAc6S\text{-}GlcA\text{-}GlcN(Ac)_{0\text{-}1}](SO_3R)_{0\text{-}2}$;
    GlcN-IdoA-GlcNAc;
    GlcN-IdoA2S-GlcNAc;
    GlcN-IdoA-GlcNS;
    GlcN-IdoA-GlcNAc6S;
    GlcN-IdoA2-GlcNAc6S; and
    GlcN-IdoA-GlcNS6S.

2. The method of claim 1, wherein the biomarker is of Formula V: $[GlcNAc\text{-}IdoA\text{-}GlcN(Ac)_{0\text{-}1}](SO_3R)_{0\text{-}3}$; or Formula VI: $[GlcNAc\text{-}GlcA\text{-}GlcN(Ac)_{0\text{-}1}](SO_3R)_{0\text{-}2}$.

3. The method of claim 2, wherein the biomarker of Formula V is selected from a group consisting of GlcNAc-IdoA-GlcNAc, GlcNAc-IdoA2S-GlcNAc, GlcNAc-IdoA-GlcNS, GlcNAc-IdoA2S-GlcNS, GlcNAc-IdoA-GlcNAc6S, GlcNAc-IdoA2S-GlcNAc6S, GlcNAc-IdoA-GlcNS6S, and GlcNAc-IdoA2S-GlcNS6S.

4. The method of claim 2, wherein the biomarker of Formula VI is selected from a group consisting of GlcNAc-GlcA-GlcNAc, GlcNAc-GlcA-GlcNS, GlcNAc-GlcA-GlcNAc6S, and GlcNAc-GlcA-GlcNS6S.

5. The method of claim 1, wherein the method further comprises purifying the biomarker generated in step (a) to yield an isolated population of biomarkers.

6. The method of claim 5, wherein the biomarker is purified using chromatography or electrophoresis.

7. The method of claim 1, wherein the method further comprises tagging the biomarkers with a detectable label.

8. The method of claim 7, wherein the detectable label is a mass label, a radio label, a fluorescent label, a chromophore label, or affinity label.

9. The method of claim 1, wherein the method is used to determine whether the individual is a heterozygous carrier of the MPS III disorder.

10. A method for determining response to a therapy in an individual having an MPS III disorder, the method comprising:
    (a) generating a biomarker comprising one or more saturated non-reducing end oligosaccharides, wherein the biomarker is generated by treating a population of heparan sulfate oligosaccharides, in or isolated from a biological sample from the individual, with at least one digesting glycosaminoglycan lyase, wherein prior to lyase treatment, the biomarker is not present in abundance in samples from individuals with the MPS III disorder relative to individuals without the MPS III disorder; and
    (b) using an analytical instrument to detect the presence of and/or measure the amount of the biomarker produced and displaying or recording the presence of or the measure of the biomarker produced;
    wherein the presence of and/or measure of the amounts of the biomarker are utilized to monitor the treatment of the MPS III disorder; and
    wherein the biomarker is selected from a group consisting of
    Formula III: $[GlcNS\text{-}IdoA\text{-}GlcN(Ac)_{0\text{-}1}](SO_3R)_{0\text{-}3}$;
    Formula IV: $[GlcNS\text{-}GlcA\text{-}GlcN(Ac)_{0\text{-}1}](SO_3R)_{0\text{-}2}$;
    Formula V: $[GlcNAc\text{-}IdoA\text{-}GlcN(Ac)_{0\text{-}1}](SO_3R)_{0\text{-}3}$;
    Formula VI: $[GlcNAc\text{-}GlcA\text{-}GlcN(Ac)_{0\text{-}1}](SO_3R)_{0\text{-}2}$;
    Formula VIII: $[GlcN\text{-}GlcA\text{-}GlcN(Ac)_{0\text{-}1}](SO_3R)_{0\text{-}4}$;
    Formula IX: $[GlcNAc6S\text{-}IdoA\text{-}GlcN(Ac)_{0\text{-}1}](SO_3R)_{0\text{-}3}$;
    Formula X: $[GlcNAc6S\text{-}GlcA\text{-}GlcN(Ac)_{0\text{-}1}](SO_3R)_{0\text{-}2}$;
    GlcN-IdoA-GlcNAc;
    GlcN-IdoA2S-GlcNAc;
    GlcN-IdoA-GlcNS;
    GlcN-IdoA-GlcNAc6S;
    GlcN-IdoA2-GlcNAc6S; and
    GlcN-IdoA-GlcNS6S.

11. The method of claim 10, wherein biomarker is of Formula V: $[GlcNAc\text{-}IdoA\text{-}GlcN(Ac)_{0\text{-}1}](SO_3R)_{0\text{-}3}$; or Formula VI: $[GlcNAc\text{-}GlcA\text{-}GlcN(Ac)_{0\text{-}1}](SO_3R)_{0\text{-}2}$.

12. The method of claim 11, wherein the biomarker of Formula V is selected from a group consisting of GlcNAc-IdoA-GlcNAc, GlcNAc-IdoA2S-GlcNAc, GlcNAc-IdoA-GlcNS, GlcNAc-IdoA2S-GlcNS, GlcNAc-IdoA-GlcNAc6S, GlcNAc-IdoA2S-GlcNAc6S, GlcNAc-IdoA-GlcNS6S, and GlcNAc-IdoA2S-GlcNS6S.

13. The method of claim 11, wherein the biomarker of Formula VI is selected from a group consisting of GlcNAc-GlcA-GlcNAc, GlcNAc-GlcA-GlcNS, GlcNAc-GlcA-GlcNAc6S, or GlcNAc-GlcA-GlcNS6S.

14. The method of claim 10, wherein the method further comprises purifying the biomarker generated in step (a) to yield an isolated population of biomarkers.

15. The method of claim 14, wherein the biomarker is purified using chromatography or electrophoresis.

16. The method of claim 10, wherein the method further comprises tagging the biomarkers with a detectable label.

17. The method of claim 16, wherein the detectable label is a mass label, a radio label, a fluorescent label, a chromophore label, or affinity label.

18. The method of claim 1, wherein the biomarker is of Formula III: $[GlcNS\text{-}IdoA\text{-}GlcN(Ac)_{0\text{-}1}](SO_3R)_{0\text{-}3}$.

19. The method of claim 18, wherein the biomarker of Formula III is selected from a group consisting of GlcNS-IdoA-GlcNAc, GlcNS-IdoA2S-GlcNAc, GlcNS-IdoA-GlcNS, GlcNS-IdoA2S-GlcNS, GlcNS-IdoA-GlcNAc6S, GlcNS-IdoA2S-GlcNAc6S, GlcNS-IdoA-GlcNS6S, and GlcNS-IdoA2S-GlcNS6S.

20. The method of claim 1, wherein the biomarker is of Formula IV: [GlcNS-GlcA-GlcN(Ac)$_{0-1}$](SO$_3$R)$_{0-2}$.

21. The method of claim 20, wherein the biomarker of Formula IV is selected from a group consisting of GlcNS-GlcA-GlcNAc, GlcNS-GlcA-GlcNS, GlcNS-GlcA-GlcNAc6S, or GlcNS-GlcA-GlcNS6S.

22. The method of claim 1, wherein the biomarker is selected from a group consisting of GlcN-IdoA-GlcNAc, GlcN-IdoA2S-GlcNAc, GlcN-IdoA-GlcNS, GlcN-IdoA-GlcNAc6S, GlcN-IdoA2S-GlcNAc6S, and GlcN-IdoA-GlcNS6S.

23. The method of claim 1, wherein the biomarker is of Formula VIII: [GlcN-GlcA-GlcN(Ac)$_{0-1}$](SO$_3$R)$_{0-4}$.

24. The method of claim 23, wherein the biomarker of Formula VIII is selected from a group consisting of GlcN-GlcA-GlcNAc, GlcN-GlcA-GlcNS, GlcN-GlcA-GlcNAc6S, and GlcN-GlcA-GlcNS6S.

25. The method of claim 1, wherein the biomarker is of Formula IX: [GlcNAc6S-IdoA-GlcN(Ac)$_{0-1}$](SO$_3$R)$_{0-3}$.

26. The method of claim 25, wherein the biomarker of Formula IX is selected from a group consisting of GlcNAc6s-IdoA-GlcNAc, GlcNAc6s-IdoA2S-GlcNAc, GlcNAc6s-IdoA-GlcNS, GlcNAc6s-IdoA2S-GlcNS, GlcNAc6s-IdoA-GlcNAc6S, GlcNAc6s-IdoA2S-GlcNAc6S, GlcNAc6s-IdoA-GlcNS6S, and GlcNAc6s-IdoA2S-GlcNS6S.

27. The method of claim 1, wherein the biomarker is of Formula X: [GlcNAc6S-GlcA-GlcN(Ac)$_{0-1}$](SO$_3$R)$_{0-2}$.

28. The method of claim 27, wherein the biomarker of Formula X is selected from a group consisting of GlcNAc6S-GlcA-GlcNAc, GlcNAc6S-GlcA-GlcNS, GlcNAc6S-GlcA-GlcNAc6S, and GlcNAc6S-GlcA-GlcNS6S.

* * * * *